US012263233B2

(12) United States Patent
Choi et al.

(10) Patent No.: US 12,263,233 B2
(45) Date of Patent: Apr. 1, 2025

(54) COMPOSITIONS AND METHODS FOR MODULATING Myc TARGET PROTEIN 1

(71) Applicant: Washington University, St. Louis, MO (US)

(72) Inventors: Kyunghee Choi, St. Louis, MO (US); Ashraf Ul Kabir, St. Louis, MO (US); Karen Krchma, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/451,428

(22) Filed: Oct. 19, 2021

(65) Prior Publication Data

US 2022/0143220 A1   May 12, 2022

Related U.S. Application Data

(60) Provisional application No. 63/093,595, filed on Oct. 19, 2020.

(51) Int. Cl.
*C12N 15/113* (2010.01)
*A61K 48/00* (2006.01)
*A61P 35/00* (2006.01)

(52) U.S. Cl.
CPC .......... *A61K 48/0066* (2013.01); *A61P 35/00* (2018.01); *C12N 15/113* (2013.01)

(58) Field of Classification Search
CPC .. A61K 48/0066; A61K 31/713; A61K 45/06; A61P 35/00; C12N 15/113; C12N 2310/20; C12N 2320/31; C12N 2310/14; C12N 2310/3513; C12N 2310/531; C12N 2740/16043; C12N 15/1135; A01K 2217/075; A01K 2227/105; A01K 2227/40; A01K 2267/0331; A01K 67/0275
See application file for complete search history.

(56) References Cited

FOREIGN PATENT DOCUMENTS

| WO | WO-2018011166 A2 * | 1/2018 | ........... C12Q 1/6886 |
| WO | WO-2019226514 A2 * | 11/2019 | ........... C12Q 1/6886 |

OTHER PUBLICATIONS

Masiero et al. 2013 A Core Human Primary Tumor Angiogenesis Signature Identifies the Endothelial Orphan Receptor ELTD1 as a Key Regulator of Angiogenesis. Cancer Cell 24:229-241 http://dx.doi.org/10.1016/j.ccr.2013.06.004 (Year: 2013).*
Wu et al. 2016 Transmembrane domain is crucial to the subcellular localization and function of Myc target 1. J. Cell. Mol. Med. 20(3):471-481 (Year: 2016).*

(Continued)

*Primary Examiner* — Kimberly Chong
*Assistant Examiner* — Ruth Sophia Arieti
(74) *Attorney, Agent, or Firm* — Polsinelli PC

(57) ABSTRACT

Among the various aspects herein is the provision of compositions and methods for modulating MYCT1. Methods are provided for regulating tumor angiogenesis (anti-angiogenesis, Myct1-targeted vascular control) and/or immunostimulation, which inhibit tumor growth, in a subject. Methods are provided to quantify MYCT1 to predict responsiveness of a subject having a cancer or tumor to a treatment, guide treatment decisions, select subjects for clinical trials, and evaluate the clinical efficacy of certain therapeutic interventions.

31 Claims, 37 Drawing Sheets
(36 of 37 Drawing Sheet(s) Filed in Color)
Specification includes a Sequence Listing.

(56) References Cited

OTHER PUBLICATIONS

Gaj 2017 In vivo genome editing improves motor function and extends survival in a mouse model of ALS. Science Advances 3: eaar395 (Year: 2017).*
Shifrut 2018 Genome-wide CRISPR Screens in Primary Human T Cells Reveal Key Regulators of Immune Function. Cell 175:1958-1971 (Year: 2018).*
Shifrut 2018 Genome-wide CRISPR Screens in Primary Human T Cells Reveal Key Regulators of Immune Function Supplemental Table S3 (Tab 1). Cell 175:1958-1971 (Year: 2018).*
Shifrut 2018 Genome-wide CRISPR Screens in Primary Human T Cells Reveal Key Regulators of Immune Function Supplemental Table S3 (Tab 2). Cell 175:1958-1971 (Year: 2018).*
Tang et al. 2019 A ligand motif enables differential vascular targeting of endothelial junctions between brain and retina. PNAS 116(6):2300-2305 (Year: 2019).*
Han et al. 2019 Small-Molecule MYC Inhibitors Suppress Tumor Growth and Enhance Immunotherapy. Cancer Cell 36:483-497 https://doi.org/10.1016/j.ccell.2019.10.001 (Year: 2019).*
Aguadé-Gorgorió et al. 2019 Downregulation of Endothelial Gene MYCT1 in Human HSCS During Ex Vivo Culture Compromises Their Function. (Jun. 15, 2019 EHA24 Poster Abstract, European Hematology Association) (Year: 2019).*
Santel et al. 2006. RNA interference in the mouse vascular endothelium by systemic administration of siRNA-lipoplexes for cancer therapy. Gene Ther. 13:1360-1370 (Year: 2006).*
Masiero 2013 (Cancer Cell 24:229-241) Of Record (Year: 2013).*
Davis 2014. Knockout by TALEN or CRISPR vs. Knockdown by shRNA or siRNA. Genecopoeia. Available online at https://www.genecopoeia.com. Accessed Jul. 6, 2023. (Year: 2014).*
Anders et al. 2014. Structural basis of PAM-dependent target DNA recognition by the Cas9 endonuclease. Nature 513:569-575 (Year: 2014).*
Reardon 2014. A New Twist on Gene Editing. Nature 578:24-27 (Year: 2014).*
Wu 2016 (J. Cell. Mol. Med. 20(3):471-481) Of Record (Year: 2016).*
Mills et al. 2019. p5RHH nanoparticle-mediated delivery of AXL siRNA inhibits metastasis of ovarian and uterine cancer cells in mouse xenografts. Sci. Rep. 9:4762 (Year: 2019).*
Aguadé-Gorgorió 2019 (Jun. 15, 2019 EHA24 Poster Abstract) Of Record (Year: 2019).*
Tang et al. 2019 (PNAS 116(6):2300-2305) Of Record (Year: 2019).*
Lee et al. 2020. Combination of anti-angiogenic therapy and immune checkpoint blockade normalizes vascular-immune crosstalk to potentiate cancer immunity. Expt. Molec. Med. 52:1475-1485 (Year: 2020).*
Peterson et al. 2009. Evolutionary constraints on structural similarity in orthologs and paralogs. Protein Sci 18[6]:1306-1315 (Year: 2009).*
Fortelny et al. 2015. The path of no return—Truncated protein N-termini and current ignorance of their genesis. Proteomics 15:2547-2552 (Year: 2015).*
Yang et al. 2016. Widespread Expansion of Protein Interaction Capabilities by Alternative Splicing. Cell 164:805-817 (Year: 2016).*
Gunning and Hardeman. 2018. Isoforms: Fundamental differences. eLife 7:e34477 (Year: 2018).*
Wetterwald et al. 2018. Deciphering the role of a new endothelial protein. Poster Abstract No. 18. From LIMNA Symposium: Central Regulation of Metabolism and Feeding. Presented Nov. 8, 2018 in Lausanne, Switzerland (Year: 2018).*
National Cancer Institute (NCI). 2018. Angiogenesis inhibitors. Available online at cancer.gov. Accessed Feb. 15, 2024 (Year: 2018).*
Teleanu et al. 2019. Tumor Angiogenesis and Anti-Angiogenic Strategies for Cancer Treatment. J. Clin. Med. 9:84 (Year: 2019).*
Wang et al. 2019. MYCT1 represses apoptosis of laryngeal cancerous cells through the MAX/miR-181a/NPM1 pathway. Febs J. 288:3892-3908 (Year: 2019).*
Park (et al. 2014. Effect of siRNA with an Asymmetric RNA/dTdT Overhang on RNA Interference Activity. Nucleic Ac. Ther. 24[5]:364-371 (Year: 2014).*
Aguade-Gorgorio, Downregulation of endothelial gene MYCT1 in human HSCS during ex vivo culture comprises their function, EHA24 Poster Abstract, European Hematolory Association, Jun. 15, 2019.
Santel, RNA interference in the mouse vascular endothellum by system administration of siRNA-lipoplexes for cancer therapy, Gene Ther., 2006, 13:1360-1370.
Masiero, A Core Human Primary Tumor AngiogenesisSignature Identifies the Endotthelial Orphan Receptor ELTD1 as a Key Regulator of Angiogenesis, Cancer Cell, 2013, 24:229-241.
Wu, Transmembrane domain is crucial to the subcellular localization and function of Myc target 1, J. Cell. Mol. Med., 2016, 20(3):471-481.
Tang, A ligand motif enables differential vascular targeting of endothelial junctions between brain and retina, PNAS, Feb. 5, 2019, 116:6):2300-2309.
Lee, Combination of anti-angiogenic therapy and immune checkpoint blockade normalizes vascular-immune crosstalk to potentiate cancer immunity, Expt. Molec. Med., 2020, 52:1475-1485.
Masiero, Supplemental Information Document S1, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S1.1, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S1.2, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S1.3, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S1.4, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S1.6, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S2.1, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S2.2, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S3, A Core Human Primary Tumor AngiogenesisSignature Identifies the Endotthelial Orphan Receptor ELTD1 as a Key Regulator of Angiogenesis, Cancer Cell, 2013, 24:229-241.
Masiero, Supplemental Information Table S4, A Core Human Primary Tumor AngiogenesisSignature Identifies the Endotthelial Orphan Receptor ELTD1 as a Key Regulator of Angiogenesis, Cancer Cell, 2013, 24:229-241.

* cited by examiner

SEQUENCE LISTING

```
<160> NUMBER OF SEQ ID NOS: 1

<210> SEQ ID NO 1
<211> LENGTH: 235
<212> TYPE: PRT
<213> ORGANISM: Homo sapiens

<400> SEQUENCE: 1

Met Arg Thr Gln Val Tyr Glu Gly Leu Cys Lys Asn Tyr Phe Ser Leu
1               5                   10                  15

Ala Val Leu Gln Arg Asp Arg Ile Lys Leu Leu Phe Phe Asp Ile Leu
            20                  25                  30

Val Phe Leu Ser Val Phe Leu Leu Phe Leu Leu Phe Leu Val Asp Ile
        35                  40                  45

Met Ala Asn Asn Thr Thr Ser Leu Gly Ser Pro Trp Pro Glu Asn Phe
    50                  55                  60

Trp Glu Asp Leu Ile Met Ser Phe Thr Val Ser Met Ala Ile Gly Leu
65                  70                  75                  80

Val Leu Gly Gly Phe Ile Trp Ala Val Phe Ile Cys Leu Ser Arg Arg
                85                  90                  95

Arg Arg Ala Ser Ala Pro Ile Ser Gln Trp Ser Ser Ser Arg Arg Ser
                100                 105                 110

Arg Ser Ser Tyr Thr His Gly Leu Asn Arg Thr Gly Phe Tyr Arg His
            115                 120                 125

Ser Gly Cys Glu Arg Arg Ser Asn Leu Ser Leu Ala Ser Leu Thr Phe
    130                 135                 140

Gln Arg Gln Ala Ser Leu Glu Gln Ala Asn Ser Phe Pro Arg Lys Ser
145                 150                 155                 160

Ser Phe Arg Ala Ser Thr Phe His Pro Phe Leu Gln Cys Pro Pro Leu
                165                 170                 175

Pro Val Glu Thr Glu Ser Gln Leu Val Thr Leu Pro Ser Ser Asn Ile
            180                 185                 190

Ser Pro Thr Ile Ser Thr Ser His Ser Leu Ser Arg Pro Asp Tyr Trp
    195                 200                 205
```

-continued

```
Ser Ser Asn Ser Leu Arg Val Gly Leu Ser Thr Pro Pro Pro Ala
    210                 215                 220

Tyr Glu Ser Ile Ile Lys Ala Phe Pro Asp Ser
225                 230                 235
```

COMPOSITIONS AND METHODS FOR MODULATING Myc TARGET PROTEIN 1

CROSS REFERENCE TO RELATED APPLICATIONS

This application claims the benefit of U.S. Provisional Application No. 63/093,595, filed Oct. 19, 2020, the disclosure of which are hereby incorporated by reference in its entirety.

GOVERNMENTAL RIGHTS

This invention was made with government support under HL055337 awarded by the National Institutes of Health. The government has certain rights in the invention.

FIELD OF THE TECHNOLOGY

The present disclosure relates, in general, to compositions and methods for the treatment for predicting outcome of cancer therapeutics. More specifically, the present disclosure provides compositions and methods which prevent or reduce tumor angiogenesis, remodels tumor immunity, and improves immunotherapy outcomes.

BACKGROUND

Angiogenesis and immune tolerance are both normal physiologic mechanisms that are hijacked by tumors. Angiogenesis involves the formation of new vessels from preexisting ones during development and wound healing. The modulation of angiogenesis is highly regulated by proangiogenic and antiangiogenic factors, a process that becomes disrupted and dysregulated in cancer. Tumor-driven hypoxia increases the expression of proangiogenic factors leading to the formation of new vessels that are vital to the tumor survival and proliferation. The VEGF family, consisting of six growth factors (VEGFA-F), plays the most critical role in angiogenesis by binding to their receptors VEGFR1-3 and neuropilin. Angiogenesis can also be mediated by the angiopoietin (Ang1-2)/Tie-2 pathway, independent from the VEGF pathway. Accordingly, drug development was heavily focused on anti-angiogenesis in the past decade as a strategy to deprive tumor's nutrition and inhibit tumor growth. However, despite the modest activities of these agents as single agents or in combination with chemotherapy, tumors can overcome their effects and become resistant.

Cancer immunotherapy has emerged as a modality that can effectively treat a variety of cancers with the discovery of immune checkpoints. A plethora of investigations with immune checkpoint inhibitors (ICI) has demonstrated a long-lasting clinical activity against many malignancies. ICIs block another mechanism hijacked by tumor "immune exhaustion," unleashing the effector immune cells against cancer. Primary resistance to ICIs is described in tumors that lack tumor-infiltrating lymphocytes. In addition, tumors that initially respond to ICIs can develop secondary resistance due to defects in antigen-presenting machinery and the overexpression of coinhibitory molecules among other factors.

Accordingly, there is a need in the art for compositions and methods which address angiogenesis and immune exhaustion.

BRIEF DESCRIPTION OF THE FIGURES

The application file contains at least one drawing executed in color. Copies of this patent application publication with color drawing(s) will be provided by the Office upon request and payment of the necessary fee.

FIG. 1A shows the correlation between the 'angiogenic score' and MYCT1 expression in TCGA-derived breast cancer (TCGA-BRCA), LSCC (TCGA-LUSC), sarcoma (TCGA-SARC), prostate cancer (TCGA-PRAD), and CCRCC (TCGA-KIRC) patient datasets (Pearson's $\chi^2$ test; R values are indicated with respective datasets). FIG. 1B shows the Analysis of Myct1 expression in CD31+CD45− ECs isolated from the mammary glands of healthy wild-type (WT) mice, and the lungs and mammary tumors of WT MMTV-PyMT mice at 21 weeks of age (left) and lungs and tumors of the tumor-bearing WT mice at 14-days post LLC tumor transplantation (right). n=6 mice per group. Data is presented as mean with standard deviation (SD) from one of two biological replicates. Statistical significance was analyzed by One-way ANOVA with Tukey's multiple comparison test (left) and two-tailed Student's t-test (right). FIG. 1C shows a genomic snapshot illustrating the ETV2 binding peak to the Myct1 promoter region. FIG. 1D shows ChIP-qPCR analysis of ETV2 binding to the Myct1 promoter region. Data is presented as mean with SD. Statistical significance was analyzed by Two-way ANOVA followed by Tukey's multiple comparison test. mt=mutant. FIG. 1E shows a graphical representation of the luciferase construct design. FIG. 1F shows analysis of the normalized reporter activity for ETV2 binding motif on Myct1. Data is presented as mean with SD. Statistical significance was analyzed by One-way ANOVA with Tukey's multiple comparison test; ***$p<0.001$, compared to the respective values in the absence of ETV2 (null). FIG. 1G shows analysis of Myct1 expression in CD31+CD45− ECs isolated from the tumors of WT and VEC-Cre; Etv2f/f (Etv2 KO) mice at 15-days post LLC tumor transplantation. n=6 mice per group. Data is presented as mean with SD from one of two biological replicates. Statistical significance was analyzed by two-tailed Student's t-test. FIG. 1H shows tumor growth. FIG. 1I shows representative images with quantification for CD31+ vessel density (I) in PBS (control) and Myct1 lentiviral overexpression construct (intra-tumor) treated WT and Etv2 KO mice. n=7 mice per group. Scale bars, 100 µm. Data is presented as mean with SD from one of two biological replicates. Statistical significance was analyzed by two-tailed Student's t-test; *$p<0.05$, at the end of the study. FIG. 1J shows analysis of vital cardiovascular parameters. FIG. 1K shows pressure-diameter measurements (K) in the Myct1 KO and WT mice. n=9 (Myct1 KO) and 11 (WT) mice. Data is presented as mean with SD from one of two biological replicates. Statistical significance was analyzed by two-tailed Student's t-test (J) and One-way ANOVA with Tukey's multiple comparison test (K); n.s.=not significant. FIG. 1L shows analysis of clinically important cardiac functional parameters measured by Doppler echocardiogram of Myct1 KO and WT mice. n=3 (WT) and 4 (Myct1 KO) mice. Data is presented as mean with SD. Statistical significance was analyzed by two-tailed Student's t-test; n.s.=not significant.

FIG. 2A shows analysis of total tumor burden. FIG. 2B shows representative images with quantification of CD31+ vessel density (B) in WT and Myct1 KO MMTV-PyMT mice at 21 weeks of age. n=14 mice per group. Scale bars, 100 µm. Data is presented as mean with SD. Statistical significance was analyzed by two-tailed Student's t-test; *$p<0.001$. FIG. 2C shows representative images with quantification for CD31+ vessel density (D) in WT and Myct1 KO mice. Scale bars, 100 µm. Data is presented as mean with SD from one of three biological replicates. Statistical significance was analyzed by two-tailed Student's t-test; p<0.01, at the end of the study. FIG. 2E shows analysis of 1956-sarcoma tumor growth. FIG. 2F shows presentative images with quantification for CD31+ vessel density (F) in WT and Myct1 KO mice. Scale bars, 100 µm. Data is presented as mean with SD from one of three biological replicates. Statistical significance was analyzed by two-tailed Student's t-test; p<0.001, at the end of the study. FIG. 2G shows analysis of tumor growths. FIG. 2I shows representative images with quantification for CD31+ vessel density. FIG. 2J shows representative images with quantification for CD31+ vessel density in stromal Myct1 KO (G and H) and hematopoietic Myct1 KO mice (I and J). Scale bars, 100 µm. Data is presented as mean with SD. Statistical significance was analyzed by two-tailed Student's t-test; n.s.=not significant and p<0.01, at the end of the study.

FIG. 3A shows flow cytometric analysis of HA- and FLAG-tagged MYCT1 overexpressing MCEC cells. (right) A graphical presentation of the HA- and FLAG-tagged MYCT1 protein situated at the plasma membrane. FIG. 3B shows a representative FACS chart of the BrdU proliferation assay with parental and Myct1 knockdown (KD) cells. FIG. 3C shows representative images and quantifications from the Matrigel tube formation assay. n=12 independent observations per group. Scale bars, 250 µm. Data is presented as mean with SD from one of three biological replicates. Statistical significance was analyzed by two-tailed Student's t-test; p<0.01. FIG. 3D shows representative images from tumor-spheroid/EC co-culture assay. Scale bar, 1000 µm. FIG. 3E shows representative images and quantifications of sprouts from the fibrin gel sprouting assay. n≥32 independent observations per group. Scale bars, 100 µm. Data is presented as mean with SD from one of three biological replicates. Statistical significance was analyzed by two-tailed Student's t-test; p<0.01. FIG. 3F shows representative image and quantification of sprouts from the fibrin gel sprouting assay with 1:1 competitive seeding of parental (red) and Myct1 KD (green) MCEC cells on the beads. Scale bar, 100 µm. Data is presented as mean with SD. Statistical significance was analyzed by two-tailed Student's t-test; p<0.05. FIG. 3G shows representative images and quantifications of cell migration from the Boyden chamber assay. n≥12 independent observations per group. Scale bars, 100 µm. Data is presented as mean with SD from one of three biological replicates. Statistical significance was analyzed by two-tailed Student's t-test; p<0.01. FIG. 3H shows representative images and quantifications for recovery from the wound closure assay. n≥3 independent observations per group. Scale bars, 100 µm. Data is presented as mean with SD from one of two biological replicates. Statistical significance was analyzed by two-tailed Student's t-test; **p<0.05. FIG. 3I shows representative immunofluorescence images of actin filaments in a cultured monolayer of MCEC cells. Scale bars, 25 µm. FIG. 3J shows immunoprecipitation followed by western blot (IP-WB) analysis for MYCT1 in the total cell lysates of the parental and HA-tagged MYCT1 overexpressing (HA-MYCT1) MCEC cells transfected with either mock (empty vector control) or MYC-tagged ZO1, and FLAG-tagged CKAP4 expression plasm ids. An anti-ACTIN antibody was used as a control. FIG. 3K shows IP-WB analysis for CKAP4 in the total cell lysates of the parental MCEC cells transfected with either mock (empty vector control), or MYC-tagged ZO1, or FLAG-tagged CKAP4 expression plasm ids. An anti-ACTIN antibody was used as a control. FIG. 3L shows representative immunofluorescence image of ZO1 (green) and MYCT1 (anti-FLAG, red) in a confluent monolayer of FLAG-tagged MYCT1 overexpressing MCEC cells. Scale bars, 20 µm.

FIG. 4A shows representative images and quantifications from the Matrigel tube formation assay (A). FIG. 4B shows Boyden chamber migration assay. FIG. 4C shows fibrin gel bead sprouting angiogenesis assay (C) with parental, human MYCT1 KD (hMKD), and mouse Myct1 overexpressing human MYCT1 KD (hMKD mMOE) HUVEC cells. Scale bar, 250 µm (A) and 100 µm (B and C). n≥10 independent observations per group. Data is presented as mean with SD from one of three biological replicates. Statistical significance was analyzed by One-way ANOVA with Tukey's multiple comparison test; **p<0.05. FIG. 4D shows Representative images and quantifications from the Matrigel tube formation assay. FIG. 4E shows Boyden chamber migration assay. FIG. 4F shows fibrin gel sprouting assay (F) with parental, mouse Myct1 KD (mMKD), and human MYCT1 overexpressing mouse Myct1 KD (mMKD hMOE) MCEC cells. Scale bars, 250 µm (D) and 100 µm (E and F). n≥10 independent observations per group. Data is presented as mean with SD from one of three biological replicates. Statistical significance was analyzed by One-way ANOVA with Tukey's multiple comparison test; *p<0.05 and **p<0.01. FIG. 4G shows analysis of tumor growth. FIG. 4H shows representative immunofluorescence images with quantification for CD31+ vessel density (H) in PBS (control) and either mouse Myct1 or human MYCT1 lentiviral overexpression constructs (intra-tumor) treated WT and Myct1 KO mice. Scale bars, 100 µm. Data is presented as mean with SD. Statistical significance was analyzed by One-way ANOVA with Tukey's multiple comparison test; n.s.=not significant and *p<0.05, at the end of the study.

FIG. 5A show A schematic representation of tumor endothelium sample collection and processing from WT and Cdh5-cre Myct1f/f mice (n=5 per group) for single cell RNA sequencing. FIG. 5P show area under the curve (AUC) plots for differentially enriched transcription factor activity modules (P) in WT and Cdh5-cre Myct1f/f tumor endothelium generated by using SCENIC analysis.

FIG. 6A shows representative immunofluorescence images and quantification of MECA79+ high endothelial venules (HEVs) in 1956 sarcoma tumor. White dotted boxed area from the inset is presented as zoomed-in. Arrows in the inset indicate the MECA79 expressing vessels. Scale bars, 10 µm and 20 µm (inset). Data is presented as mean with SD. Statistical significance was analyzed by two-tailed Student's t-test; $p<0.01$. FIG. 6B shows CTL (CD8+ T cells) and Treg (CD4+FOXP3+ T cells) cells as a percentage of CD3+ T cells and M1 (iNOS+ macrophages) and M2 (CD206+ macrophage) populations as a percentage of F4/80+ cells. n=6 mice per group. Data is presented as mean with SD. Statistical significance was analyzed by two-tailed Student's t-test; $p<0.01$. FIG. 6C shows Analysis of CD8/Treg and M1/M2 ratios as measures of immunosuppression in the tumor microenvironment of WT and Myct1 KO mice. n=6 mice per group. Data is presented as mean with SD. Statistical significance was analyzed by two-tailed Student's t-test; n.s.=not significant, *$p<0.05$, and **$p<0.01$. FIG. 6D shows analysis of FOXP3 expression in high vs. low MYCT1 expressing tumors in patients from the TCGA database. (bottom) Analysis of M1/M2 population ratios in high vs. low MYCT1 expressing tumors obtained by analyzing the TCGA patient datasets with the CIBERSORT algorithm. Datasets utilized were BC (TCGA-BRCA), LAC (TCGA-LUAD), TT (TCGA-TGCT), SAC (TCGA-STAD), LSCC (TCGA-LUSC), CAC (TCGA-COAD), HNSCC (TCGA-HNSC), OC (TCGA-OV), PC (TCGA-PRAD), PAC (TCGA-PDAC), Sarcoma (TCGA-SARC), CCRCC (TCGA-KIRC), PRCC (TCGA-KIRP), and BLC (TCGA-BLCA). Data is presented as scatter plot with the mean value. Statistical significance was analyzed by Mann-Whitney U test; *$p<0.05$ and **$p<0.01$. FIG. 6E shows analysis of tumor growth in either IgG or combined anti-CD4 and anti-CD8 neutralizing antibody treated Myct1 KO mice. n=5 mice per group. Data is presented as mean with SD from one of two biological replicates. Statistical significance was analyzed by One-way ANOVA with Tukey's multiple comparison test; $p<0.001$, at the end of the study. FIG. 6F shows analysis of tumor growth in either IgG, or anti-IFNγ neutralizing antibody, or combined anti-CD4 and anti-CD8 neutralizing antibody, or combined anti-CD4 and anti-CD8 neutralizing antibody with IFNγ cytokine treated Myct1 KO mice. Data is presented as mean with SD. Statistical significance was analyzed by One-way ANOVA with Tukey's multiple comparison test; 'p-values' indicated on the figure are calculated at the end of the study. FIG. 6G shows Transendothelial migration (TEM) of CD8+ T cells through parental and Myct1 KD MCEC cell barrier with TNFα and Rac1 inhibitor NSC23766 pre-treatment. Data is presented as mean with SD. Statistical significance was analyzed by One-way ANOVA with Tukey's multiple comparison test; n.s.=not significant, *$p<0.05$, and **$p<0.01$. FIG. 6H shows analysis of mRNA expression of the indicated genes in CD31+CD45− ECs isolated from the 1956 sarcoma tumors. n=4 mice per group. Statistical significance was analyzed by Statistical significance was analyzed by two-tailed Student's t-test; *$p<0.05$ and **$p<0.01$. FIG. 6I shows analysis of mRNA expression of the indicated genes in CD31+CD45− ECs isolated from the 1956 sarcoma tumors. n=4 mice per group. Statistical significance was analyzed by Statistical significance was analyzed by two-tailed Student's t-test; *$p<0.05$ and **$p<0.01$. FIG. 6J shows FASLG expression profile in high vs. low MYCT1 expressing tumors in SAC (TCGA-STAD), LSCC (TCGA-LUSC), CAC (TCGA-COAD), OC (TCGA-OV), PC (TCGA-PRAD), PAC (TCGA-PDAC), Sarcoma (TCGA-SARC), CCRCC (TCGA-KIRC), and PRCC (TCGA-KIRP) patients from the TCGA database. Data is presented as mean with standard error of mean. Statistical significance was analyzed by two-tailed Student's t-test; *$p<0.05$ and **$p<0.01$. FIG. 6K shows polarization of peripheral blood-derived monocytes to M1 or M2 phenotype with LPS+IFNγ or IL4 cytokine treatment, respectively, in a coculture assay with either parental or Myct1 KD MCEC cells, expressed as a percentage of F4/80+ macrophage population. Data is presented as mean with SD. Statistical significance was analyzed by two-tailed Student's t-test; *$p<0.05$ and $p<0.01$. FIG. 6L shows analysis of Nos2 and Nos3 mRNA expression in CD31+CD45− ECs isolated from the 1956 sarcoma tumor. n=4 mice per group. Data is presented as mean with SD. Statistical significance was analyzed by two-tailed Student's t-test; $p<0.01$.

FIG. 7A shows kinetics of tumor growth in 1956 sarcoma tumor bearing WT mice treated with anti-PD1 antibody in different indicated schemes. Donut charts display the percentage of subjects underwent complete regression (green) and non-complete regression (gray). Day-21 statistical significance was analyzed by One-way ANOVA with Tukey's multiple comparison test. FIG. 7B shows Analysis of tumor progression in 1956 sarcoma tumor bearing WT and Myct1 KO mice at 12-days after anti-PD1 treatment initiation. Data is presented as mean with SD. Statistical significance was analyzed by One-way ANOVA with Tukey's multiple comparison test; *$p<0.05$, $p<0.01$, and *$p<0.001$. FIG. 7C shows Tumor growth in 1956 sarcoma tumor bearing WT and Myct1 KO mice treated with the anti-PD1 antibody. Donut charts display the percentage of subjects underwent complete regression (green) and non-complete regression (gray). Day-21 statistical significance was analyzed by One-way ANOVA with Tukey's multiple comparison test. FIG. 7D shows analysis of tumor progression in 1956 sarcoma tumor bearing WT mice at 13-days after treatment initiation as indicated. Data is presented as mean with SD. Statistical significance was analyzed by One-way ANOVA with Tukey's multiple comparison test; *$p<0.05$, $p<0.01$, and *$p<0.001$. FIG. 7E shows tumor growth in 1956 sarcoma tumor bearing WT mice with different treatments as indicated. Donut charts display the percentage of subjects underwent complete regression (green) and non-complete regression (gray). FIG. 7F shows tumor growth in 1956 tumor bearing WT mice treated with the anti-PD1 antibody in combination with an extended anti-Myct1 siRNA-peptide nanoparticle treatment. Day-21 statistical significance was analyzed by One-way ANOVA with Tukey's multiple comparison test. FIG. 7G shows Kinetics of tumor growth in PyMT-BO1 tumor bearing WT mice treated with anti-PD1 antibody in different schemes. Donut charts display the percentage of subjects underwent complete regression (green) and non-complete regression (gray). FIG. 7H shows tumor progression in PyMT-BO1 tumor bearing WT mice at 15-days after treatment initiation as indicated. Data is presented as mean with SD. Statistical significance was analyzed by One-way ANOVA with Tukey's multiple comparison test; n.s.=not significant, $p<0.01$, and *$p<0.001$. FIG. 7I shows tumor growth in PyMT-BO1 tumor bearing WT mice with different treatments as indicated. Donut charts display the percentage of subjects underwent complete regression (green) and non-complete regression (gray).

FIG. 8A shows analysis of CTL (CD8+ T cells) and Treg (CD4+ FOXP3+ T cells) cells as a percentage of CD3+ T cells, GranzB+ CTL as % of CTL cells, M1 (iNOS+ macrophages) and M2 (CD206+ macrophage) populations as a percentage of F4/80+ cells in the tumor of the PyMT-BO1 tumor bearing WT mice with different combination of treatments as indicated. n=3-6 mice per group. Data is presented as mean with SD. Statistical significance was analyzed by One-way ANOVA with Tukey's multiple comparison test; *$p<0.05$ and $p<0.01$. FIG. 8B shows representative images. FIG. 8C shows pericyte coverage. FIG. 8D shows quantifications (E) for CD31+ vascular density (B), pericyte coverage (C), and CD8+ T cell infiltration in the tumor mass of PyMT-BO1 tumor bearing WT mice with different combination of treatments as indicated. n=3-6 mice per group. Data is presented as mean with SD. Statistical significance was analyzed by One-way ANOVA with Tukey's multiple comparison test; $p<0.01$. FIG. 8E shows quantifications (E) for CD31+ vascular density. FIG. 8F shows Analysis of the expression of the indicated genes in the tumor ECs, hematopoietic cells (HC), and tumor cells sorted from the PyMT-BO1 tumor bearing WT mice with different combination of treatments as indicated. n=3-6/group. Data is presented as mean with SD. Statistical significance was analyzed by One-way ANOVA with Tukey's multiple comparison test; *$p<0.05$ and **$p<0.01$.

DETAILED DESCRIPTION

Figure 1A:
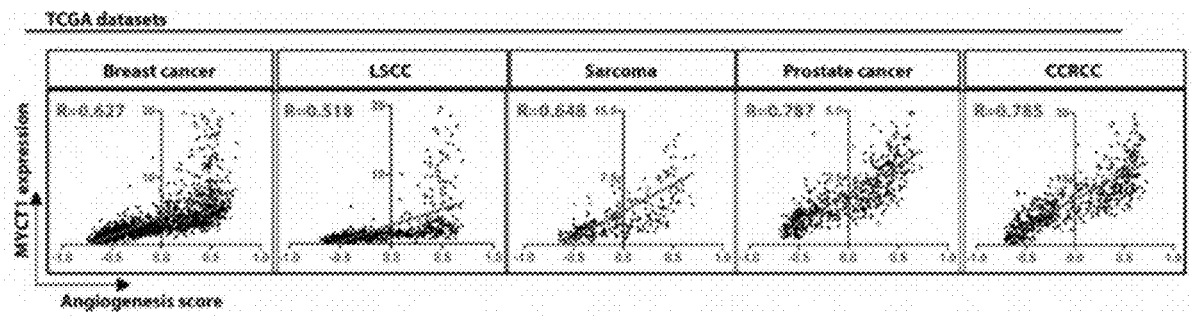
FIG. 1A-1L depict ETV2 direct target gene Myct1 is a regulator of angiogenesis but is not required for vascular development and homeostasis.

Both immune checkpoint inhibitors (ICI) and anti-angiogenesis agents have changed the landscape of cancer treatment in the modern era. While anti-angiogenesis agents have demonstrated activities in tumors with high vascularization, including renal cell carcinoma and colorectal cancer, the effect of ICIs has been seen mainly in immunologically recognized tumors, with highly immune-infiltrative lymphocytes. The main challenge in the drug development of ICIs is moving their activities to noninflamed tumors and overcoming resistance that is driven, in part, by the immune-suppressive microenvironment. Angiogenesis factors drive immune suppression by directly suppressing the antigen-presenting cells as well as immune effector cells or through augmenting the effect of regulatory T cells (Treg), myeloid-derived suppressor cells (MDSC), and tumor-associated macrophages (TAM). Those suppressive immune cells can also drive angiogenesis, creating a vicious cycle of impaired immune activation. Though the mechanisms which regulate tumor angiogenesis and reprogramming tumor immunity are not fully understood. Applicant has discovered compositions and certain methods to reduce or prevent tumor growth, reduce or prevent tumor angiogenesis (i.e., the formation and development of the vasculature that tumors need in order to thrive and progress), increase high endothelial venules (HEVs)(specialized vascular structures that mediate large scale lymphocyte extravasation in lymphoid organs and inflammatory sites), increase tumor immune response, increase T cell infiltration, increase tumor cytotoxic T cell-to-Treg ratio, increase M1-macrophage numbers, decrease M2-macrophage numbers and/or decrease the expression of the Fas ligand in endothelial cells. Thus, the present disclosure encompasses use of the compositions and methods treat a tumor in a subject. In particular, the present disclosure provides that MYCT1 expression and/or activity is required in controlling tumor angiogenesis and reprogramming tumor immunity. The Applicant has discovered compositions which down-regulate MYCT activity and/or expression in cells (e.g., endothelial cells). The down-regulation is associated with reduced angiogenesis, enhanced high endothelial venule formation, and promoted an anti-tumor immune environment, leading to restricted tumor progression. Accordingly, the present disclosure provides compositions and methods for selectively reducing or preventing angiogenesis and increasing tumor immune response.

Discussed below are components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Other aspects and iterations of the invention are described more thoroughly below.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also be ±4%, 3%, 2%, 1%, etc. Whether or not modified by the term "about," the claims include equivalents to the quantities.

The term "antibody," as used herein, is used in the broadest sense and encompasses various antibody and anti-body-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alpha-bodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchangeably, and refer to an antibody having a structure substantially similar to a native antibody structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved framework regions (FRs) and three hypervariable regions (HVRs). (See, e.g., Kindt et al. Kuby Immunology, 6th ed., W. H. Freeman and Co., page 91 (2007).) A single VH or VL domain may be sufficient to confer antigen-binding specificity. Furthermore, anti-bodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as com-pared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); (d) CDR1-IMGT (positions 27-38), CDR2-IMGT (positions 56-65), and CDR3-IMGT regions (positions 105-116 or 105-117), which are based on IMGT unique numbering (Lefranc, "The IMGT unique numbering for Immunoglobulins, T cell receptors and Ig-like domains," The Immunologist, 1999, 7: 132-136; Lefranc et al., Nucleic Acids Research, 2009, 37 (Database issue): D1006-D1012; Ehrenmann et al., "Chapter 2: Standardized Sequence and Structure Analysis of Antibody Using IMGT," in Antibody Engineering Volume 2, Eds. Roland E. Kontermann and Stefan Dubel, 2010, Springer-Verlag Berlin Heidelberg, doi: 10.1007/978-3-642-01147-4; www.imgt.org/IMGTScientificChart/Nomenclature/IMGT-FRCDRdefinition. html), and (e) combinations of (a), (b), (c), and/or (d), as defined below for various antibodies of this disclosure. Unless otherwise indicated, HVR residues and other residues in the variable domain (e.g., FR residues) that are assigned sequence identification numbers are numbered based on IMGT unique numbering, supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab, Fab', Fab'-SH, F(ab')2; single-chain forms of antibodies and higher order variants thereof; single-domain antibodies, and multi-specific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG do-main, such as IgG1, IgG2, IgG3, or IgG4, or a heavy chain constant domain derived from IgA, IgM, or IgE). Diabodies, triabodies, and tetrabodies and higher order variants are typically created by varying the length of the linker peptide from zero to several amino acids. Alternatively, it is also well known in the art that multivalent binding antibody variants can be generated using self-assembling units linked to the variable domain.

A "single-domain antibody" refers to an antibody fragment consisting of a single, monomeric variable antibody domain.

Multi-specific antibodies include bi-specific antibodies, tri-specific, or anti-bodies of four or more specificities. Multi-specific antibodies may be created by combining the heavy and light chains of one antibody with the heavy and light chains of one or more other antibodies. These chains can be covalently linked.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germ line by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived), e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows or using similar methods familiar to those with skill in the art (for example, see Almagro, et al. Front. Biosci. 2008, 13(5):1619-33). A murine antibody variable region is aligned to the most similar human germ line sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different re-version mutations are generated and empirically tested for activity. The humanized antibody variant with properties most similar to the parent murine antibody and the fewest murine framework reversions is selected as the final humanized antibody candidate.

The term "specifically binds," as used herein with regards to epitope binding agents, means that an epitope binding agent does not cross react to a significant extent with other epitopes on the protein of interest (e.g., MYCT1), or on other proteins in general.

The terms "Myc Target 1", "MYC Target Protein 1", "MTLC", "Myc Target In Myeloid Cells Protein 1" or "MYCT1" encompasses all MYCT isoforms and orthologs, whether full-length, truncated, or post-translationally modified. In many animals, including but not limited to humans, non-human primates, rodents, fish, cattle, frogs, goats, and chicken, MYCT1 is encoded by the gene Myct1 gene (aka FLJ21269 and MTLC). The gene encoding MYCT1 is located on chromosome 6 (band q25.2; chromosome location (bp) 152697895-152724567) in humans. MYCT1 was initially identified as a novel target of the c-Myc oncogene in myeloid cells. Previous reports have suggested overexpression in cancer cells can promote apoptosis, alteration of morphology, enhancement of anchorage-independent cell growth, tumorigenic conversion, promotion of genomic instability, and inhibition of hematopoietic differentiation. MYCT1 was initially thought to be a transcription factor and binds to the promoters of several c-Myc-regulated genes and it has been suggested that the phenotypes seen in MYCT1-overexpressing cells are a result of the deregulation of these genes.

In an exemplary aspect, a full length MYCT polypeptide, which is 235 amino acids in length includes the amino acid sequence of SEQ ID NO: 1 (MRTQVYEGLCKNYFSLAVLQRDRIKLLFFDIL-VFLSVFLLFLLFLVDIMANNTTSLGSPW PENFWEDLIMSFTVSMAIGLVLGGFIWAVFICLSRRR-RASAPISQWSSSRRSRSSYTHG LNRTGFYRHSGCERRSNLSLASLTFQRQASLEQANSF-PRKSSFRASTFHPFLQCPPLP VETESQLVTLPSSNISP-TISTSHSLSRPDYWSSNSLRVGLSTPPPPAYES-IIKAFPDS). In an exemplary aspect, a full length MYCT1 mRNA transcript, which is 3030 base pairs in length includes the NCBI Reference Sequence: NM_025107.3. Additional reference MYCT1 mRNAs include but are not limited to NM 001371624.1, NM 001371625.1, NM 001371626.1, and NM 025107.3. In an exemplary aspect, regulatory elements which modulate the expression of MYCT1 include those described herein and those disclosed in Gene Card ID: GC06P152697.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

II. Compositions

In an aspect, a composition of the disclosure comprises a composition that modulates MYCT1. Specifically, a composition that modulates MYCT1 may be a composition that down-regulates MYCT1 expression and/or activity. In some embodiments, the composition that modulates MYCT1 comprises a compound inhibitor of MYCT1, a small molecule inhibitor of MYCT1, a drug inhibitor of MYCT1, a MYCT1 blocking antibody, a MYCT1 blocking peptide, a MYCT1 antagonist, a MYCT1 inhibitory RNA and combinations thereof. A nucleic acid molecule may be an antisense oligonucleotide, a ribozyme, a small nuclear RNA (snRNA), a long noncoding RNA (LncRNA), or a nucleic acid molecule which forms triple helical structures.

A composition of the disclosure may optionally comprise one or more additional drug or therapeutically active agent in addition to a compound that modulates MYCT1. For example, a composition of the disclosure may optionally comprise one or more immune checkpoint blockade compounds. Specifically, a composition of the invention may optionally comprise one or more PD-1 inhibitor and/or PD-L1 inhibitor compounds. Non limiting examples of immune checkpoint compounds include monoclonal antibodies that target either PD-1 or PD-L1 can block this binding and boost the immune response against cancer cells, Pembrolizumab, Nivolumab, Cemiplimab, Atezolizumab, Avelumab, Durvalumab, and/or Ipilimumab. Still further, a composition of the disclosure may optionally comprise one or more anti-VEGF therapies. In non-limiting examples, a composition of the invention may optionally comprise one or more of axitinib, bevacizumab, cabozantinib, lapatinib, Lenvatinib, pazopanib, ponatinib, ramucirumab, ranibizumab, regorafenib, sorafenib, sunitinib and/or vandetanib.

A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

(a) MYCT1 Nucleic Acid Expression

As described herein, an MYCT1 inhibitor can be used for use in cancer or tumor therapy. For example, an MYCT1 inhibitor can be a short hairpin RNA (shRNA) specific for MYCT1. As another example, an MYCT1 inhibitor can be a short interfering RNA (siRNA) specific for MYCT1. Non-limiting examples include those described in the Examples below, MTLC siRNA (santa cruz cat #sc-95588), MTLC shRNA Plasmid (santa cruz cat #sc-95588-SH), MTLC shRNA (h) Lentiviral Particles (santa cruz cat #sc-95588-V), MYCT1 siRNA (origene #SR312826), MYCT1 shRNA (origene #TL303086), and shRNA lentiviral particle (origne #TL303086V). In some embodiments, MYCT1 specific RNAi molecules can be formulated as nanoparticles (e.g. a protein nanoparticle) or administered as a vector (e.g. a viral vector) or viral particle.

As another example, RNA (e.g., long noncoding RNA (lncRNA)) can be targeted with antisense oligonucleotides (ASOs) as a therapeutic. Processes for making ASOs targeted to RNAs are well known; see e.g. Zhou et al. 2016 Methods Mol Biol. 1402:199-213. Except as otherwise noted herein, therefore, the process of the present disclosure can be carried out in accordance with such processes. Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

As another example, an MYCT1 inhibiting agent can be an sgRNA targeting MYCT1. Inhibiting MYCT1 can be performed by genetically modifying MYCT1 in a subject or genetically modifying a subject to reduce or prevent expression of the MYCT1 gene (e.g. by disrupting the gene regulatory region at the Myct1 locus), such as through the use of CRISPR-Cas9 or analogous technologies, wherein, such modification reduces or prevents MYCT1 expression. Processes for genome editing are well known; see e.g. Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of MYCT1 by genome editing can result in protection from proliferative diseases, cancer.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a (N)20NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for cancer to target epithelial cells by the removal of MYCT1 activity (e.g., downregulate MYCT1).

For example, the methods as described herein can comprise a method for altering a target polynucleotide sequence in a cell comprising contacting the polynucleotide sequence with a clustered regularly interspaced short palindromic repeats-associated (Cas) protein.

In an embodiment, MYCT1 nucleic acid expression may be measured to identify a compound that modulates MYCT1. For example, when MYCT1 nucleic acid expression is decreased in the presence of a compound relative to an untreated control, the compound downregulates MYCT1. In a specific embodiment, MYCT1 mRNA may be measured to identify a compound that modulates MYCT1.

Methods for assessing an amount of nucleic acid expression in cells are well known in the art, and all suitable methods for assessing an amount of nucleic acid expression known to one of skill in the art are contemplated within the scope of the disclosure. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an siRNA nucleotide sequence of the disclosure. This allows comparisons between assays that are performed on different occasions.

(b) MYCT1 Protein

One aspect of the present disclosure provides for targeting of MYCT1 using an modulator which specifically binds the MYCT1 protein and either reduces or blocks MYCT1 activity (e.g. binding to other proteins) or reduces MYCT1 protein levels. As described herein, inhibitors of MYCT1 (e.g., antibodies, antibody mimetics, fusion proteins) can reduce or prevent cancer progression. For example, the MYCT1 inhibiting agent can be an anti-MYCT1 antibody. Furthermore, the anti-MYCT1 antibody can be a murine antibody, a humanized murine antibody, or a human antibody. The anti-MYCT1 antibody can be an antagonist anti-MYCT1 antibody. In one embodiment, an anti-MYCT1 antibody binds the extracellular N-terminal portion of MYCT1. Exemplary MYCT1 antibodies include but are not limited to antibodies-online catalog numbers ABIN953561, ABIN1449981, ABIN728015, ABIN2844207, ABIN654473, ABIN1077374, ABIN1587859, ABIN2446414, ABIN5584063, ABIN1544657, ABIN2790424, ABIN1915516, ABIN1915517, ABIN1915518, ABIN1915519, ABIN1915520, ABIN1915521, ABIN2311197, ABIN2311201, ABIN2311207, ABIN2311214, ABIN2585213, ABIN1811760, ABIN2311204, ABIN2311210, ABIN2311218, ABIN5556434, ABIN5705270, ABIN728017, ABIN728024, ABIN1103156, ABIN1490313, ABIN1492644, ABIN2804350, ABIN5007102, ABIN5007103, ABIN728018, ABIN728019, ABIN728020, ABIN728021, ABIN728022, ABIN907253, ABIN907254, ABIN907255, ABIN907256; Proteintech Group number 22004-1-AP;

Invitrogen Antibodies product number PA5-109999, PA5-24018, PA5-34450; Acris Antibodies GmbH product number AP52787PU-N, AP55477PU-N; OriGene product number AP52787PU-N; TA320027; TA331273; Biorbyt product number orb28422, orb448301, orb17003, orb540521, orb13896, orb485975; Abgent product number AP10516b, APS11546; GeneTex product number GTX32092; Bioss product number bs-0334R, bs-0334R-Biotin, bs-0334R-HRP, bs-0334R-A350, bs-0334R-A488, bs-0334R-A555, bs-0334R-A594, bs-0334R-A647, bs-0334R-A680, bs-0334R-A750, bs-0334R-Cy3, bs-0334R-Cy5, bs-0334R-Cy5.5, bs-0334R-Cy7, bs-0334R-FITC; Boster Biological Technology product number A12155; NovoPro Bioscience Inc. product number 112919; Wuhan Fine Biotech Co., Ltd. Product number FNab05461; LifeSpan BioSciences, Inc. product number LS-C153651, LS-C164700, LS-C169779, LS-C474031, LS-C474032, LS-C474033, LS-C749543, LS-C816761, LS-C237858, LS-C237859, LS-C237860, LS-C237861, LS-C237862, LS-C248868, LS-C323185, LS-C666983, LS-0555268, LS-0574917, LS-0594571, LS-C614220, LS-C633872; Aviva Systems Biology product number OAAB00529, ARP66407_P050; Abnova Corporation product number PAB25626; MyBioSource product number MBS9203418, MBS153607; ProSci product number 7031; St John's Laboratory product number STJ116752; United States Biological product number 038724, 038724-AP, 038724-APC, 038724-Biotin, 038724-FITC, 038724-ML405, 038724-ML490, 038724-ML550, 038724-ML650, 038724-ML750, 038724-PE, 38724, 038724-HRP; Creative Diagnostics product number DPABH-02113; MilliporeSigma/Merck KGaA product number HPA047992; Rockland Immunochemicals, Inc. product number 600-401-CW4; and Abbexa product number abx025758

As another example, the MYCT1 inhibiting agent can be an anti-MYCT1 binding partner antibody, wherein the anti-MYCT1 binding partner antibody prevents binding of MYCT1 to its binding partner, such as ZO1 or CKAP4, or prevents activation of its binding partner, such as ZO1 or CKAP4, or downstream signaling.

As another example, the MYCT1 inhibiting agent can be a fusion protein. For example, the fusion protein can be a decoy binding partner for MYCT1. Furthermore, the fusion protein can comprise a mouse or human Fc antibody domain fused to the ectodomain of MYCT1 binding partners.

The three-dimensional structure of MYCT1 is available on Alpha Fold accession number Q8N699. The three-dimensional structure and/or amino acid sequence can be used to design peptide inhibitors or identify small molecule inhibitors of MYCT1. For example, WO 2017/192872, the disclosure of which in incorporated by reference in its entirety, provides methods to identify and rank compounds that interact with a protein of interest. Furthermore, US 20130303387 A1, the disclosure of which in incorporated by reference in its entirety, provides methods to identify peptide binding partners based on the amino acid sequence of interest.

In another embodiment, MYCT1 protein expression may be measured to identify a compound that modulates MYCT1. For example, when MYCT1 protein expression is decreased in the presence of a compound relative to an untreated control, the compound downregulates MYCT1. In a specific embodiment, MYCT1 protein expression may be measured using immunoblot.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present disclsoure, one can use mass spectrometry to look for the level of protein encoded from a target nucleic acid of the disclsoure.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen pre-sent. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immuno-assay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In some embodiments, a MYCT1 inhibitor can be administered using a gene therapy composition. Gene therapies can include inserting a MYCT1 inhibitor with a viral vector. Gene therapies for cancer are rapidly advancing.

There has recently been an improved landscape for gene therapies. For example, in the first quarter of 2019, there were 372 ongoing gene therapy clinical trials (Alliance for Regenerative Medicine, 5/9/19).

Any vector known in the art can be used for the compositions of the disclosure. For example, the vector can be a viral vector selected from retrovirus, lentivirus, herpes, adenovirus, adeno-associated virus (AAV), rabies, Ebola, lentivirus, or hybrids thereof.

| Strategy | | Associated experimental models |
|---|---|---|
| Viral Vectors | | |
| Retroviruses | Retroviruses are RNA viruses transcribing their single-stranded genome into a double-stranded DNA copy, which can integrate into host chromosome | Murine model of MPS VII Canine model of MPS VII |
| Adenoviruses (Ad) | Ad can transfect a variety of quiescent and proliferating cell types from various species and can mediate robust gene expression | Murine model of Pompe, Fabry, Walman diseases, aspartylglucosaminuria and MPS VII |
| Adeno-associated Viruses (AAV) | Recombinant AAV vectors contain no viral DNA and can carry ~4.7 kb of foreign transgenic material. They are replication defective and can replicate only while coinfecting with a helper virus | Murine models of Pompe, Fabry diseases, Aspartylglucosaminuria, Krabbe disease, Metachromatic leukodystrophy, MPS I, MPSII, MPSIIIA, MPSIIIB, MPSIV, MPSVI, MPS VII, CLN1, CLN2, CLN3, CLN5, CLN6 |
| Non-viral vectors | | |
| plasmid DNA (pDNA) | pDNA has many desired characteristics as a gene therapy vector; there are no limits on the size or genetic constitution of DNA, it is relatively inexpensive to supply, and unlike viruses, antibodies are not generated against DNA in normal individuals | Mouse model of Fabry disease |
| RNAi | RNAi is a powerful tool for gene specific silencing that could be useful as an enzyme reduction therapy or means to promote read-through of a premature stop codon | Transgenic mouse strain Mouse models of acute liver failure Mice with hepatitis B virus Fabry mouse |

Gene therapy can allow for the constant delivery of the MYCT1 inhibitor directly to target organs (e.g., endothelial cells) and eliminates the need for weekly infusions. Also, correction of a few cells could lead to the MYCT1 inhibitor being secreted into the circulation and taken up by their neighboring cells (cross-correction), resulting in widespread correction of the biochemical defects. As such, the number of cells that must be modified with a gene transfer vector is relatively low.

Genetic modification can be performed either ex vivo or in vivo. The ex vivo strategy is based on modification of cells in culture and transplantation of the modified cell into patient. Cells that are most commonly considered therapeutic targets for monogenic diseases are stem cells. Advances in collection and isolation of these cells from a variety of sources have promoted autologous gene therapy as a viable option.

The use of endonucleases for targeted genome editing can solve the limitations presented by the usual gene therapy protocols. These enzymes are custom molecular scissors, allowing cutting DNA into well-defined, perfectly specified pieces, in virtually all cell types. Moreover, they can be delivered to the cells by plasm ids that transiently express the nucleases, or by transcribed RNA, avoiding the use of viruses.

(c) MYCT1 Activity

In an embodiment, MYCT1 activity may be measured to identify a compound that modulates MYCT1. MYCT1 interacts with tight junction protein Zona Occludens 1 and regulated Rho GTPase-mediated actin cytoskeleton dynamics, thereby promoting endothelial cell motility. Accordingly, actin cytoskeleton dynamics may be measured as an indication of MYCT1 activity. Actin cytoskeleton dynamics and MYCT1 activity may be measured using methods standard in the art as described below in the Examples. In still another embodiment, tube-like structure formation in Matrigel assay, Boyden chamber tumor chemotaxis assay, wound-closure assay, and cell morphology assays may be measured as an indication of MYCT1 activity.

(d) Components of the Composition

The present disclosure also provides pharmaceutical compositions. The pharmaceutical composition comprises an agent that modulates MYCT1 as described above, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcell-lose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose mono-hydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pre-gelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(e) Administration Forms

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The concentration of a compound of the present disclosure in the fluid pharmaceutical formulations can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. The amount of pharmaceutical composition administered will depend upon the particular therapeutic entity entrapped inside the nanoparticle, the type of nanoparticle being used, and the judgment of the clinician. Generally the amount of pharmaceutical composition administered will be sufficient to deliver a therapeutically effective dose of the particular therapeutic entity.

The quantity of pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, LWW, 2003. Therapeutically effective dosages for various therapeutic entities are well known to those of skill in the art; and according to the present disclosure a therapeutic entity delivered via the pharmaceutical liposome composition of the present invention provides at least the same, or 2-fold, 4-fold, or 10-fold higher activity than the activity obtained by administering the same amount of the therapeutic entity in its routine non-liposome formulation. Typically the dosages for the pharmaceutical composition of the present disclosure range between about 0.005 and about 500 mg of the therapeutic entity per kilogram of body weight, most often, between about 0.1 and about 100 mg therapeutic entity/kg of body weight.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may al-so be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Additional formulations of pharmaceutical delivery systems may be in, for example, Hoover, John E., Remington's Pharmaceutical Sciences, Mack Publishing Co., Easton, Pa. (1975), and Liberman, H. A. and Lachman, L., Eds., Pharmaceutical Dos-age Forms, Marcel Decker, New York, N.Y. (1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. A suitable pharmaceutically acceptable carrier to maintain optimum stability, shelf-life, efficacy, and function of the delivery system would be apparent to one of ordinary skill in the art.

Controlled-release (or sustained-release) preparations may be formulated to ex-tend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising an agent that modulates MYCT1 is encapsulated in a suitable vehicle to either aid in the delivery of the compound to target cells (e.g. endothelial cells), to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles (e.g., protein nanoparticles (NMs) like human serum albumin (HSA), Transferrin (Tf)), liposomes, microemulsions, micelles, dendrimers, and other phospholipid-containing systems. Methods of incorporating compositions into delivery vehicles are known in the art.

In some embodiments, the suitable vehicle used to encapsulate an agent that modulates MYCT1 is further labeled on its surface with one or more targeting ligands. Non-limiting examples of targeting ligands include targeting peptides, which may be natural or synthetic peptides, such as, for example, a targeting antibody or anti-body fragments, targeting glycans (e.g., sugar molecules targeting cell surface receptors), nucleic acids (e.g., single stranded or double stranded DNA, various forms of RNA (e.g., siRNA, and the like), lipids, carboyhydrates (e.g., oligosaccharides, polysaccharides, sugars, and the like), perfluorocarbons, phosphonic acids and bis-phosphonic acids. Preferred targeting ligands include antibodies specifically targeting endothelial cells.

In one alternative embodiment, a liposome delivery vehicle may be utilized. Liposomes, depending upon the embodiment, are suitable for delivery of an agent that modulates MYCT1 in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, an agent that modulates MYCT1 may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylin-ositol (PI), phosphatidylglycerol (PG), diphosphatidylglycerol (DPG), phosphatidylcho-line (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (com-mon name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospho-lipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospho-lipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocya-nine perchloarate, 1,1'-dioleyl-3,3,3',3'-tetramethylindo carbocyanine methanesul-fonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying an agent that modulates MYCT1 may be prepared by any known method of preparing liposomes for drug delivery, such as those de-scribed in the Examples below or as detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of an agent that modulates MYCT1, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. An agent that modulates MYCT1 may be encapsulated in a microemulsion by any method generally known in the art.

In yet another embodiment, an agent that modulates MYCT1 may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

In yet another embodiment, an agent that modulates MYCT1 may be delivered in a biopolymer-based nanoparticles, such as protein nanoparticles. Protein nanoparticles have been actively used as pharmaceutical and functional tools owing to their low toxicity and biodegradability, as exhibited throughout the many studies that have been conducted on the subject. Proteins exhibit unique functions and properties in biological materials and manufacturing fields and can be used as base materials for production of nanoparticles. Owing to their small size, protein nanoparticles can be transmitted through the cell via endocytosis. Protein nanoparticles have several advantages as a drug delivery system, such as biodegradability, stability, surface modification of particles, ease of particle size control, and they have less problems associated with toxicity issues, such as immunogenicity. Protein nanoparticles may be comprised of a variety of different types of proteins, including but not limited to fibroin, human serum albumin, gliadin, gelatin, legumin, 30Kc19, lipoprotein, ferritin and transferrin. Preferred protein nanoparticles include human serum albumin and transferrin nanoparticles. Method for producing protein nanoparticles are known in the art, for example, those described in Hong, Seyoung et al. "Protein-Based Nanoparticles as Drug Delivery Systems." Pharmaceutics vol. 12.7 604. 29 Jun. 2020, doi:10.3390/pharmaceutics12070604, incorporated herein by reference in its entirety. The present disclosure is not particularly limited to a particular production method.

Dosages of composition comprising an agent that modulates MYCT1 can vary between wide limits, depending upon the disease or disorder to be treated, the age and condition of the subject to be treated. In an embodiment where a composition comprising an agent that modulates MYCT1 is contacted with a sample, the concentration of an agent that modulates MYCT1 may be from about 1 μM to about 40 μM. Alter-natively, the concentration of an agent that modulates MYCT1 may be from about 5 μM to about 25 μM. For example, the concentration of an agent that modulates MYCT1 may be about 1, about 2.5 about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 μM. Additionally, the concentration of an agent that modulates MYCT1 may be greater than 40 μM. For example, the concentration of an agent that modulates MYCT1 may be about 40, about 45, about 50, about 55, about 60, about 65, about 70, about 75, about 80, about 85, about 90, about 95, or about 100 μM.

In an embodiment where the composition comprising an agent that modulates MYCT1 is administered to a subject, the dose of an agent that modulates MYCT1 may be from about 0.1 mg/kg to about 500 mg/kg. For example, the dose of an agent that modulates MYCT1 may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of an agent that modulates MYCT1 may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of an agent that modulates MYCT1 may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

As noted above, the agents or compositions described herein can also be used in combination with other therapeutic agents, as described further below. Thus, in addition to the therapies described herein, one may also provide to the subject other therapies known to be efficacious for treatment of the disease, disorder, or condition. In various examples, a method further comprises administering to the patient an additional cancer treatment. In some examples, the additional cancer treatment is chosen from the group comprising surgery, radiotherapy, chemotherapy, toxin therapy, immunotherapy, cryotherapy, gene therapy, and combinations thereof. Examples of anti-angiogenic therapeutic targets useful in accordance with the disclosure include EGF, VEGF, FGF, and matrix remodeling proteins. In various examples, a chemotherapy agent is a drug or drug formulation. Non-limiting examples of drug formulations include polymeric micelle formulations, liposomal formulations, dendrimer formulations, polymer-based nanoparticle formulations, silica-based nanoparticle formulations, nanoscale coordination polymer formulations, nanoscale metal-organic framework formulations, inorganic nanoparticle formulations, and the like.

Various chemotherapy agents (e.g., chemotherapy drugs) can be used. Any FDA approved chemotherapy agent (e.g., chemotherapy drugs) can be used. Combinations of chemotherapy agents may be used.

In some embodiments, the additional drug or therapeutically active agent may be a genotoxic agent (e.g., a DNA-damaging agent or drug). As used herein "genotoxic therapy" refers to a treat of a tumor or cancer which utilizes the destructive properties of the treatment to induce DNA damage into tumor or cancer cells. The treatment is traditionally part of standardized regime. Any damage done to a tumor cancer is passed on to descendent cancer cells as proliferation continues. If this damage is severe enough, it will induce cells to undergo apoptosis. In non-limiting examples, a genotoxic therapy may include γ-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine. clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), vinca alkaloids (vinblastine, vincristine, vinorelbine), and estramustine.

In some embodiments, the additional active agent is a PD-1 or PDL-1 inhibitor. As described herein, Applicant has surprisingly discovered administration of an agent which modulates MYCT1 synergized with anti-PD-1, and optionally VEGF therapy, in a combination therapy to inhibit tumor growth.

Treatment in accord with the methods described herein can be performed prior to, concurrent with, or after conventional treatment modalities for a cancer or tumor.

Dosages of an additional drug or therapeutically active agent can vary between wide limits, depending upon the disease or disorder to be treated, the age and condition of the subject to be treated. In an embodiment where the composition further comprising at least one additional drug or therapeutically active agent is contacted with a sample, the concentration of the at least one additional drug or therapeutically active agent may be from about 0.01 μM to about 10 μM. Alternatively, the concentration of the at least one additional drug or therapeutically active agent may be from about 0.01 μM to about 5 μM. For example, the concentration of the at least one additional drug or therapeutically active agent may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, or about 10 μM. Addition-ally, the concentration of the at least one additional drug or therapeutically active agent be greater than 10 μM. For example, the concentration of the at least one additional agent may be about 10, about 15, about 20, about 25, about 30, about 35, about 40, about 45, about 50, about 55, about 60, about 65, about 70, about 75, about 80, about 85, about 90, about 95, or about 100 μM.

In an embodiment where the composition further comprising at least one additional drug or therapeutically active agent administered to a subject, the dose of the additional drug or therapeutically active agent may be from about 0.1 mg/kg to about 500 mg/kg. For example, the dose of the least one additional drug or therapeutically active agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of the least one additional drug or therapeutically active agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of the least one additional drug or therapeutically active agent may be about 300 mg/kg, about 325 mg/kg, about 350 mg/kg, about 375 mg/kg, about 400 mg/kg, about 425 mg/kg, about 450 mg/kg, about 475 mg/kg, or about 500 mg/kg.

Generally, a safe and effective amount of a composition is administered, for example, that amount that would cause the desired therapeutic effect in a subject while minimizing undesired side effects. In various embodiments, an effective amount of a composition described herein can substantially reduce the growth or spread of cancer in a subject. In some embodiments, an effective amount is an amount capable of treating a cancer or tumor. In some embodiments, an effective amount is an amount capable of treating one or more symptoms associated with a cancer or tumor.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the com-position at levels lower than those required to achieve the desired therapeutic effect and to gradually increase the dosage until the desired effect is achieved. If desired, the effective daily dose may be divided into multiple doses for purposes of administration.

Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of a composition as disclosed herein can occur as a single event or over a time course of treatment. For example, a composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The disclosure is not limited to dosing intervals that are spaced equally in time, but encompass doses at non-equal intervals, such as a priming schedule consisting of administration at 1 day, 4 days, 7 days, and 25 days, just to provide a non-limiting example.

A dosing schedule of, for example, once/week, twice/week, three times/week, four times/week, five times/week, six times/week, seven times/week, once every two weeks, once every three weeks, once every four weeks, once every five weeks, and the like, is available for the disclosure. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

As one aspect of the present disclosure contemplates the treatment of the disease/conditions with the compounds of the disclosure, the disclosure further relates to pharmaceutical compositions in kit form. When the composition of the disclosure is a part of a combination therapy with a secondary therapeutic agent, the kit may comprise two separate pharmaceutical compositions: one of compound of the present disclosure, and another of a second therapeutic agent. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The present disclosure encompasses pharmaceutical compositions comprising agents as disclosed above, so as to facilitate administration and promote stability of the active agent. For example, a compound of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). For the purposes of the aspects and embodiments of the invention, the subject may be a human or any other animal.

III. Methods

Among the various aspects of the present disclosure is the provision of methods for modulating MYCT1. An aspect of the present disclosure provides for a method of regulating tumor angiogenesis (anti-angiogenesis, Myct1-targeted vascular control) and/or immunostimulation, which inhibit tumor growth, in a subject. In some embodiments, the method comprises administering an MYCT1 modulating agent (e.g., MYCT1 inhibiting agent) to a subject having a cancer or tumor. In some embodiments, the effective amount of an MYCT1 modulating agent can be an amount effective to substantially block or inhibit MYCT1 expression and/or activity in endothelial cells (ECs); reduce angiogenesis; facilitate HEV formation; enhance robust CTL infiltration; or promote inflammatory M1 macrophage polarization. In some embodiments, the subject has upregulated MYCT1 in ECs prior to administration of the MYCT1 modulating agent. Suitable compositions, administration forms, dosing and dosing schedules for use in the methods of the present disclosure are disclosed herein, for instance those described in Section I which is incorporated by reference into this section. In some embodiments, the method further comprises administering an immunotherapy (e.g., anti-PD-1) and, optionally, VEGF targeted therapy. In some embodiments, the amount of an MYCT1 modulating agent and immunotherapy is an amount effective to reduce or prevent exhaustion of the infiltrating cytotoxic T lymphocytes (CTLs). In some embodiments, the MYCT1 modulating agent is a small molecule inhibitor of MYCT1, an MYCT1 blocking antibody, MYCT1 antagonist, or MYCT1 shRNA/siRNA. In some embodiments, the subject has improved antitumor drug delivery and enhanced antitumor immunity. In some embodiments, the subject has high endothelial venule formation and an antitumor immune environment, leading to a restricted tumor progression. In some embodiments, the MYCT1 modulating agent targets MYCT1 in endothelial cells (ECs). In some embodiments, blocking MYCT1 endothelium promotes an immunostimulatory microenvironment by enhancing CTLs infiltration and preventing CTLs apoptosis; contributes to an immunostimulatory microenvironment; leads to an anti-tumor microenvironment; and/or promotes endothelial regulation of tumor immunity. In some embodiments, combined vascular and immune control provides synergistic anti-tumor activity. In another aspect, the disclosure provides a composition as disclosed herein for use in vitro, in vivo, or ex vivo.

The present disclosure provides compounds and pharmaceutical compositions comprising the same which are useful for treating a cancer or tumor in a subject. In some embodiments, administration of a composition of the present disclosure results in reduced or prevented tumor growth. In some embodiments, administration of a composition of the present disclosure results in reduced EC motility by disrupting MYCT1 interaction with ZO1 and CKAP4 and modulating Rho GTPases and actin cytoskeleton. In some embodiments, administration of a composition of the present disclosure results deficient tumor vasculature. In some embodiments, administration of a composition of the present disclosure results in increased EC HEVs. In some embodiments, administration of a composition of the present disclosure results in increased CTLs infiltration. In some embodiments, administration of a composition of the present disclosure results in increased EC HEVs. In some embodiments, administration of a composition of the present disclosure results in increased anti-tumor macrophage polarization (e.g. increasing the M1-macrophage-to-M2 macrophage ratio). In some embodiments, administration of a composition of the present disclosure results in the down-regulation of the expression of Fas ligand in ECs. Thus, in some embodiments, the methods of the present disclosure are useful for reducing tumor or cancer progression or prolonging the survival of subject having a cancer or tumor. The present disclosure provides that combined vascular and immune control provide a synergistic anti-tumor activity. For example, targeting Myct1 improves the response to anti-PD1 therapy in treatment-responsive and -refractory tumors and combined Myct1 and VEGF targeting with anti-PD1 treatment produced a superior tumor control, suggesting synergy between Myct1 and VEGF pathways.

Therefore, in one aspect, the methods and compositions comprising them, can be administered to an individual to treat a tumor or cancer. In another aspect, the methods and compositions comprising them, can be administered to an individual to prevent or reduce vascular network formation in a target tissue. The tissue can be undesirable tissue that has arisen due to transformation, such as a tumor, cancer. As used herein, the term "cancer" includes a wide variety of malignant neoplasms. These can be caused by viral infection, naturally occurring transformation, or exposure to environmental agents.

In some examples, the methods can be useful for treating a cancer or tumor in a subject. The term "treating a cancer or tumor" includes, but is not limited to, preventing or reducing the development of a cancer or tumor, reducing the symptoms of cancer or tumor, suppressing or inhibiting the growth of an established cancer or tumor, preventing metastasis and/or invasion of an existing cancer or tumor, promoting or inducing regression of the cancer or tumor, inhibiting or suppressing the proliferation of cancerous or tumor cells, reducing angiogenesis or increasing the amount of apoptotic cancer or tumor cells, thereby treating cancer or a tumor.

Non-limiting examples of cancers or tumors that may be treated with a method of the disclosure may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (child-hood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, or Wilms tumor (childhood).

In one embodiment, this method generally includes the steps of providing a composition as described herein; administering the composition to a subject or cell (e.g. an endothelial cell).

In some embodiments, the present disclosure provides a methods for treating tumors or cancer cells with increased risk of angiogenesis. In some embodiments, the disclosure provides a method of treating a cancer or tumor by administering a composition of the disclosure sequentially or simultaneously with another cancer therapy. When administered sequentially the additional agent may be administered before or after the compound of the disclosure. In a preferred embodiment, the additional agent is an immune check point blockade and optionally a anti-VEGF therapy.

The term "effective amount", as used herein, means an amount that leads to measurable effect, e.g., cancer cell death. The effective amount may be determined by using the methods known in the art and/or described in further detail in the examples.

In other aspects, compositions of the disclosure may be delivered to a cancer cell in vitro. A cancer cell may be a cancer cell line cultured in vitro. In some alternatives of the embodiments, a cancer cell line may be a primary cell line that is not yet described. Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the MM cell lines MM.1S, H929, and RPMI, osteosarcoma cell lines 143B, CAL-72, G-292, HOS, KHOS, MG-63, Saos-2, or U-2 OS; the prostate cancer cell lines DU145, PC3 or Lncap; the breast cancer cell lines MCF-7, MDA-MB-438 or T47D; the myeloid leukemia cell line THP-1, the glioblastoma cell line U87; the neuroblastoma cell line SHSYSY; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8, HCT 116, NCI-H716, NCI-H747, NCI-H508, NCI-H498, COLO 320HSR, SNU-C2A, LS 180, LS 174T, MOLT-4, LS513, LS1034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B or SW480; B16-F10, RAW264.7, the F8 cell line, or the pancreatic carcinoma cell line Panc1.

Generally, the methods as described herein comprise administration of a therapeutically effective amount of a nanoparticle composition of the disclosure to a subject. The methods described herein are generally performed on a subject in need thereof. A subject may be a rodent, a human, a livestock animal, a companion animal, or a zoo-logical animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

As shown in the below examples, the level of MYCT1 can be used as a predictive marker of the angiogenic status of a subject and therefore useful for making treatment decisions for subjects who can benefit from certain therapies (e.g. anti-angiogenics). For example, the level MYCT1 of a candidate subject can be compared with a reference value.

A reference value may represent the same level of MYCT1 in a control subject or represent the level MYCT1 in a control population. In some examples, the same level MYCT1 in a control subject or a control population may be determined by the same method as used for determining the level MYCT1 in the candidate subject. In some in-stances, the control subject or control population may be a subject having cancer or a tumor or a subject population having cancer or a tumor who is responsive to treatment. In other instances, the control subject or control population may be a subject having cancer or a tumor or a subject population having cancer or a tumor who is non-responsive to treatment. Alternatively, the control subject or control population may refer to a healthy subject or healthy subject population. In a preferred embodiment, the control subject or control population is of the same species (e.g., a human subject or human subject population) as the candidate subject. As used herein, assessing "responsiveness" or "non-responsiveness" to a therapy refers to the determination of the likelihood of a subject for responding or not responding to the therapeutic agent. For example, a responsive subject will have a therapeutic effect as a result of administration of an agent. In some embodiments, a therapeutic effect includes to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and re-mission (whether partial or total), or can also mean prolonging survival as compared to expected survival if not receiving treatment or a non-responsive subject or population.

It is to be understood that the methods provided herein do not require that a reference value be measured every time a candidate subject is tested. Rather, in some embodiments, it is contemplated that the reference value can be obtained and recorded and that any test level can be compared to such a reference level. The reference level may be a single-cutoff value or a range of values.

By comparing level of MYCT1 in a candidate subject as disclosed herein with a reference value as also described herein, the subject can be identified as responsive or likely to be responsive or as not responsive or not likely to be responsive to a therapy based on the assessing.

For example, when the reference value represents the level of MYCT1 who are responsive to a therapy, derivation from such a reference value would indicate non-responsiveness to the therapy. In another embodiment, when the reference value rep-resents the level of MYCT1 who are responsive to a genotoxic therapy, about the same level of phosphorylation of MYCT1 in a candidate subject would indicate responsive-ness to the therapy.

Alternatively, when the reference value represents the level MYCT1 who are non-responsive to a therapy, derivation from such a reference value would indicate responsiveness to the therapy. In another embodiment, when the reference value represents the level of MYCT1 who are non-responsive to a therapy, about the same level of MYCT1 in a candidate subject would indicate non-responsiveness to the therapy.

In some instances, derivation means that the level of MYCT1 (e.g., represented by a value) of a candidate subject is elevated or reduced as relative to a reference value, for example, by at least 5%, 10%, 20%, 30%, 40%, 50%, 60%, 70%, 80%, 90%, 100%, 150%, 200%, 300%, 400%, 500% or more above or below the reference value.

Thus, the present disclosure provides a method for assessing responsiveness to a therapy or detecting the angiogenic status of a cancer or tumor in a subject having a cancer or tumor. In one embodiment, a method for assessing responsiveness to a therapy or detecting the angiogenic status may comprises (a) providing a biological sample obtained from a subject and measuring, in the cancer cell or tumor cell or endothelial cell of the sample, the level of MYCT1; and (b) determining the subjects responsive-ness to the therapy or angiogenic status when the measured MYCT1 level deviates from a reference value.

MYCT1 levels may be used in various mathematical operations to assess responsiveness or angiogenic status. For instance, MYCT1 values can be used in various statistical models (e.g., linear regressions, LME curves, LOESS curves, etc.) in conjunction with other known biomarkers. Selection of measurements and choice of mathematical operations may be optimized to maximize specificity of the method. For instance, diagnostic accuracy may be evaluated by area under the ROC curve and in some embodiments, an ROC AUC value of 0.7 or greater is set as a threshold (e.g., 0.7, 0.75, 0.8, 0.85, 0.9, 0.95, etc.).

Methods for measuring MYCT1 levels are described in Section I and incorporated into this section by reference.

The disclosure provides a method (also referred to herein as a "screening assay") for identifying modulators, i.e., candidate or test compounds or agents (e.g., peptides, peptidomimetics, small molecules or other drugs) which downregulate MYCT1, for example, MYCT1 nucleic acid expression, MYCT1 protein expression or MYCT1 activity. A modulator of MYCT1 may directly or indirectly downregulate MYCT1.

Screening assays may also be used to identify molecules that modulate MYCT1 nucleic acid expression, MYCT1 protein expression or MYCT1 activity. For example, decrease in MYCT1 expression or activity reduces angiogenesis, facilitate HEV formation, enhance robust CTL infiltration, and promote inflammatory M1 macrophage polarization. Accordingly, angiogenesis, HEV formation, CTL infiltration, M1 polarization and EC migration may be measured as an indication of MYCT1 activity or expression. Various assays for measuring the activity are described in the Examples below.

In one embodiment, the invention provides assays for screening candidate or test compounds which bind to or modulate the activity or expression of MYCT1. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or on phage (Scott and Smith (1990) Science 249:386¬390; Devlin (1990) Science 249:404-406; Cwirla et al. (1990) Proc. Natl. Acad. Sci. 87:6378-6382; and Felici (1991) J. Mol. Biol. 222:301-310).

In one embodiment, an assay is one in which cells are contacted with a test compound and the ability of the test compound to downregulate MYCT1 is determined. Determining the ability of the test compound to downregulate MYCT1 may be accomplished, for example, by detecting MYCT1 protein expression. Numerous methods for detecting protein are known in the art and are contemplated according to the invention, see Section I. Specifically, an immunoblot may be used to detect MYCT1 protein. Another method for determining the ability of the test compound to downregulate MYCT1 may be accomplished by a reporter assay for MYCT1 expression. For example, MYCT1 protein expression may be fused to a reporter protein such that MYCT1 expression may be monitored by measuring the expression of the reporter protein. By way of example, reporter proteins may include a fluorescent protein, luciferase, alkaline phosphatase, beta-galactosidase, beta-lactamase, horseradish peroxidase, and variants thereof. In another embodiment, determining the ability of the test compound to downregulate MYCT1 may be accomplished, for example, by detecting MYCT1 nucleic acid expression. Methods of measuring nucleic acid expression are known in the art, see Section I. Specifically, MYCT1 mRNA may be detected via standard methods.

In another embodiment, an assay is one in which MYCT1 is contacted with a test compound and the ability of the test compound to bind to MYCT1 is determined. Determining the ability of the test compound to bind to MYCT1 may be accomplished, for example, by coupling the test compound with a radioisotope or enzymatic label such that binding of the test compound to MYCT1 may be determined by detecting the labeled com-pound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In yet another embodiment, an assay of the present invention is a cell-free assay comprising contacting MYCT1 with a test compound and determining the ability of the test compound to bind to MYCT1. Binding of the test compound to MYCT1 may be determined either directly or indirectly. In one embodiment, a competitive binding assay includes contacting MYCT1 with a compound known to bind MYCT1 to form an assay mixture, contacting the assay mixture with a test compound, and determining the ability of the test compound to interact with MYCT1, wherein determining the ability of the test compound to interact with MYCT1 comprises determining the ability of the test compound to preferentially bind to MYCT1 compared to the known binding compound.

In another embodiment, an assay is a cell-free assay comprising contacting MYCT1 with a test compound and determining the ability of the test compound to modulate (e.g., stimulate or inhibit) the activity of MYCT1. Determining the ability of the test compound to modulate the activity of MYCT1 can be accomplished, for example, by determining the ability of MYCT1 to bind to or interact with a MYCT1 target molecule (e.g. ZO-1). In an alternative embodiment, determining the ability of the test compound to modulate the activity of MYCT1 can be accomplished by determining the ability of MYCT1 to further modulate a MYCT1 target molecule. As used herein, a "target molecule" is a molecule with which MYCT1 binds or interacts in nature.

In another embodiment, modulators of MYCT1 expression are identified in a method in which a cell is contacted with a candidate compound and the expression of the MYCT1 promoter, mRNA or protein in the cell is determined. The level of expression of MYCT1 mRNA or protein in the presence of the candidate compound is compared to the level of expression of MYCT1 mRNA or protein in the absence of the candidate compound. The candidate compound can then be identified as a modulator of MYCT1 expression based on this comparison. For example, when expression of MYCT1 mRNA or protein is greater (statistically significantly greater) in the presence of the candidate compound than in its absence, the candidate compound is identified as a stimulator of MYCT1 mRNA or protein expression. Alternatively, when expression of MYCT1 mRNA or protein is less (statistically significantly less) in the presence of the candidate compound than in its absence, the candidate compound is identified as an inhibitor of MYCT1 mRNA or protein expression. The level of MYCT1 mRNA or protein expression in the cells can be determined by methods described herein for detecting MYCT1 mRNA or protein. The activity of the MYCT1 promoter can be assayed by linking the MYCT1 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

This disclosure further pertains to novel agents identified by the above-described screening assays and uses thereof for treatments as described herein.

As various changes could be made in the above-described materials and methods without departing from the scope of the invention, it is intended that all matter contained in the above description and in the examples given below, shall be interpreted as illustrative and not in a limiting sense.

VI. Clinical Trials

Another aspect of the present disclosure is a method for enrolling a subject into a clinical trial, in particular a clinical trial for immune checkpoint inhibitors and/or anti-angiogenesis agents, provided all other criteria for the clinical trial have been met. In one embodiment, a method for a method for enrolling a subject into a clinical trial may comprise (a) providing a biological sample obtained from a subject and measuring, in a cancer cell or tumor cell or endothelial cell of the sample, the level of MYCT1; and (b) enrolling the subjects the subject into a clinical trial when the measured MYCT1 level deviates from a reference value.

The design of clinical trials for cancer or tumor therapies can be greatly aided by the methods disclosed herein. Many clinical trials are designed to test the efficacy of immune checkpoint inhibitors and/or anti-angiogenesis agents. As discussed herein, the efficacy of these various agents can be improved by administering the agents to subjects that have certain levels of MYCT1, as measured by methods disclosed herein and illustrated. Accordingly, measuring MYCT1 levels as described herein prior to enrolling a subject in a clinical trial, in particular into a treatment arm of a clinical trial, may result in smaller trials and/or improved outcomes. In some instances, methods described herein may be developed and used as a companion diagnostic for a therapeutic agent.

In each of the above embodiments, a subject may be enrolled into a treatment arm of the clinical trial. The "treatment" is defined in Section III. Subjects enrolled in the treatment arm of a clinical trial may be administered a pharmaceutical composition. In some embodiments, a pharmaceutical composition may comprise a immune checkpoint inhibitors and/or anti-angiogenesis agents. In some embodiments, a pharmaceutical composition may comprise a MYCT1 inhibitor as described herein.

VII. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to MYCT1 modulating agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject. A reference value can be used in place of a control or reference sample, which was previously obtained from a healthy subject or a group of healthy subjects. A control sample or a reference sample can also be a sample with a known amount of a detectable compound or a spiked sample. A control sample or a reference sample can also be from a genotoxic treatment responsive subject or population. A control sample or a reference sample can also be from a genotoxic treatment non-responsive subject or population.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Dual Role of Endothelial Myct1 in Tumor Angiogenesis and Tumor Immunity Tumor vessels are irregular, tortuous, and leaky. These malfunctioning vessels lead to a hypoxic environment where tumors thrive and eventually metastasize to secondary sites. Following the initial report on the vasculature-dependent nature of solid tumor progression 50 years ago, the notion of preventing new vessel formation as a way to treat cancers generated substantial interest. Extensive research has identified several critical pro-angiogenic factors, including vascular endothelial growth factors (VEGFs) and fibroblast growth factors, as potential targets for anti-angiogenic therapies. However, despite impressive potential shown in pre-clinical studies, anti-angiogenic strategies like anti-VEGF treatment generated only modest clinical outcomes in cancer patients, possibly due to temporary vascular normalization, angiogenic adaptive responses, and/or acquired resistance by the tumor. Pro-angiogenic factors like VEGFs are also required for physiological vascular maintenance, contributing to the related toxicities and poor clinical outcomes of anti-VEGF therapies. As such, new targets are required to develop anti-angiogenic approaches that may empower cancer management.

Immunotherapies such as immune checkpoint blockers and adoptive immune cell transfer have revolutionized the field of oncotherapy by enabling the regression and long-term control of previously incurable and aggressive tumors. However, they fail to produce clinical benefits in 50%-80% of treated patients, suggesting that further studies focusing on the functional crosstalk between different immunotherapeutic approaches and the constituents of the tumor microenvironment are needed. Accumulating data show that the abnormal nature of the tumor vessels also profoundly influences the outcome of different immunotherapeutic strategies. Moreover, several recent preclinical studies have shown that a combination of immune checkpoint blockade with anti-angiogenic treatment could result in improved outcomes. Better understanding of the crosstalk between the angiogenic determinants and immunotherapies may lead to more effective clinical strategies.

The present Example identified Myct1 as a direct target of ETS transcription factor ETV2, a critical factor for vascular development, regeneration, and tumor angiogenesis. Although Myct1 is dispensable for vascular development and homeostasis, it is crucial for tumor progression through the regulation of tumor angiogenesis and tumor immunity. Remarkably, Myct1 inhibition in combination with anti-PD1 led to dramatic tumor regression. These findings establish a critical role for Myct1 in modulating the tumor vasculature and remodeling of immune constituents of the tumor microenvironment.

Results

Figure 1B:
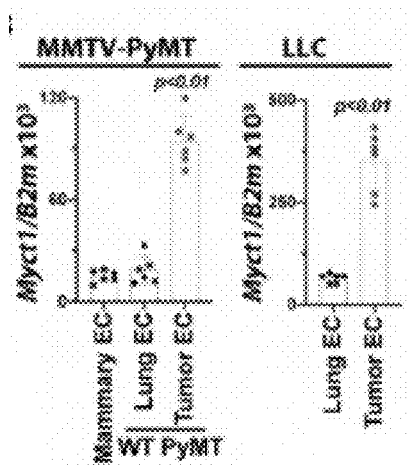

Myct1 is a direct target of ETV2 and is an angiogenic regulator gene: The expression profiles of more than 8,000 human cancer patients (from thirteen different cancer types) from The Cancer Genome Atlas (TCGA) database were first analyzed. A list of the top 20 potential angiogenesis regulatory genes were generated (Table 1), whose expression correlates with "seed genes" that are well characterized in angiogenesis and endothelial cell (EC) biology. Comparing this list with the ETS transcription factor ETV2 transcriptional target genes, Flt1, Myct1, Ptprb, and S1pr1 were found as top potential angiogenesis regulatory genes downstream of ETV2. Unlike the other genes, Myct1 has never been implicated in angiogenesis; hence, the present example identified Myct1 as a potential angiogenic gene for the first time. Consistent with this idea, it was found that Myct1 expression was mostly restricted to ECs. Next, a gene set variation analysis was performed with TCGA-derived patient datasets using a signature of genes upregulated during angiogenesis to generate an "Angiogenic score" for every patient. We found that MYCT1 expression was significantly ($p<0.05$) correlated with the "Angiogenic score" in all cancers analyzed (FIG. 1A). Moreover, increased Myct1 expression was found in the tumor-ECs compared to the non-tumor-ECs in mouse models (FIG. 1B). In line with this, analysis of a single-cell RNA sequencing dataset on the heterogeneous mouse tumor stromal population revealed that Myct1 expression is observed exclusively in the tumor-ECs. Additionally, in the same dataset, compared to the EC population from a healthy heart, the tumor-EC population had a higher number of cells that expressed Myct1. Together, these observations suggest that Myct1 plays a role in tumor angiogenesis/vasculature in both human cancers and mouse tumors.

TABLE 1

Top 20 regulators of angiogenesis identified by their correlated expression with seed genes

| Rank | Gene Symbol | Full name | PCC |
|---|---|---|---|
| 1 | GPR4 | G Protein-Coupled Receptor 4 | 0.92 |
| 2 | LDB2 | LIM Domain Binding 2 | 0.91 |
| 3 | CXorf36 | Chromosome X open reading frame 36 | 0.91 |
| 4 | ADGRL4 | Adhesion G Protein-Coupled Receptor L4 | 0.91 |
| 5 | FLT1 | Fms Related Tyrosine Kinase 1 | 0.9 |
| 6 | CLEC14A | C-Type Lectin Domain Containing 14A | 0.9 |
| 7 | ECSCR | Endothelial Cell Surface Expressed Chemotaxis and Apoptosis Regulator | 0.9 |
| 8 | RP11-389C8.2 | RP11-389C8.2 | 0.9 |
| 9 | ESAM | Endothelial Cell Adhesion Molecule | 0.9 |
| 10 | MYCT1 | Myc Target 1 | 0.9 |
| 11 | CD93 | Cluster of Differentiation 93 | 0.9 |
| 12 | PLVAP | Plasmalemma Vesicle Associated Protein | 0.89 |
| 13 | S1PR1 | Sphingosine-1-Phosphate Receptor 1 | 0.89 |
| 14 | PTPRB | Protein Tyrosine Phosphatase Receptor Type B | 0.89 |
| 15 | ARHGEF15 | Rho Guanine Nucleotide Exchange Factor 15 | 0.89 |
| 16 | GIMAP8 | GTPase, IMAP Family Member 8 | 0.89 |
| 17 | PCDH12 | Protocadherin 12 | 0.88 |
| 18 | EXOC3L2 | Exocyst complex component 3-like 2 | 0.88 |
| 19 | ZNF366 | Zinc Finger Protein 366 | 0.88 |
| 20 | GIMAP6 | GTPase, IMAP Family Member 6 | 0.88 |

Figure 1C:
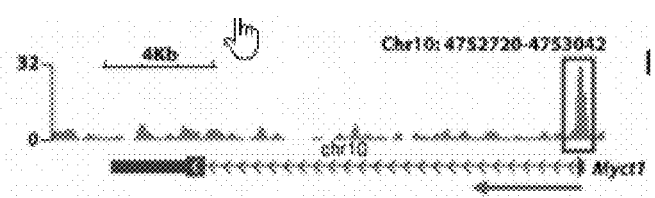
Figure 1D:
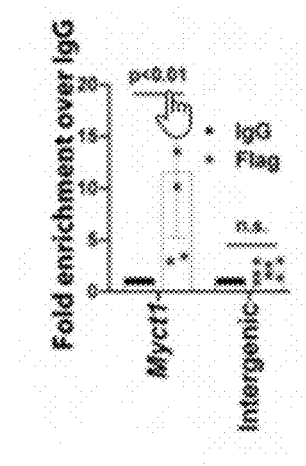
Figure 1E:
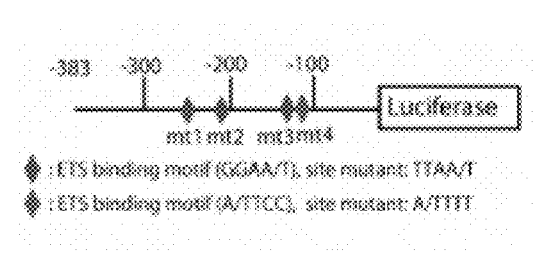
Figure 1F:
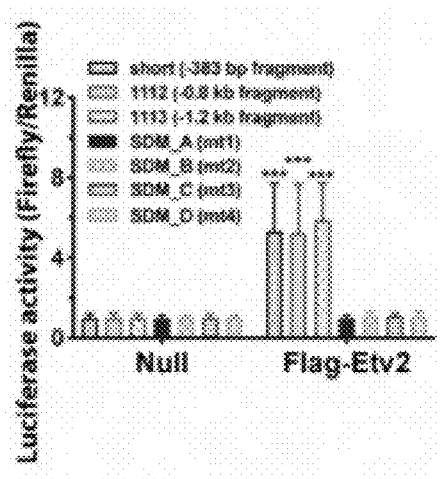
Figure 1G:
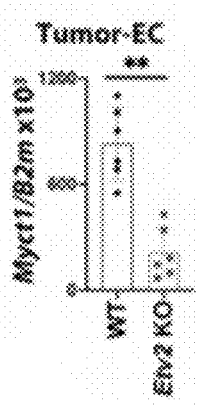
Figure 1H:
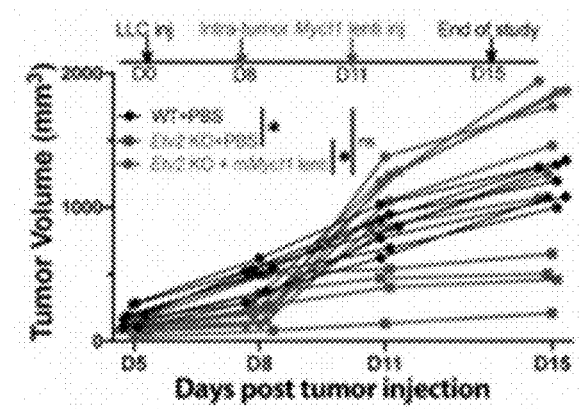
Figure 1I:
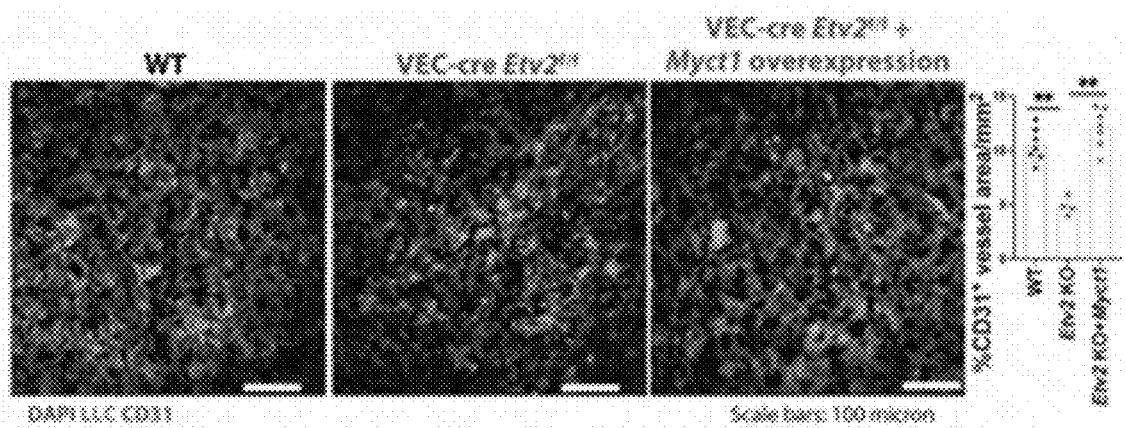

One potential ETV2 binding site in the Myct1 promoter region was identified by analyzing previously published ETV2 ChIP-Seq data (FIG. 1C). This binding was validated by ChIP-qPCR (FIG. 1D). Only ETV2 and no other ETS transcription factors, such as FLI1 and ERG, activated different luciferase constructs made with varying sizes of the Myct1 promoter region, all containing the ETS binding motif. Mutations of the ETS binding motifs reduced luciferase activity, implying that these sites were critical for ETV2 binding (FIGS. 1E-1F). In vitro overexpression of Myct1 rescued the tube-like structure formation, sprouting, and migration defects observed in the Etv2 deficient ECs. Finally, Myct1 was downregulated in the tumor-ECs of the Etv2 conditional knockout (KO) mice (FIG. 1G) and intra-tumoral lentiviral Myct1 expression rescued impaired tumor growth and angiogenesis observed in Etv2 deficiency (FIG. 1H and FIG. 1I). In this experiment, intra-tumoral lentiviral Myct1 injection resulted in enforced expression of Myct1 in ECs, as well as in tumor cells and hematopoietic cells. To assess whether the observed phenotypic rescue is from non-endothelial enforced Myct1 expression, Myct1 overexpressing Lewis lung carcinoma (LLC) tumor cells were generated and found that there is no growth advantage for these Myct1 overexpressing tumor cells in wild-type (WT) mice. Additionally, tumor growth patterns in our bone-marrow chimeric mice suggest that Myct1 expression in hematopoietic cells does not contribute to tumor growth (as described below; see, e.g., FIG. 2G-2J). Together, these results suggested that Myct1 was a direct target gene of ETV2 that regulates the angiogenic functionalities of ECs.

Figure 1J:
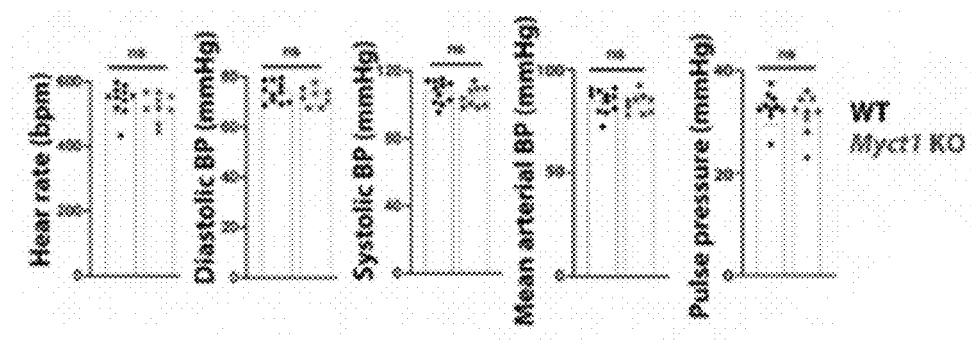
Figure 1K:
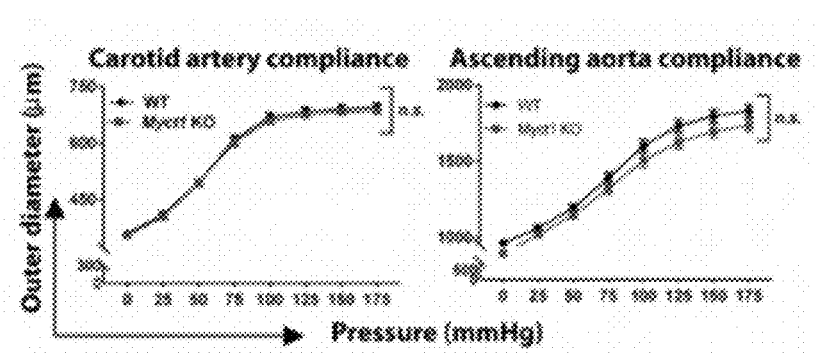
Figure 1L:
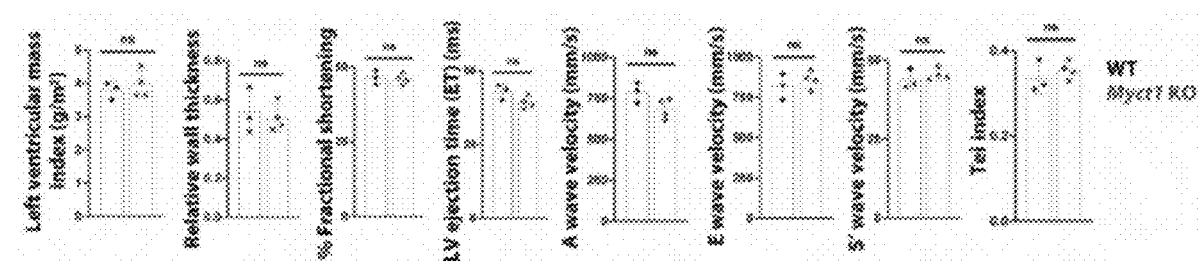

Myct1 is dispensable for vascular development and homeostasis in mice and zebrafish: Myct1−/− (Myct1 KO) mice were generated by utilizing the CRISPR/CAS9 technology. Briefly, gRNA were designed to target the first exon of the Myct1 gene and injected together with Cas9 mRNA into fertilized eggs (Details in the Materials and Method section). By crossing the candidate knockout founder to wild-type mice, heterozygous (Myct1+/−) offspring were generated and obtained Myct1 KO mice from brother-sister matings. Myct1 expression was undetected in the ECs isolated from the lungs of the KO animals, confirming the efficient deletion of the gene. Myct1 KO mice appeared normal and exhibited histologically regular vasculature in different organ beds. Vital cardiovascular parameters (FIG. 1J), compliance profiles of the ascending aorta and carotid artery (FIG. 1K), and clinically relevant cardiac functions (FIG. 1L) were similar between the Myct1 KO and littermate control mice. Similarly, myct1 zebrafish morphants showed minimal defects in vascular development. Together, these observations suggested that Myct1 was dispensable for vascular development, maintenance, and homeostatic functions.

Myct1 is required for efficient tumor growth and tumor vasculature in multiple mouse models: Since high Myct1 expression is observed in tumor ECs, whether Myct1 deficiency has any impact on tumor growth was determined by employing five different (one transgenic, three subcutaneous transplantation, and one orthotopic transplantation) mouse models of cancer. For the transgenic model, MMTV-PyMT; Myct1.sup.−/−mice were developed as a spontaneous breast cancer model and tracked the development and progression of the tumor in the mammary gland. For transplantation models, Lewis lung carcinoma (LLC-GFP), B16F10 melanoma, and 1956 sarcoma tumor cells and orthotopically transplanted PyMT-BO1 mammary tumor cells were subcutaneously transplanted to the mammary fat pad as described previously. Compared to WT mice, Myct1 KO mice showed retarded tumor growth in all five of the tumor models; the growth restricted tumors had reduced counts of tumor vessels, which had better pericyte coverages (FIGS. 2A-2F). Moreover, Myct1 KO mice exhibited subsided intra-tumoral hypoxia, improved vascular perfusion, and reduced vascular leakage. These data demonstrated that although not essential for vascular development and maintenance, Myct1 deficiency led to reduced tumor growth and normalization of tumor vessels.

Figure 2A:
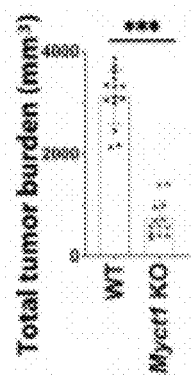
FIG. 2A-2J shows endothelial Myct1 is required for tumor growth and angiogenesis in mice.
Figure 2B:
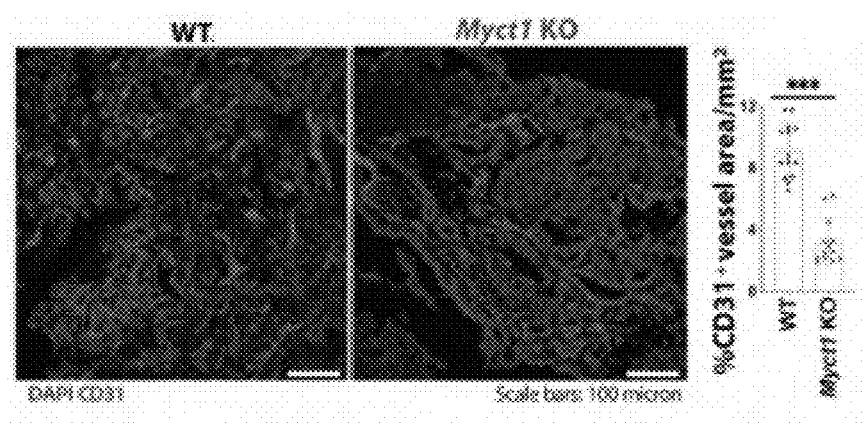
Figure 2C:
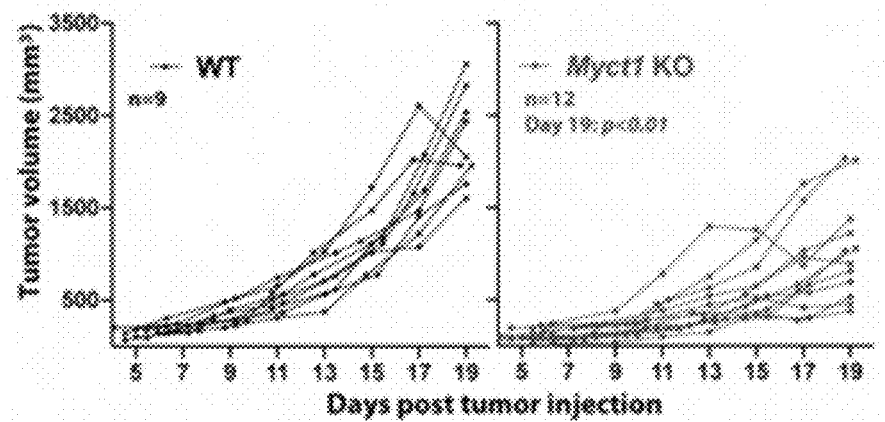
Figure 2D:
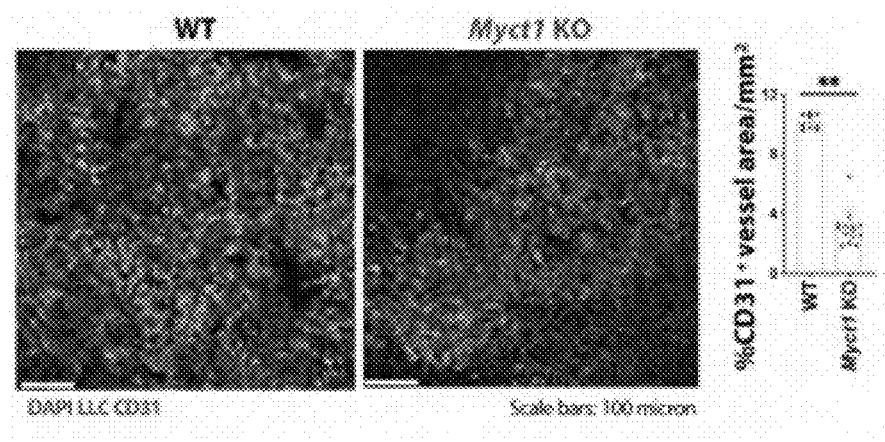
Figure 2E:
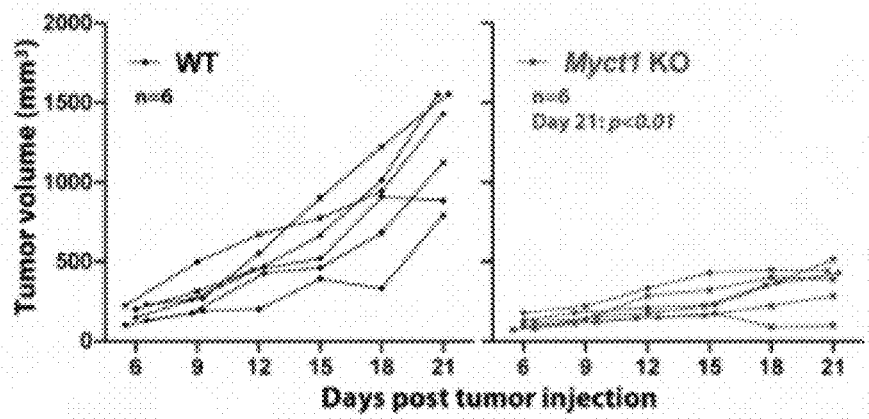
Figure 2F:
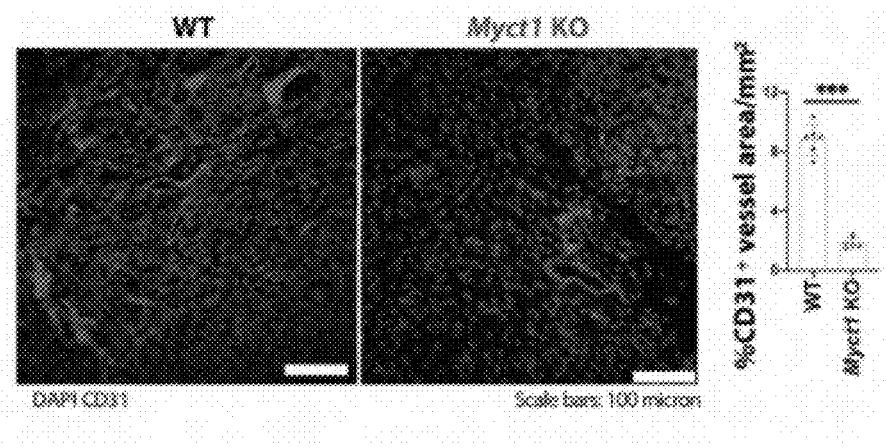
Figure 2G:
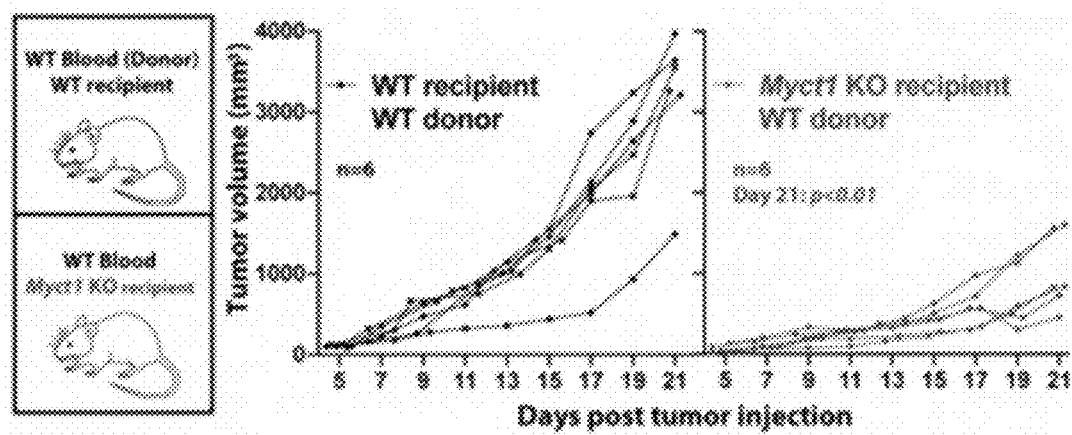
Figure 2H:
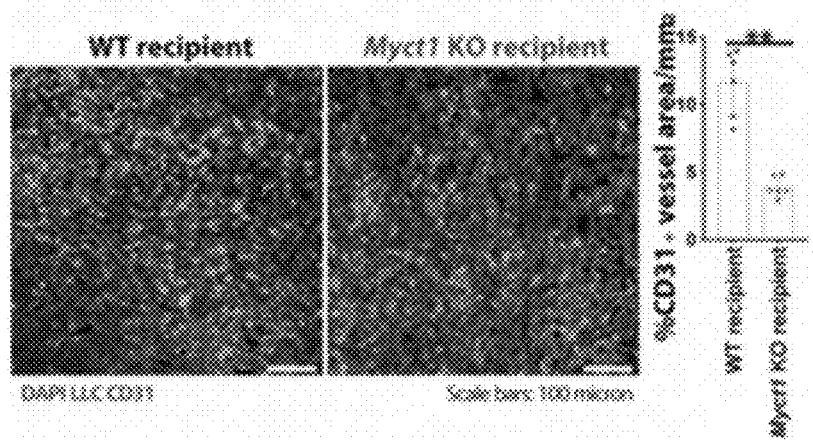
Figure 2I:
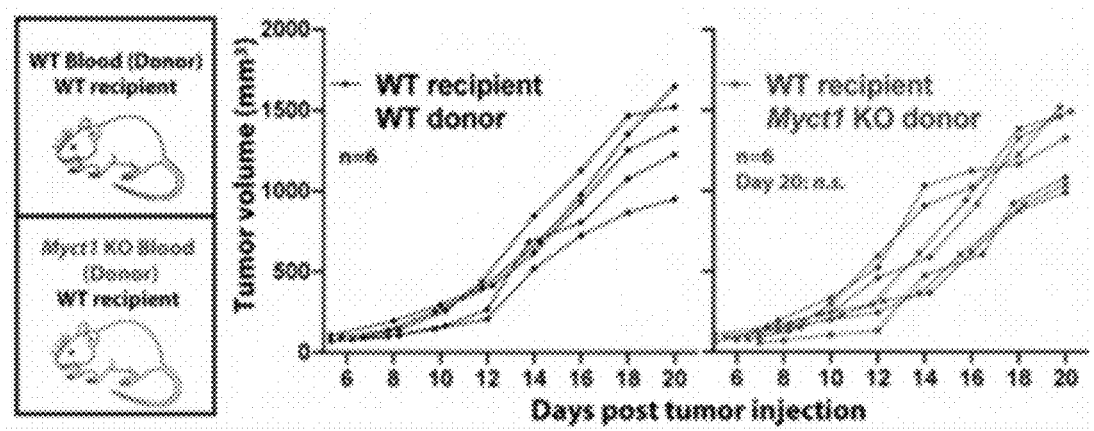
Figure 2J:
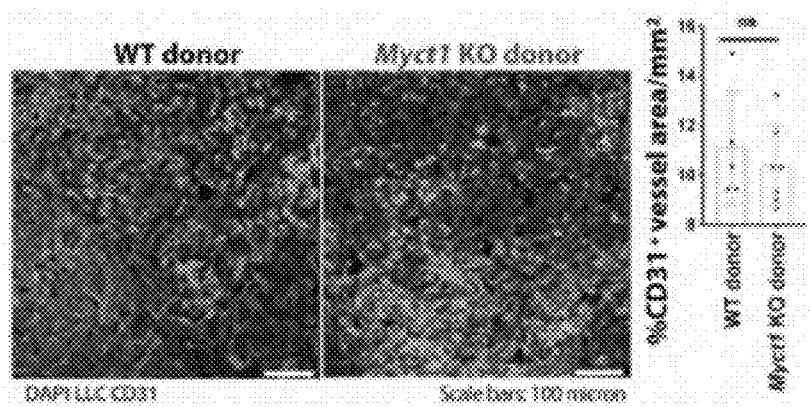

Endothelial Myct1 is critical for tumor growth in mice: While Myct1 expression was mostly restricted to the ECs, Myct1 was also expressed in hematopoietic stem and progenitor cells. To evaluate whether the observed growth restrictive phenotype is dependent on EC-specific Myct1, two distinct bone marrow chimeras were generated: 'WT hematopoietic/Myct1 KO background' and 'Myct1 KO hematopoietic/WT background' mice. 'WT hematopoietic/ Myct1 KO background' chimeric mice exhibited impaired tumor growth and vascular network formation, a phenotype similar to Myct1 KO mice (FIG. 2G-2H). However, 'Myct1 KO hematopoietic/WT background' chimeric mice exhibited tumor growth comparable to WT mice (FIG. 2I-2J). Moreover, endothelial-specific Myct1 deletion in mice (Cdh5-cre Myct1$^{f/f}$) recapitulated the global Myct1 KO phenotype of retarded tumor growth and reduced angiogenesis, together suggesting that hematopoietic Myct1 expression was dispensable for tumor progression.

To investigate whether Myct1 plays any role(s) in tumor cells, Myct1 expression in the tumor cell lines utilized earlier in the present study were assessed and found that Myct1 expression was not detectable. To investigate whether synthetic Myct1 expression in tumor cells contributes to growth, LLC tumor cells were genetically modified with either Myct1 shRNA or Myct1 overexpressing lentivirus and the PyMT-BO1 tumor cells with Myct1 siRNA. It was found that either Myct1 siRNA or shRNA treatment or enforced expression of Myct1 in the tumor cells did not play any role in tumor growth kinetics. Additionally, tumor explants from neither the WT nor the Myct1 KO MMTV-PyMT mice exhibited any growth defects in the WT recipient mice. However, explants from both types of mice showed tumor growth defects in the Myct1 KO recipient mice. Together these data suggest that Myct1 function in the observed phenotype is tumor cell independent. a human fibroblast cell line (BJ-5ta) was also modified that does not express MYCT1 by treating with MYCT1 shRNA or enforcing the expression of MYCT1 with lentivirus. It was found that neither of the modifications impacted the growth kinetics and angiogenic sprouting of the fibroblasts. Collectively, these data suggested an endothelial-specific role of Myct1 in tumor growth and angiogenesis.

Myct1 is Also Required for Vascular Regeneration in Mice:

To investigate whether Myct1 is required exclusively for tumor angiogenesis, a mouse hindlimb ischemia injury model was utilized as described previously. It was found that following the injury, Myct1 KO mice had a lower blood perfusion recovery and neovascularization of the injured area compared to WT mice, suggesting that the Myct1 requirement is not exclusive to tumor angiogenesis—other forms of neovascularization also require Myct1.

Figure 3A:
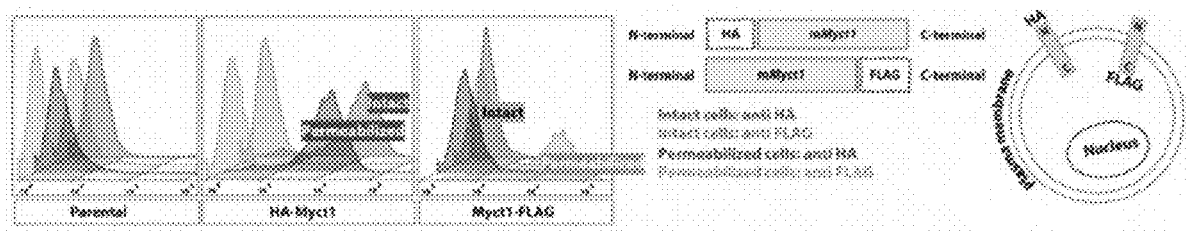
FIG. 3A-3L show membrane-localized MYCT1 regulates endothelial actin cytoskeleton dynamics in the angiogenic environment.

MYCT1 Interacts with ZO1 and Regulates EC Motility Through Actin Cytoskeleton In Vitro:

Because very little is known about the cellular functions of Myct1, the subcellular localization of MYCT1 in ECs was first assessed. To this end, mouse cardiac EC lines (MCEC) expressing either N-terminal HA-tagged or C-terminal FLAG-tagged mouse Myct1 were generated (FIG. 3A). Flow cytometric analysis revealed that in the intact cells, whereas the anti-HA antibody recognized HA-MYCT1, the anti-FLAG antibody did not recognize MYCT1-FLAG. On the contrary, both the antibodies recognized HA-MYCT1 and MYCT1-FLAG in permeabilized cells (FIG. 3A). Immunofluorescence with anti-HA and anti-FLAG antibodies showed that MYCT1 is indeed present at the plasma membrane, as well as in the cytoplasm, where it was found colocalized mainly with GM130+ and GIANTIN+ Golgi apparatus. Collectively, these results demonstrated that MYCT1 is a membrane-spanning protein with an extracellular N-terminal and an intracellular C-terminal, consistent with a previous structural prediction based on bioinformatic analysis of MYCT1.

Figure 3B:
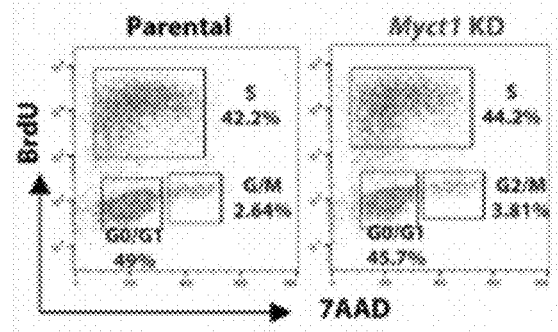
Figure 3C:
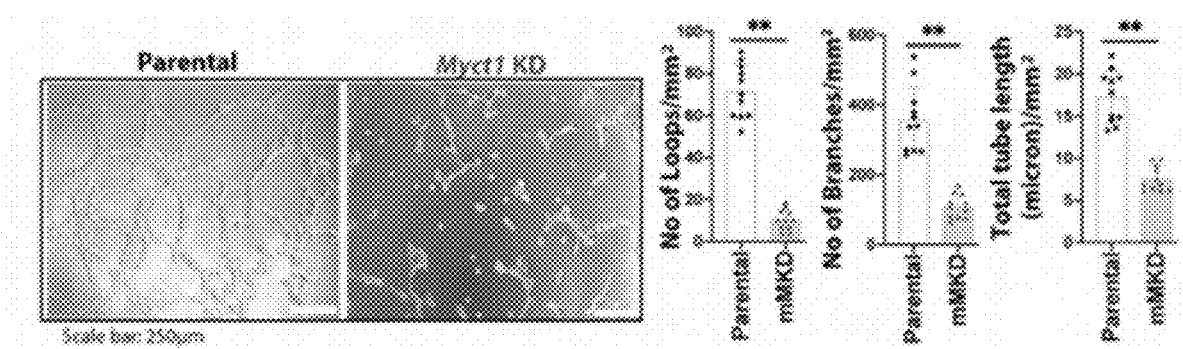
Figure 3D:
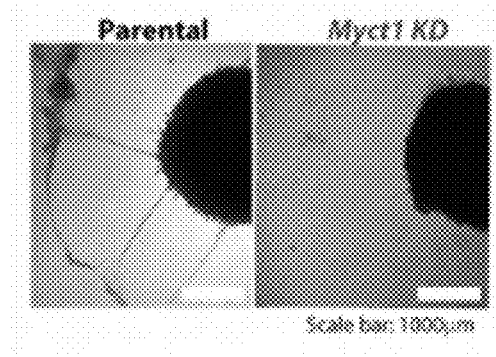
Figure 3E:
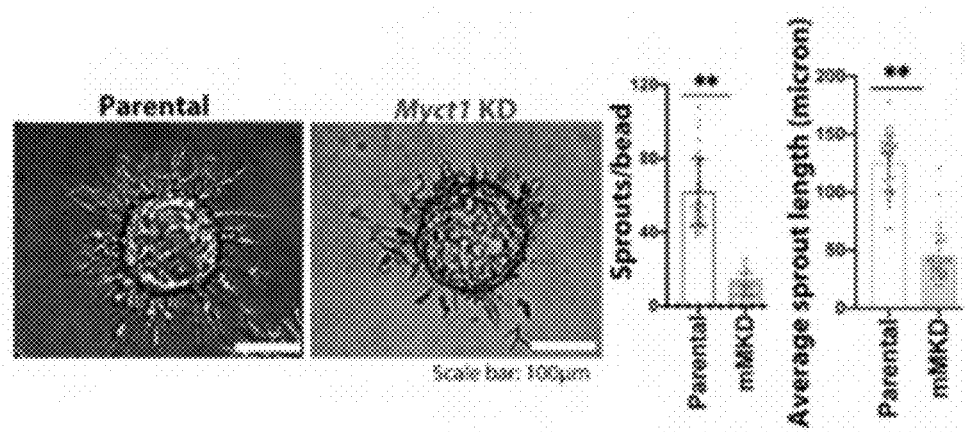
Figure 3F:
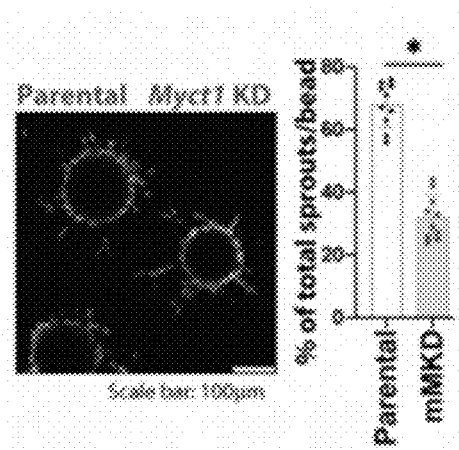
Figure 3G:
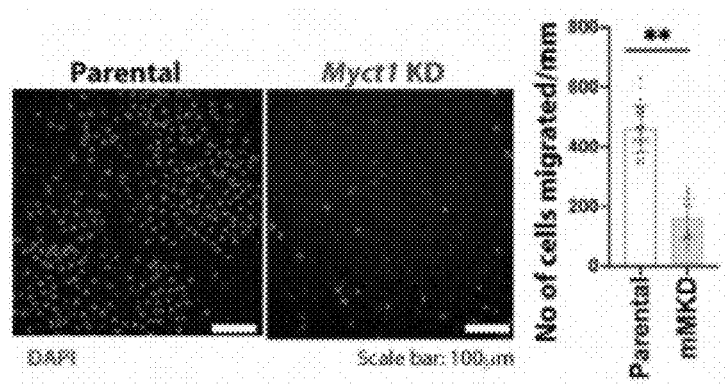
Figure 3H:
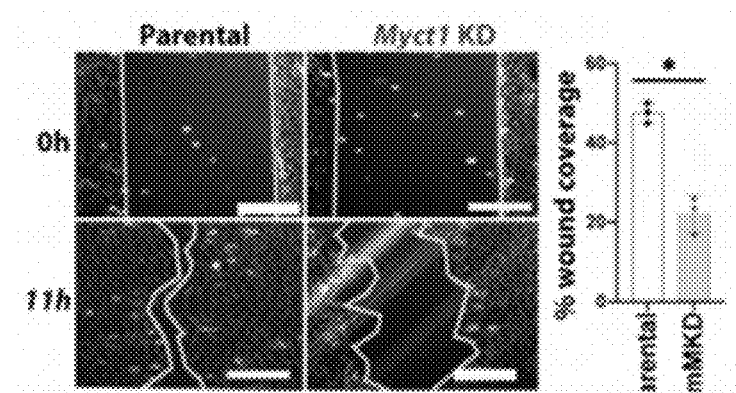

We next developed Myct1 knockdown (KD) MCEC cells and assessed EC functionalities. We did not observe any proliferative or maintenance disparity compared to the parental cells, as supported by the similar cell cycle distribution between parental and Myct1 KD cells (FIG. 3B). However, Myct1 KD MCEC cells showed defects in tube-like structure formation in the Matrigel assay (FIG. 3C) and tumor spheroid/EC co-culture assay (FIG. 3D). Myct1 KD MCEC cells also displayed defects in sprout formation on the fibrin gel matrix (FIG. 3E-3F). Additionally, Myct1 KD MCEC cells lost their migratory characteristics, as shown in the Boyden chamber tumor-chemotaxis assay (FIG. 3G) and wound-closure assay (FIG. 3H). Importantly, parental cells utilized in these studies did not show any difference compared to the sham shRNA or empty vector control transduced cells. Together, these findings suggested that while Myct1 is not required for the steady-state maintenance of ECs, it is essential for ECs responses in the angiogenic environment.

Figure 3I:
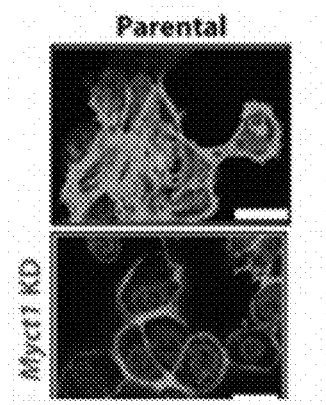

Different phases of angiogenesis, such as sprouting, migration, and tube-like-structure formation, require EC alignment and directional movement in response to angiogenic cues. To understand why Myct1 KD ECs show defective migratory properties in the angiogenic environment, the downstream effectors of Myct1 in regulating EC motility were assessed. Specifically, RNA was extracted from sprouts formed in the fibrin gel matrix (see FIG. 3E) and performed a PCR array for genes that regulate cellular motility. Genes that regulate actin cytoskeleton dynamics and cell adhesion turnover such as Capn2, Actin, Actinr2 and 3, Cfl1, Rdx, Myl12a, and Wasf1 were downregulated in the Myct1 KD MCEC sprouts. Rhoa and Rhoc, which are required for the formation of actin stress fibers, cell retraction following protrusions, and overall movement, were also downregulated, implying that Rho GTPase signaling is defective in Myct1 KD cells. Intriguingly, elements of RAC signaling, such as Rac1, Arhgef7, and Stat3, were upregulated in the Myct1 KD sprouts, suggesting an unbalanced hyperactivation of RAC signaling, which regulates the formation of leading-edge protrusion during cell movement. Consistent with this idea, Myct1 KD MCEC cells in both 2D culture (FIG. 3I) and scattered 3D tube structures formed virtually no stress fibers, which are critical for cellular contractility-relaxation, adhesion, and migration. Notably, Arhgdia, a Rho GDP dissociation inhibitor that keeps Rho GTPase proteins in their inactive forms, was highly upregulated in the Myct1 KD MCEC sprouts, again implying a dysregulated Rho GTPase signaling. Congruent with this idea, Arhgdia knockdown moderately rescued the Myct1 KD MCEC phenotype.

Figure 3J:
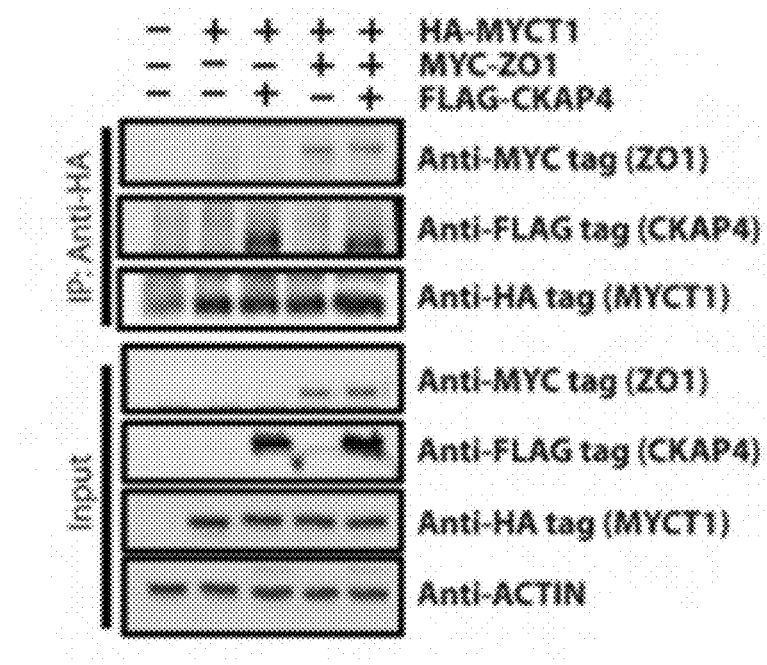
Figure 3K:
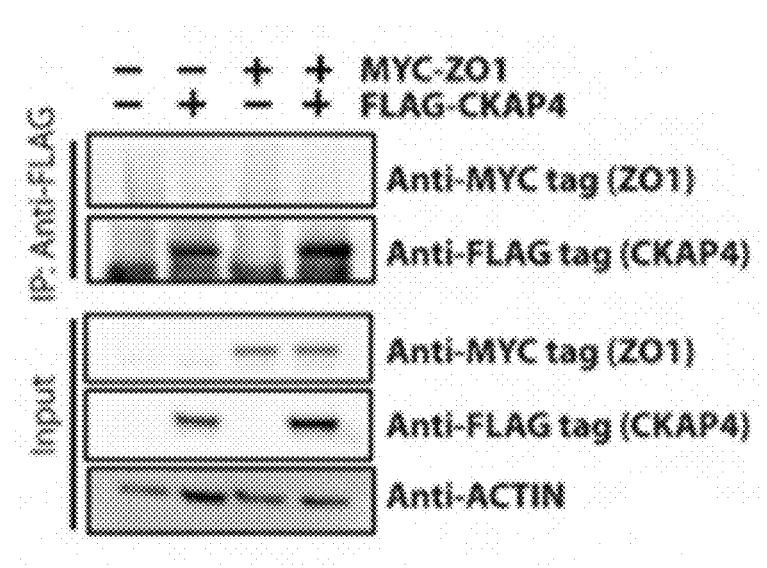
Figure 3L:
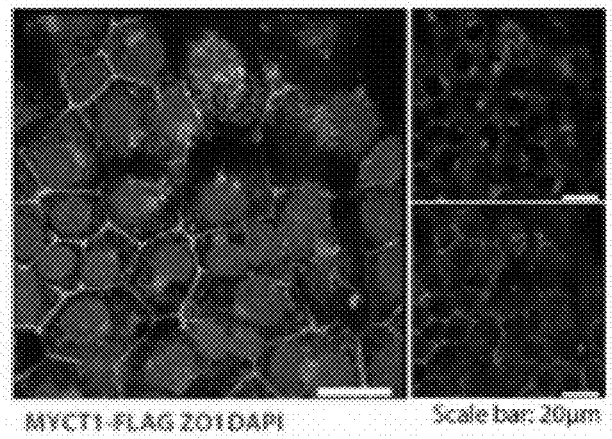
Figure 3M:
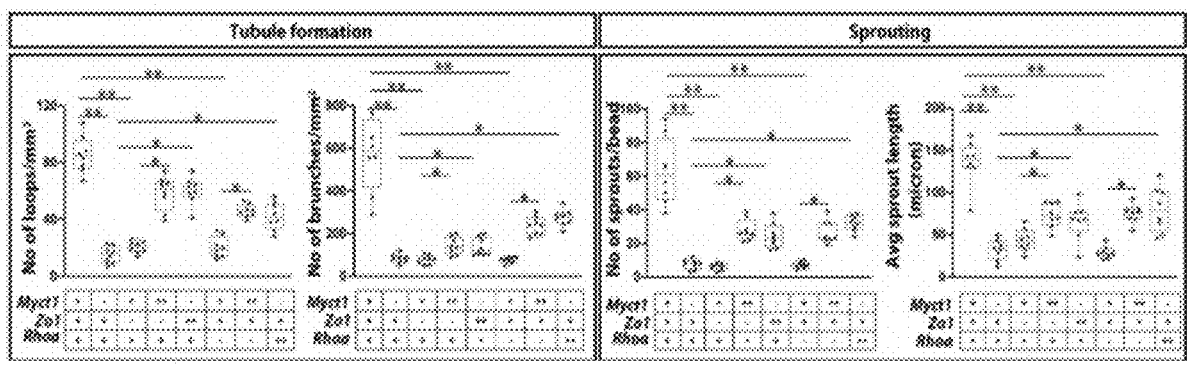
FIG. 3M shows quantifications from the Matrigel tube formation assay (left) and fibrin gel sprouting assay (right) with different combinations of Myct1, Zo1, and Rhoa KD and overexpressing MCEC cells. "+", "++", and "−" denotes parental, overexpression, and knockdown cells, respectively. n≥6 independent observations per group. Data is presented as mean with SD from one of two biological replicates. Statistical significance was analyzed by One-way ANOVA with Tukey's multiple comparison test; *p<0.05, **p<0.01.

Next, MYCT1 binding partners were characterized by taking a target-directed approach. Using proteomics analysis, ZO1 (Zona Occludens 1, also known as tight junction protein 1) and CKAP4 were identified as potential candidates for binding MYCT1. ZO1 and CKAP4 were confirmed as binding partners of MYCT1 by utilizing co-immunoprecipitation followed by western blot. Intriguingly, it was found that, although ZO1 and CKAP4 do not bind directly to each other, MYCT1 binds both of them together in a complex (FIG. 3J-3K). Immunofluorescence also supported the interaction between MYCT1 and ZO1 by co-localization (FIG. 3L). A similar binding pattern between MYCT1 and CKAP4 in HEK293T cells was also reported in a previous study. Since ZO1 plays a critical role in EC functions such as barrier formation, tension, and migration and RHOA regulates endothelial tight junction maintenance and barrier formation in close association with ZO1, it was investigated whether there is a functional interplay between MYCT1, ZO1, and RHOA through a series of combined knockdown and overexpression of these genes in MCEC cells. It was found that similar to Myct1 KD, downregulation of either Zo1 or Rhoa led to impaired sprouting and tube formation of ECs in the angiogenic environment. These angiogenic defects of Myct1 deficient ECs were partially rescued by Zo1 overexpression; likewise, Zo1 deficiency phenotypes were partially rescued by Myct1 overexpression (FIG. 3M). We observed similar, although to a somewhat lesser extent, interplay between Myct1 and Rhoa as well (FIG. 3M), suggesting that MYCT1-ZO1 complex works in close functional association with RHOA to control the actin cytoskeleton. Intriguingly, both the parental and Myct1 KD cells responded similarly to VEGF in a fibrin gel sprouting assay, suggesting that Myct1 might regulate ECs angiogenic functionalities independently of VEGF. Collectively, these data suggested that MYCT1 regulates directional movement of ECs in the angiogenic environment through controlling actin cytoskeleton dynamics.

Figure 4A:
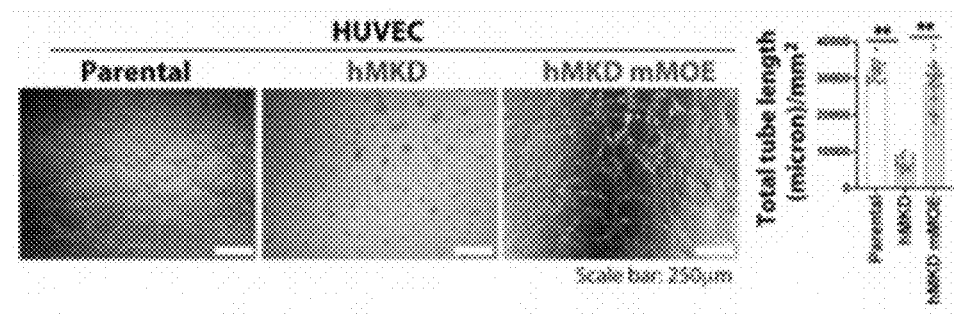
FIG. 4A-4H show Endothelial MYCT1 function is evolutionarily conserved between human and mouse.
Figure 4B:
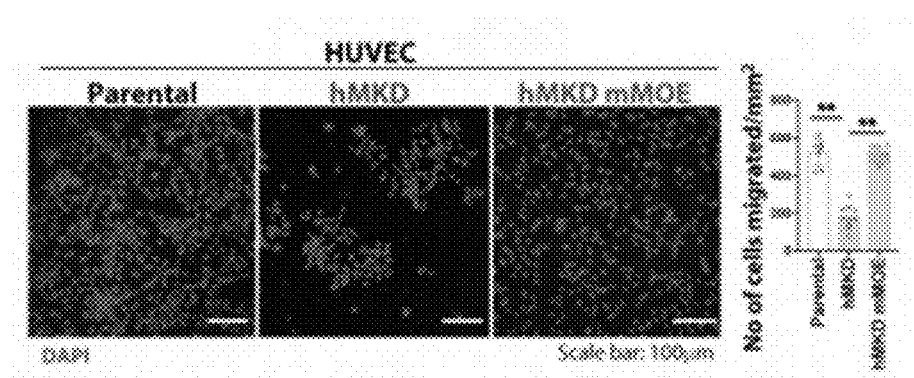
Figure 4C:
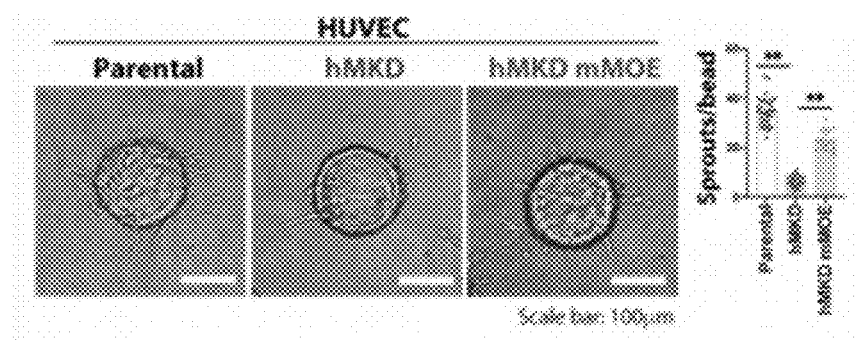
Figure 4D:
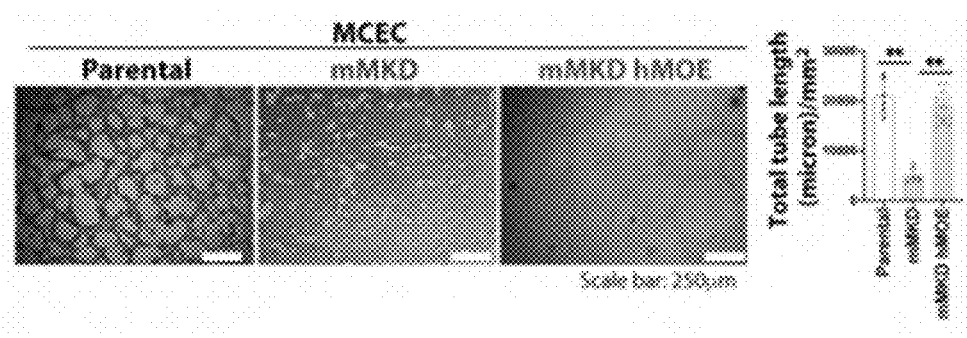
Figure 4E:
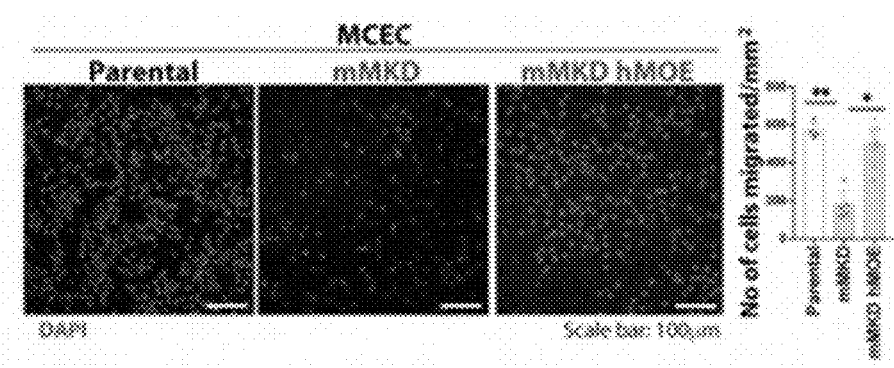
Figure 4F:
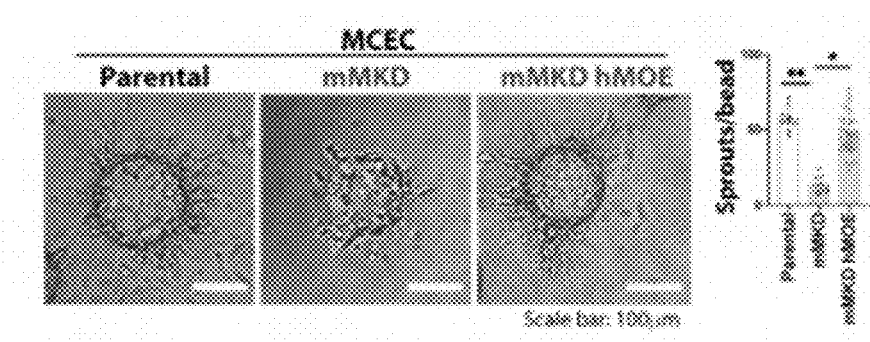
Figure 4G:
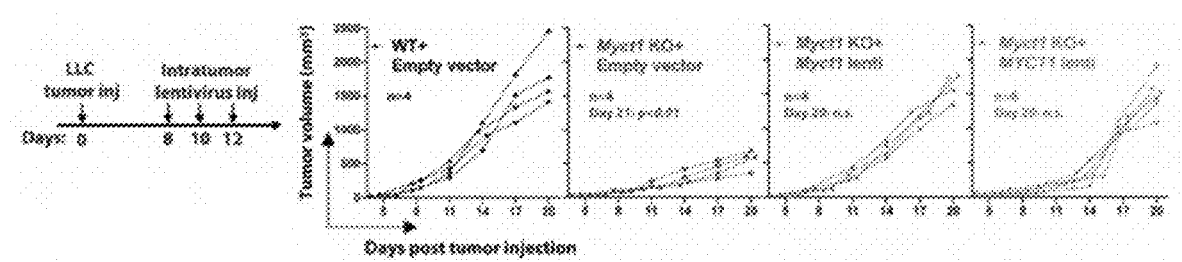
Figure 4H:
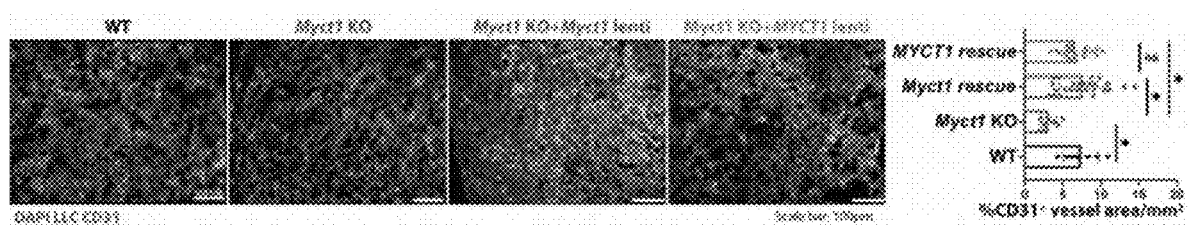

Endothelial MYCT1 Function is Evolutionarily Conserved Between Human and Mouse:

Mouse MYCT1 protein shares an 85% sequence identity with the human MYCT1 protein. To determine whether MYCT1 function is conserved between human and mouse, human MYCT1 in HUVEC (HUVEC hMKD) cells were knocked-down. Similar to the Myct1 KD MCEC cells, HUVEC hMKD cells displayed severely impaired tube-like-structure generation, sprout formation, and migration capabilities (FIG. 4A-4C). Importantly, enforced expression of mouse Myct1 almost completely rescued the human MYCT1 KD defects and vice-versa in vitro (FIG. 4A-4F). Moreover, both the mouse and human MYCT1 overexpression rescued the impaired tumor growth and reduced angiogenesis phenotype of the Myct1 KO mice in a subcutaneous tumor transplantation model (FIG. 4G-4H). Again, although the lentiviral treatment induced Myct1 over expression in tumor cells and hematopoietic cells along with the ECs, as we described above, the observed rescue of the tumor phenotype in this experiment is most likely from endothelial Myct1. Together, these data suggest that the MYCT1 function in EC is conserved between human and mouse.

Figure 5A:
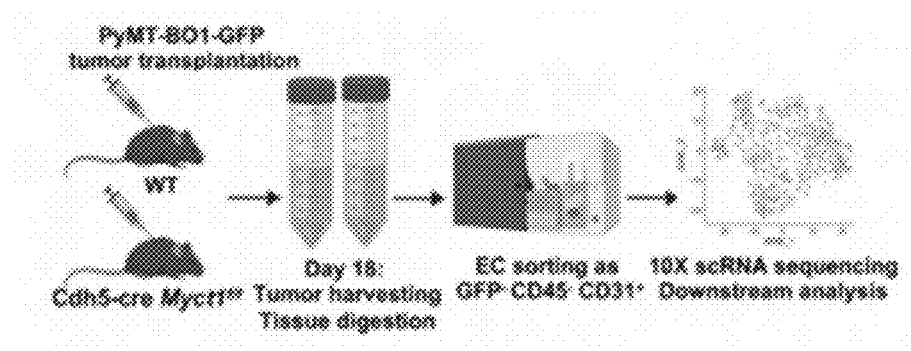
FIG. 5A-5P show single cell RNA sequencing of tumor endothelium from WT and Cdh5-cre Myct1f/f mice signifies Myct1 functions in tumor angiogenesis.
Figure 5B:
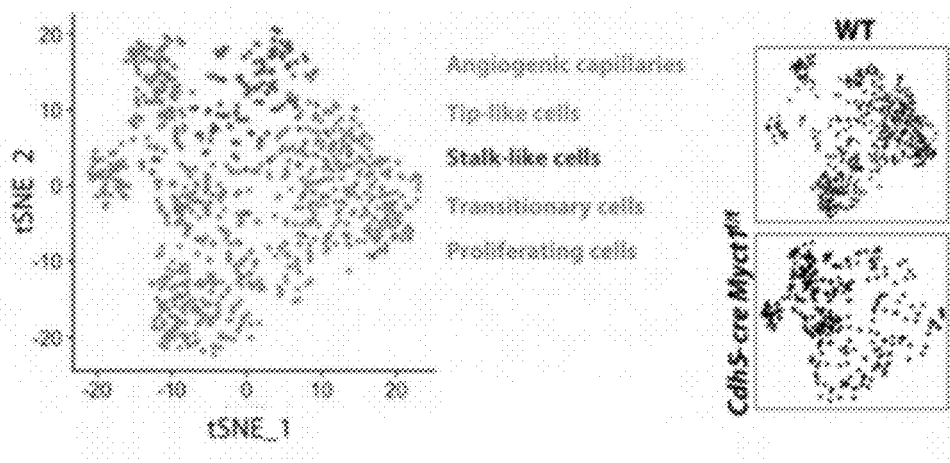
FIG. 5B show tSNE projection color-coded for 995 endothelial cells sorted from tumor mass (PYMT-BO1 orthotopic transplantation tumor model). (Right) tSNE projection of endothelial cells grouped for different genotypes.
Figure 5C:
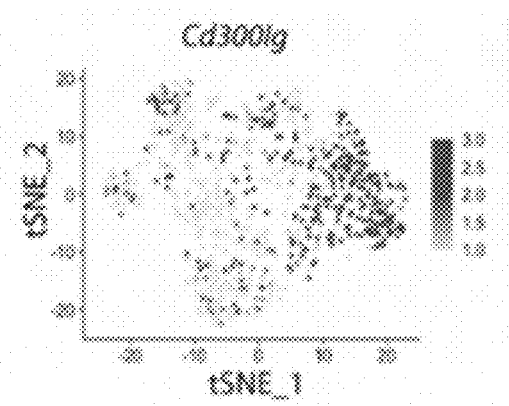
FIG. 5C show Feature plot showing Cd300lg expression pattern.
Figure 5D:
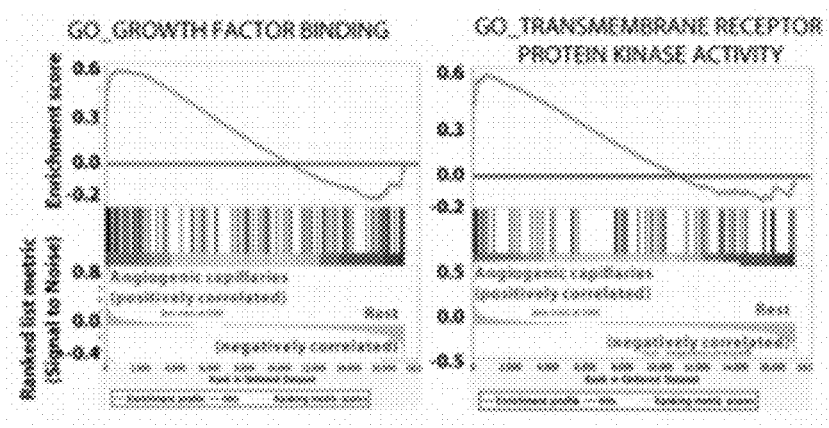
FIG. 5D show gene set enrichment analysis depicting enriched molecular pathways.
Figure 5E:
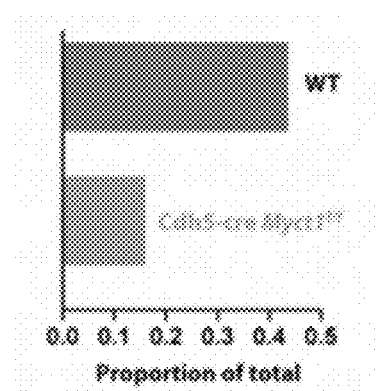
FIG. 5E show normalized proportion of cells in the angiogenic capillaries sub-cluster of the tumor endothelial cells from WT and Cdh5-cre Myct1f/f mice derived by analyzing the SCTtransform data (normalized).
Figure 5F:
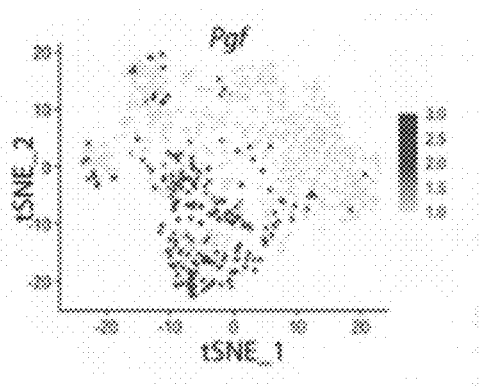
FIG. 5F show feature plot showing Pgf expression pattern.
Figure 5G:
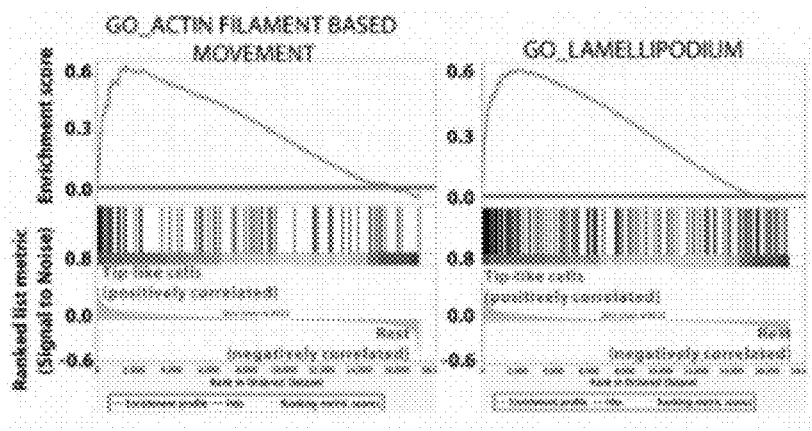
FIG. 5G show gene set enrichment analysis depicting enriched molecular pathways.
Figure 5H:
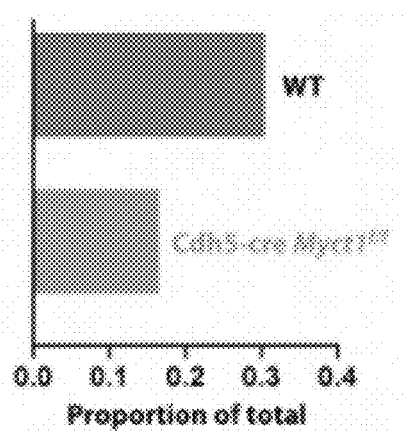
FIG. 5H show normalized proportion of cells (H) in the Tip-like cells sub-cluster of the tumor endothelial cells from WT and Cdh5-cre Myct1f/f mice derived by analyzing the SCTtransform data (normalized).
Figure 5I:
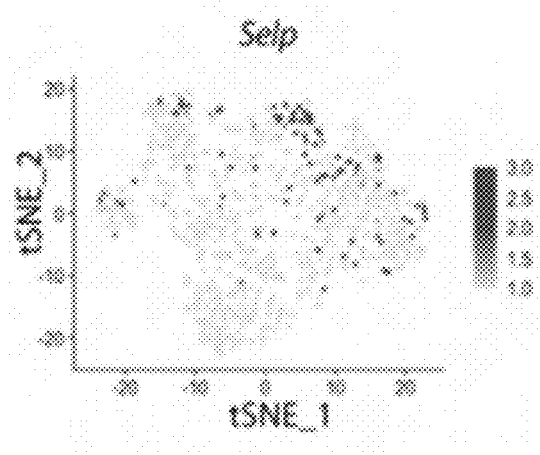
FIG. 5I show feature plot showing Selp expression pattern (I).
Figure 5J:
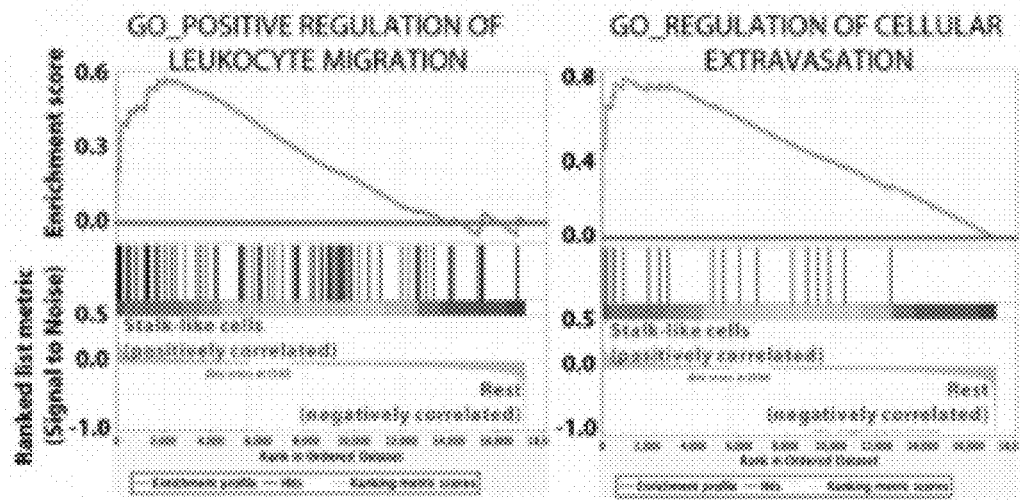
FIG. 5J show gene set enrichment analysis depicting enriched molecular pathways.
Figure 5K:
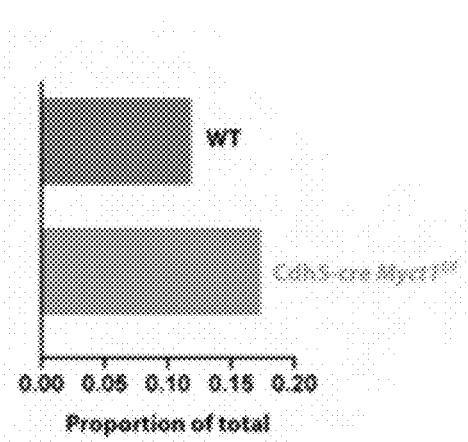
FIG. 5K show normalized proportion of cells (K) in the Stalk-like cells sub-cluster of the tumor endothelial cells from WT and Cdh5-cre Myct1f/f derived by analyzing the SCTtransform data (normalized).
Figure 5L:
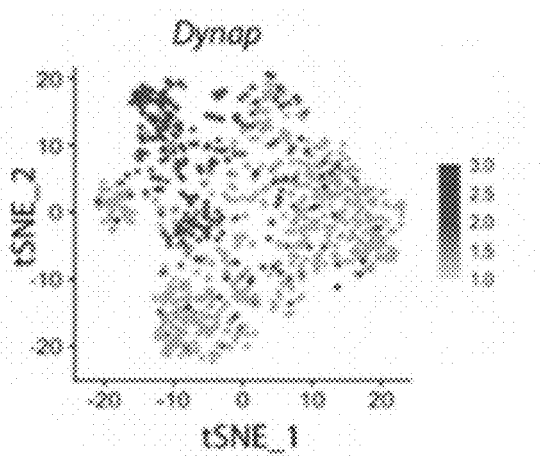
FIG. 5L show feature plot showing Dynap expression pattern (L).
Figure 5M:
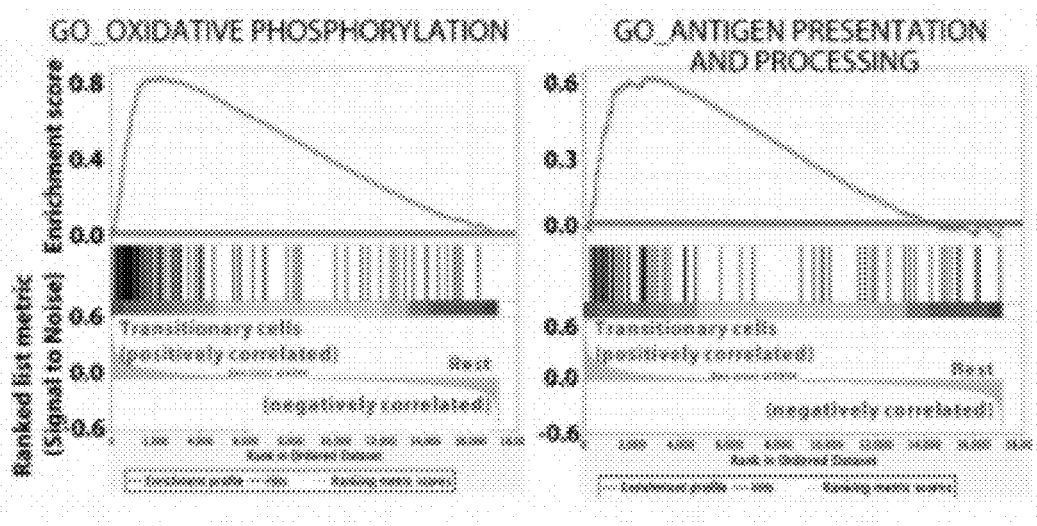
FIG. 5M show gene set enrichment analysis depicting enriched molecular pathways.
Figure 5N:
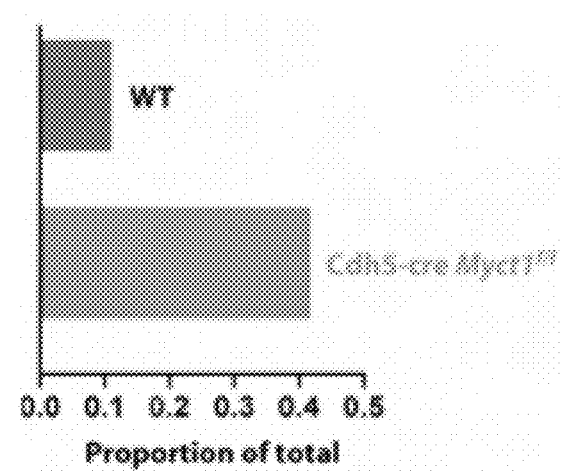
FIG. 5N show normalized proportion of cells (N) in the Transitionary cells sub-cluster of the tumor endothelial cells from WT and Cdh5-cre Myct1f/f derived by analyzing the SCTtransform data (normalized).
Figure 5O:
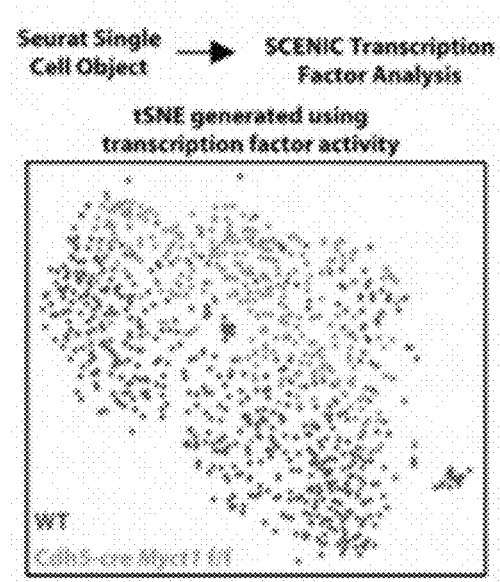
FIG. 5O show tSNE projection.
Figure 5P:
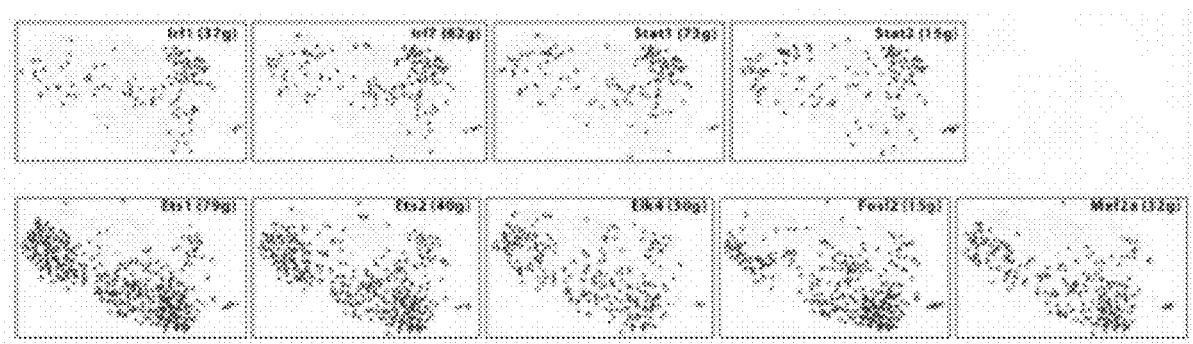

Analysis of Mouse Tumor Endothelial Transcriptome Reveals Myct1 Regulation of Angiogenesis and Immune Responses:

To better understand the tumor endothelial heterogeneity and the potential roles of Myct1 in tumor-ECs, single-cell RNA-sequencing was performed on sorted tumor-ECs from the PyMT-BO1 orthotopic tumor bearing WT and Cdh5-cre Myct1$^{f/f}$ mice using the 10x-genomics platform. Unsupervised hierarchical and Seurat cell-clustering analysis (using a total of 965 ECs) revealed heterogeneity in the tumor endothelium. Distinct clusters of angiogenic, tip-like, stalk-like, proliferating, and transitionary ECs were identified (FIG. 5A-5B). Compared to WT tumor-ECs, Myct1 KO tumor-ECs had a vastly different transcriptional landscape, as evidenced by the reduced angiogenic and tip-like cell populations that are enriched for biological processes related to growth factor activities and invasive vascularization as per Gene Set Enrichment Analysis (FIG. 5C-5H). Myct1 KO tumor-ECs had increased stalk-like and transitionary cell populations that were enriched for biological processes related to leukocyte transendothelial migration, oxidative phosphorylation, and antigen presentation and processing (FIG. 5I-5N), collectively reflecting on the Myct1 requirement for aggressive tumor angiogenesis and tumor immune modulation. SCENIC (Single-cell rEgulatory Network Inference and Clustering) was applied, which scans co-expression of transcription factors and putative target genes and found that WT and Myct1 KO tumor-ECs were in transcriptionally distinct cellular states (FIG. 5O). While angiogenic transcriptional networks were driving the gene expressions in WT tumor-ECs, transcription factors for immune responses were among the prominent transcriptional drivers for gene expressions in Myct1 KO tumor-ECs (FIG. 5P).

Additionally, it was observed that similar patterns of transcriptional activities even in the WT tumor-ECs grouped as Myct1high and Myct1low expressing cells in one other tumor model. Briefly, single-cell RNA-sequencing were performed on sorted tumor-ECs from the LLC subcutaneous transplantation tumor model with only WT mice using the 10x-Genomics® platform. Unsupervised hierarchical cell-clustering analysis (using a total of 1977 ECs) revealed a similar heterogeneity and Myct1 expression pattern in the tumor-ECs. Gene Set Variance Analysis for biological activities on the tumor-ECs based on high and low Myct1 expression revealed a similar enrichment pattern as the WT vs Myct1 KO tumor-ECs. As such, Myct1low ECs were enriched for biological processes related to leukocyte transendothelial migration, whereas Myct1high ECs were enriched for processes related to active vascularization.

Figure 6A:
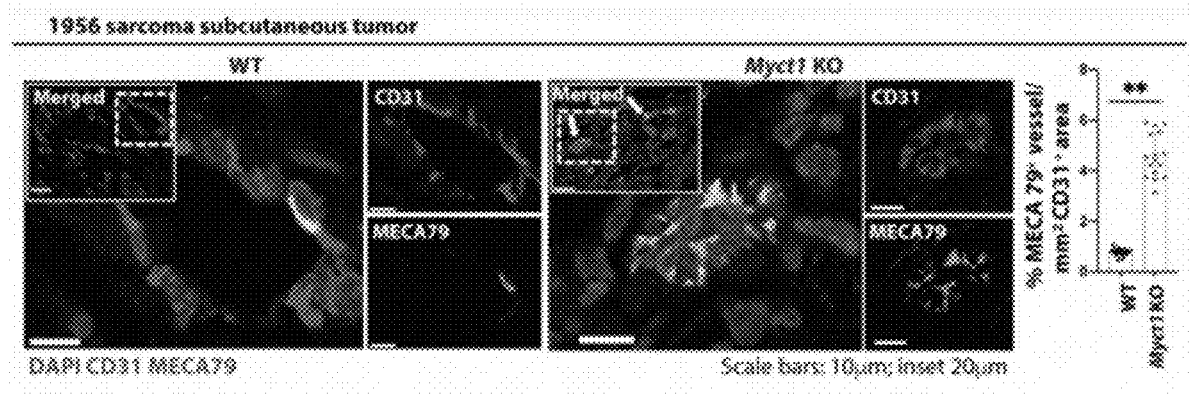
FIG. 6A-6L show Myct1 deficiency promotes an immunostimulatory tumor microenvironment.
Figure 6B:
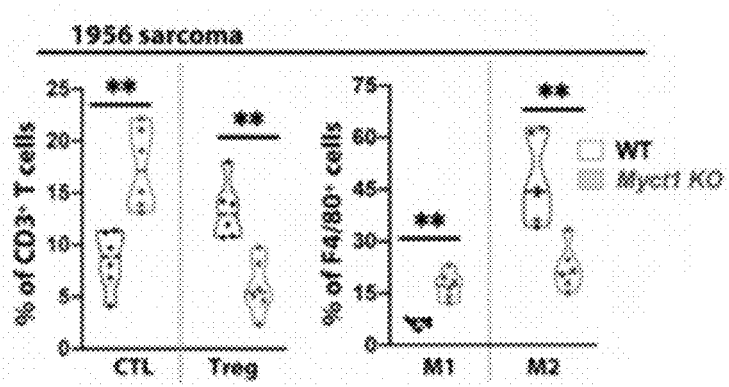
Figure 6C:
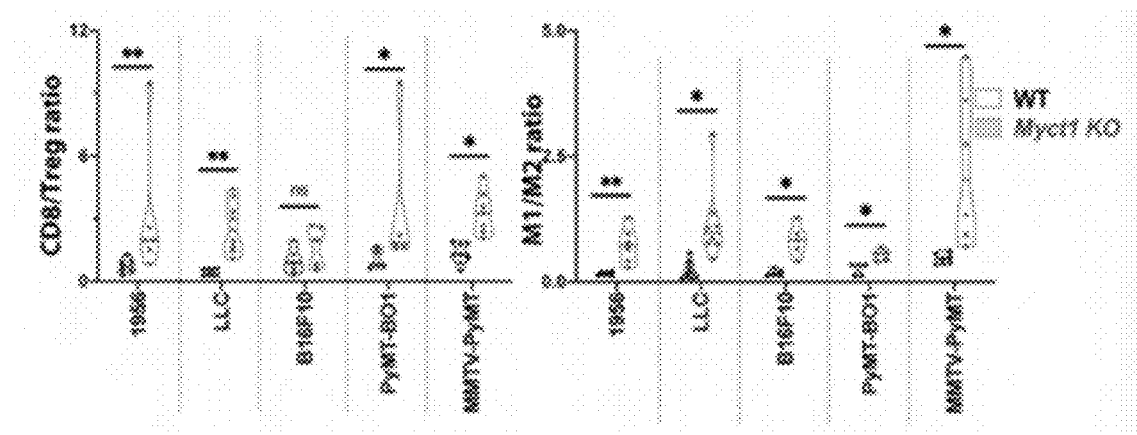
Figure 6D:
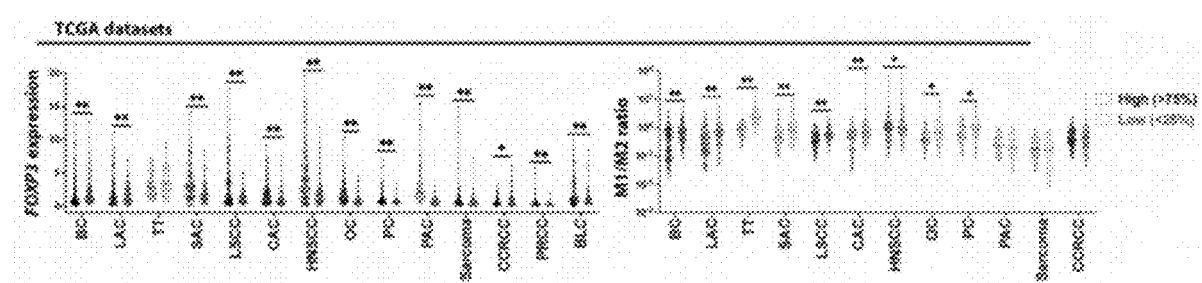

Myct1 Deficiency Leads to Increased Formation of High Endothelial Venules (HEV) in Mouse Tumors and an Overall Immunostimulatory Tumor Microenvironment:

While Myct1 KO mice exhibited reduced tumor vessel formation, it was found that they developed more intratumoral high endothelial venules (HEV) compared to the WT mice (FIG. 6A). HEVs are specialized vascular structures that mediate large scale lymphocyte extravasation in lymphoid organs and inflammatory sites. In solid tumors, HEVs preferentially facilitate infiltration of $CD8^+$ cytotoxic T lymphocytes (CTL) into the tumor, and their presence is correlated with reduced tumor growth and favorable prognosis in cancer patients. The potential role(s) of Myct1 in leukocyte adhesion and endothelial transmigration (see FIG. 5I-5K) and HEV formation (FIG. 6A) suggested a possible alteration of tumor immune environment in the Myct1 KO mice. Indeed, flow cytometric analysis revealed that tumors from Myct1 KO mice exhibited an increase of CTLs and a decrease of immunosuppressive regulatory T cells (Treg), as evident by the increased 'CD8-to-Treg ratios' in all the tumor models (FIG. 6B-6C). Likewise, tumors from Myct1 KO mice had an increased M1-macrophage population and a decreased M2-macrophage population; further manifested by the increased 'M1-to-M2 ratios' in all the tumor models (FIG. 6B-6C). Similar to the Myct1 KO mice, Etv2 conditional KO mice exhibited normalization of tumor vasculature and an immunostimulatory tumor microenvironment, as evidenced by the increased 'CD8-to-Treg' and 'M1-to-M2' ratios (see FIG. 1H-1I). Intriguingly, this anti-tumor immune environment was reversed to a pro-tumor environment following enforced Myct1 expression. Moreover, analysis of TCGA-derived cancer datasets using an immune-cell-deconvolution algorithm from CIBERSORT revealed similar trends. Tumor samples with low MYCT1 expression showed decreased FOXP3 expression, a marker for regulatory T cells, and increased 'M1-to-M2 ratio' compared to the high expression group (FIG. 6D). Additionally, in some cancer types, tumor samples with low MYCT1 expression also exhibited higher frequencies of activated natural killer (NK) cells and activated dendritic cells (DC). Collectively, these observations suggested that Myct1 deficiency in tumor endothelial cells promotes an anti-tumor immune microenvironment.

Figure 6E:
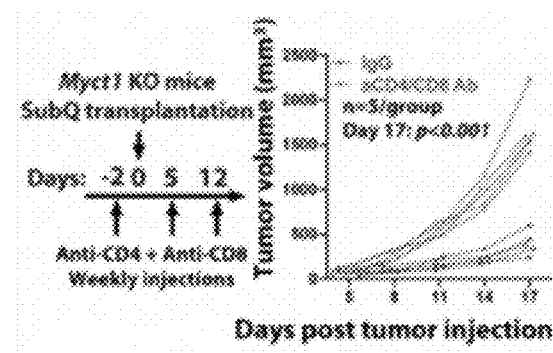
Figure 6F:
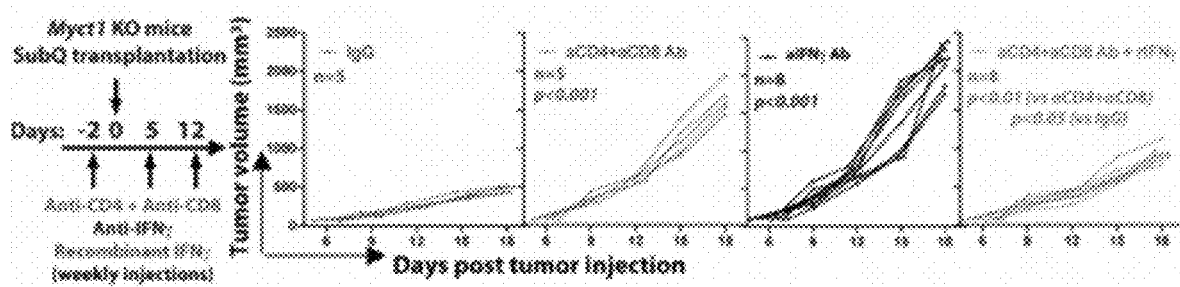

Vascular Normalization-Mediated Tumor Growth Restriction Observed in Myct1 KO Mice is Dependent on Adaptive Immunity:

If, indeed, the increased CTLs in Myct1 KO tumor contributed to the tumor growth restriction, the ablation of CTLs should restore the tumor growth. To this end, neutralizing antibodies were utilized to deplete CD4+ and CD8+ T cell compartments in the tumor-bearing Myct1 KO mice and found that the tumor growth restriction was completely abrogated (FIG. 6E), suggesting that the presence of the adaptive immunity was essential for the anti-tumor activity of Myct1-mediated tumor vessel normalization. This crosstalk between tumor vascular control and adaptive immunity was partly IFNγ-mediated. While IFNγ neutralizing antibody abrogated tumor growth restriction phenotype of Myct1 KO mice, mimicking the $CD4^+$ and $CD8^+$ T cell depletion, recombinant IFNγ treatment partially restored the phenotype in $CD4^+$ and $CD8^+$ T-cell-depleted Myct1 KO mice (FIG. 6F). Together, our data demonstrate that Myct1-mediated tumor vascular control actively shapes the tumor microenvironment through a close engagement with adaptive immunity. Notably, it was also observed a small but statistically significant ($p<0.05$) increase in tumor vessels in the $CD4^+$ and $CD8^+$ T cell-depleted Myct1 KO mice. This observation was similar in principle to a previous report that depletion of $CD8^+$ T cells was associated with a dramatic increase in tumor microvascular frequency. However, the lack of Myct1 could be the reason why it was observed only a modest increase of tumor vasculature even after T cell depletion.

Figure 6G:
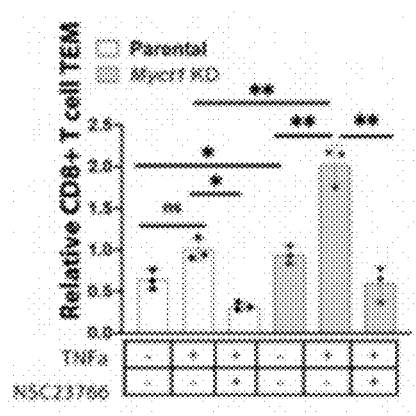
Figure 6H:
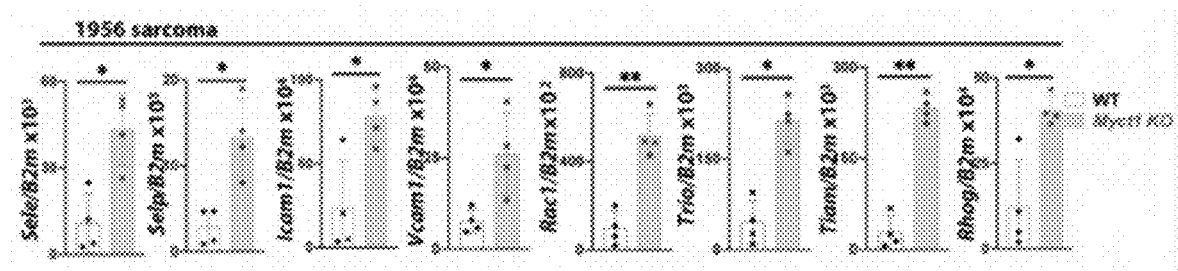
Figure 6I:
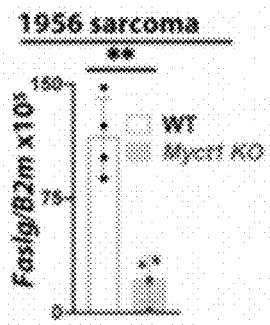
Figure 6J:
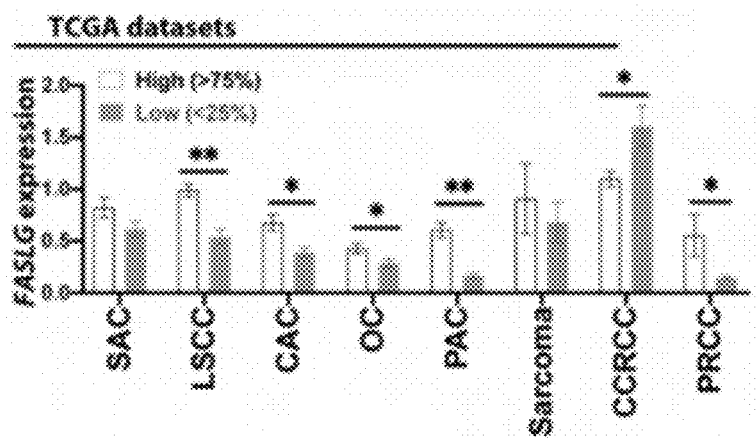
Figures 6K, 6L:
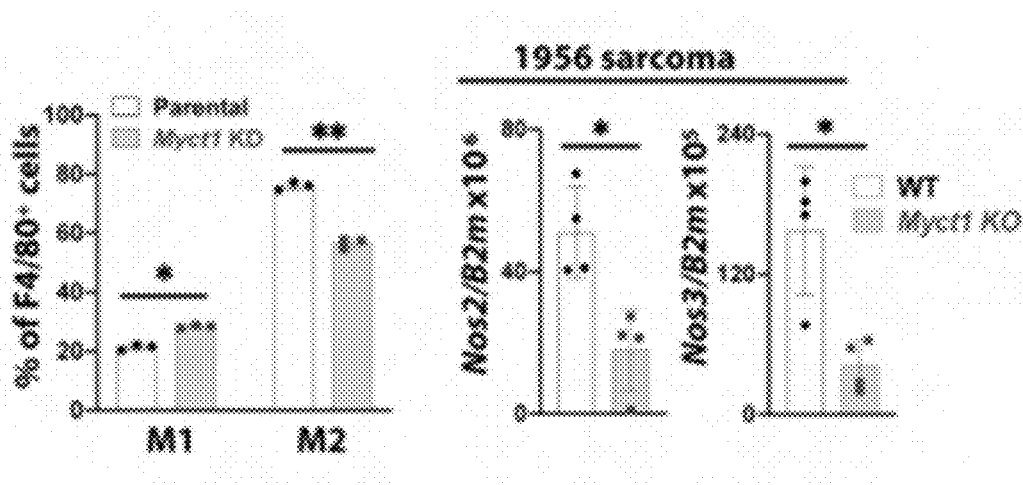

Myct1-Deficient ECs Promote T Cell Trafficking and Skew Macrophage Polarization in the Angiogenic Environment:

Since both the Myct1 KO and Myct1low tumor-ECs were enriched for leukocyte adhesion and transendothelial migration (FIG. 5I-5K), whether Myct1-deficient ECs supported more T cell infiltration was evaluated. By utilizing a modified T cell transendothelial migration assay as described previously, it was found that $CD8^+$ T cells transmigrated through the Myct1-deficient EC barrier more compared to the WT EC barrier (FIG. 6G). However, Treg cells did not display any difference in transmigration between the WT or Myct1 deficient ECs. Mechanistically, Myct1 KO tumor-ECs showed increased expression of endothelial adhesion molecules E- and P-selectin, ICAM-1, and VCAM-1 (FIG. 6H). Moreover, Myct1 KO tumor-ECs had increased expression of Rac1 and associated effector molecules such as Trio, Tiam, and Rhog (FIG. 6H). This upregulation of the Rac1-mediated pathway is crucial as RAC1 inhibition by NSC23766 abrogated the increased T cell migration phenotype (FIG. 6G). Additionally, tumor endothelium is known to express immune-suppressor molecules, such as PDL1, PDL2, Fas ligand, and TRAIL. It was found that the expression of Fas ligand (Fasig), which can induce apoptosis of infiltrating $CD8^+$ T cells by binding to the cognate FAS receptor, was downregulated in Myct1 KO tumor-ECs (FIG. 6I). A similar trend was observed in the tumor samples with low MYCT1 expression compared to the samples with high MYCT1 expression in some human cancer types (FIG. 6J). Finally, it was investigated whether Myct1 expression in tumor endothelium had any direct impact on macrophage polarization. In the presence of respective M1 or M2 polarizing cytokines, Myct1-deficient ECs promoted more M1-like and less M2-like macrophage polarization from monocytes (FIG. 6K). Intriguingly, tumor-ECs in Myct1 KO mice exhibited reduced expression of Nos2 and Nos3 (FIG. 6L), which have been shown to affect M1- and M2-macrophage polarization, suggesting a potential role for nitric oxide synthase (NOS) in the observed anti-tumor macrophage skewing. Together, this series of investigations provided a mechanistic explanation for the observed anti-tumor T-cell and macrophage remodeling phenotype in the Myct1 KO mice.

Figure 7A:
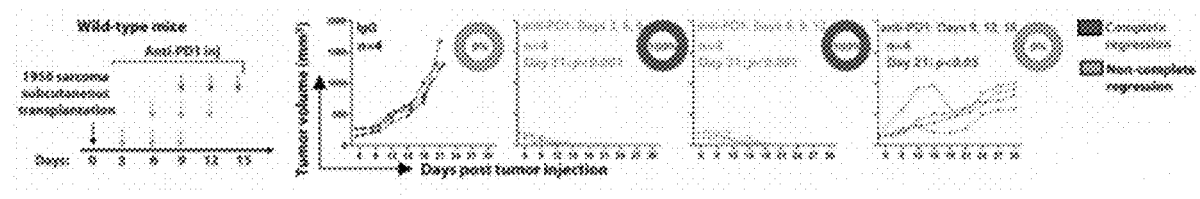
FIG. 7A-7I shows Myct1-targeted siRNA-peptide nanoparticle co-treatment improves anti-PD1 immunotherapy.
Figure 7B:
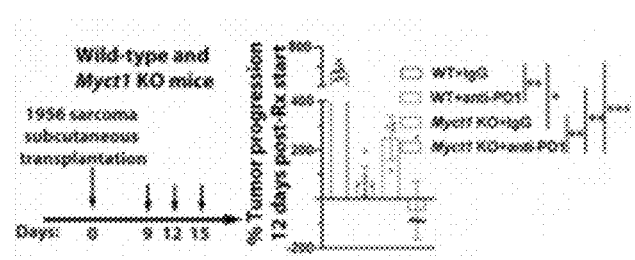
Figure 7C:
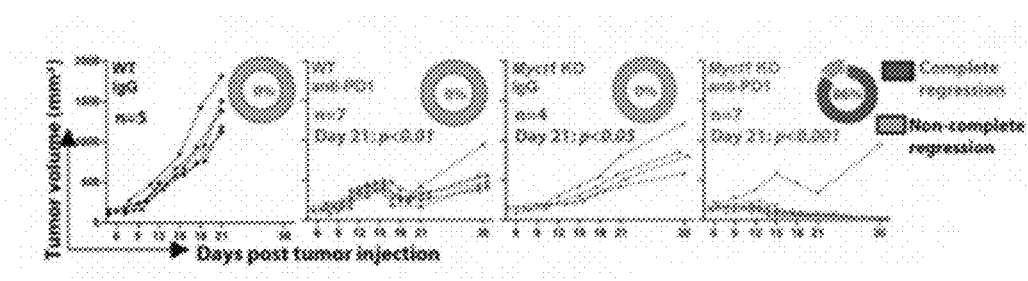
Figure 7D:
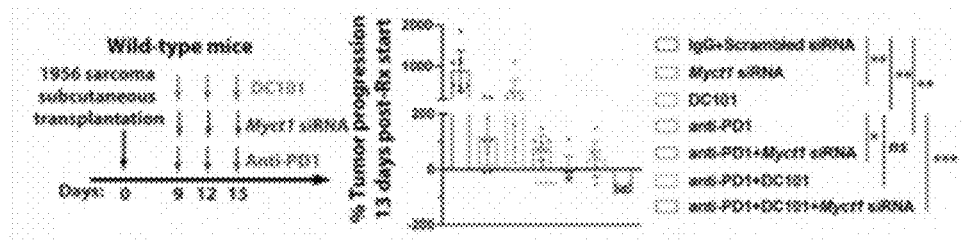
Figure 7E:
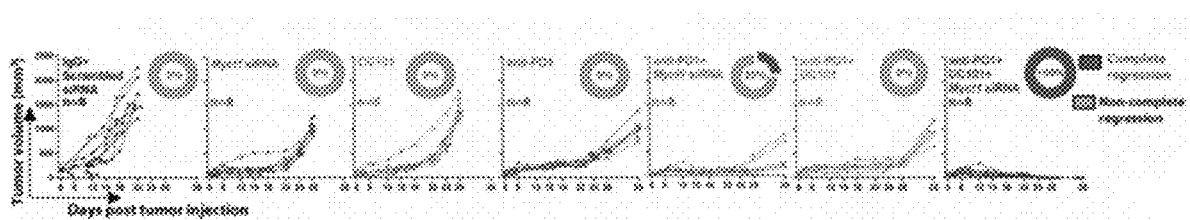
Figure 7F:
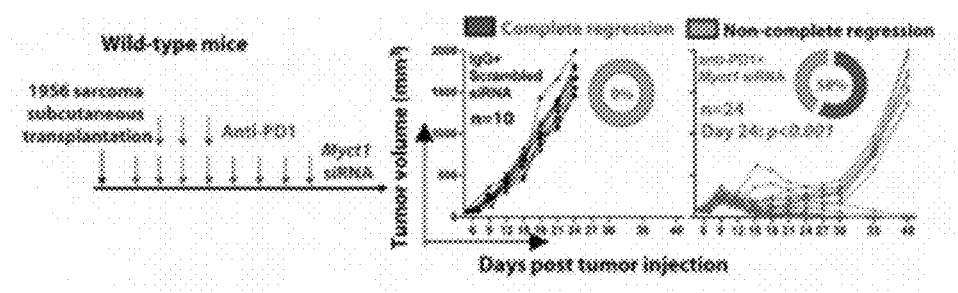

Targeting of Myct1 Improves Anti-PD1 Immunotherapy Outcomes in Mice:

The success of the immune checkpoint blockade-mediated immunotherapeutic approach partially relies on the presence of CTLs in the tumor microenvironment. Since the present example shows that Myct1-deficient tumor endothelium promotes CTL infiltration, addition of anti-PD1 to prevent CTL exhaustion might provide a synergistic and superior treatment outcome. As such, the efficacy and usefulness of the combined anti-Myct1 and anti-PD1 treatment approaches were assessed in both anti-PD1-responsive and anti-PD1-refractory tumor models. First, an anti-PD1-responsive 1956 sarcoma subcutaneous transplantation tumor model was utilized that responds completely to an early-onset scheme of anti-PD1 treatment, but not to late-onset schemes. To this end, different modalities of anti-PD1 therapy were validated in this tumor model and found that a late-onset treatment starting from 9-days post-tumor transplantation did not result in total regression, but somewhat slowed tumor progression with eventual complete relapse of the tumor in WT mice (FIG. 7A). The tumor-bearing Myct1 KO mice were treated with this late-onset anti-PD1 scheme and observed dramatic tumor regression within 12 days of treatment initiation (FIG. 7B). This short-term regression led to complete tumor regression in all but one treated mouse (7 out of 8) (FIG. 7C). Supporting our observation that endothelial-specific Myct1 regulates the tumor growth and angiogenesis, Cdh5-cre Myct1f/f mice demonstrated a similar tumor regression with this late-onset anti-PD1 treatment scheme. To determine whether a systemic anti-Myct1 approach confers similar anti-tumor activity, a Myct1 directed siRNA-peptide nanoparticle treatment approach was utilized in WT mice either alone or in combination with DC101 (a VEGF receptor 2 (VEGFR2) blocking antibody) and/or anti-PD1, following a similar late-onset treatment scheme (FIG. 7D). It was found that combined anti-PD1 and anti-Myct1 treatment restricted tumor progression in all the treated mice (FIG. 7D), with a complete regression in 25% of the mice (2 out of 8) (FIG. 7E). In comparison, combined anti-PD1 and DC101 treatment also produced significant ($p<0.05$) short-term tumor growth restriction, though to a somewhat lesser extent (FIG. 7D), with an eventual relapse of tumor growth in all mice (FIG. 7E). Remarkably, anti-PD1 treatment with the dual blockade of Myct1 and VEGFR2 resulted in complete tumor regression in all of the treated mice (FIG. 7E). Since combined Myct1 siRNA and anti-PD1 treatment resulted a complete tumor regression in 2 out of 8 mice (FIG. 7E), while anti-PD1 treatment in Myct1 KO mice led to complete tumor regression in 7 out of 8 mice (FIG. 7C), whether this was due to a sub-optimal Myct1 siRNA treatment was assessed. An extended anti-Myct1 treatment approach was utilized that started before the onset and continued after the termination of the anti-PD1 treatment. This prolonged anti-Myct1 treatment was found to result in the restriction of tumor progression for a longer period, with about 60% mice showing complete tumor regression (14 out of 24 mice) (FIG. 7F).

Figure 7G:
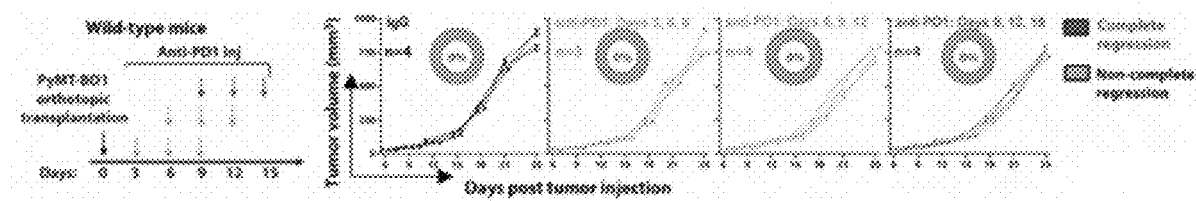
Figure 7H:
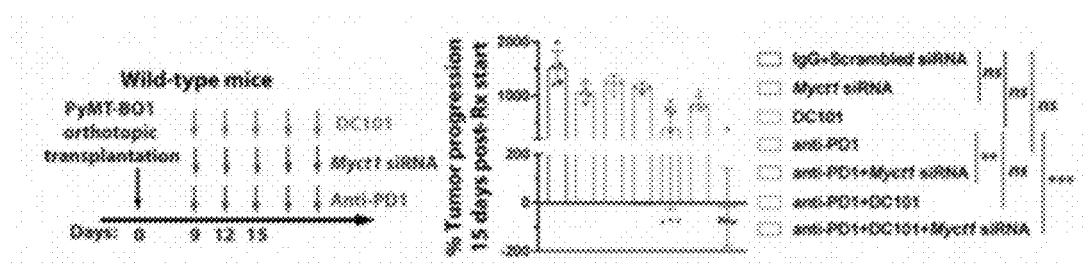
Figure 7I:
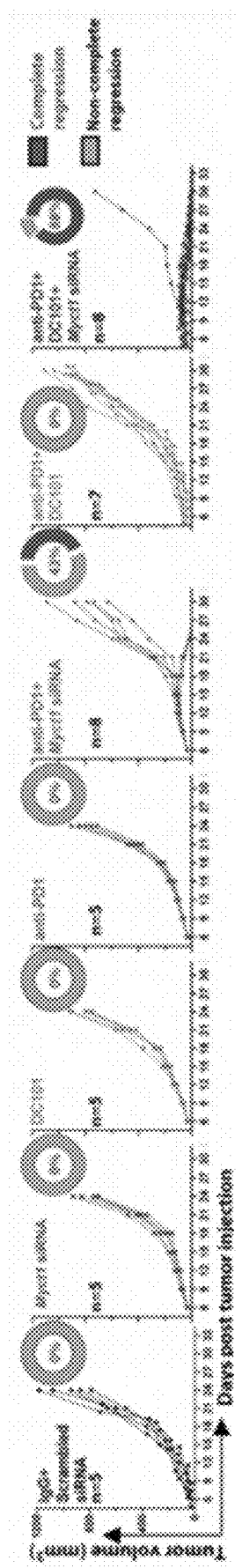

Next, it was assessed whether Myct1 targeting could sensitize anti-PD1-refractory tumors. Here, an orthotopic breast tumor model was utilized with PyMT-BO1 tumors that do not respond to anti-PD1 treatment (FIG. 7G). tumor-bearing WT mice were treated with Myct1-directed siRNA-peptide nanoparticles either alone or in combination with DC101 and/or anti-PD1. Although DC101 failed to induce any sensitivity to anti-PD1 treatment, combined anti-Myct1 and anti-PD1 treatment resulted in a substantial short-term tumor regression (FIG. 7H), with complete tumor regression in 43% of the treated mice (3 out of 7) (FIG. 7I). Intriguingly, similar to the 1956 sarcoma model, dual blockade of Myct1 and VEGFR2 with anti-PD1 treatment generated both the maximal short-term tumor restriction and long-term complete tumor regression (7 out of 8 mice) (FIG. 7H-7I), suggesting that the collective blockade of both the VEGF and MYCT1 pathways might provide better and longer-lasting vascular control, resulting in improved outcomes with anti-PD1 immunotherapy in both sensitive and refractory tumor models.

Dormant tumor cells can reinitiate tumor growth after treatment. To address if dormant tumor cells still existed in these transplant tumor models after anti-Myct1 and anti-PD1 treatment, the tumor-regressed mice were treated (pooled from the experiments with 1956 sarcoma tumor model described in FIG. 7E-7F) with monoclonal neutralizing antibodies against CD4, CD8, and IFNγ, three major components of adaptive immunity. None of the tumor-regressed mice developed any tumor mass after the alleviation of the immune surveillance for a period of over 90 days, suggesting that anti-PD1 treatment combined with anti-Myct1 targeting, with or without other anti-angiogenics, not only brought complete tumor regression but also destroyed any potential dormant tumor cells residing in the equilibrium phase. Intriguingly, re-challenging both the tumor-regressed mice (pooled from the experiment with PyMT-BO1 tumor model described in FIG. 7H) and naïve control mice with the PyMT-BO1 tumor cells resulted in unrestrained tumor growth without any statistical difference, suggesting that anti-Myct1 and anti-PD1 combination treatment did not induce long-lived immunological memory.

Figure 8A:
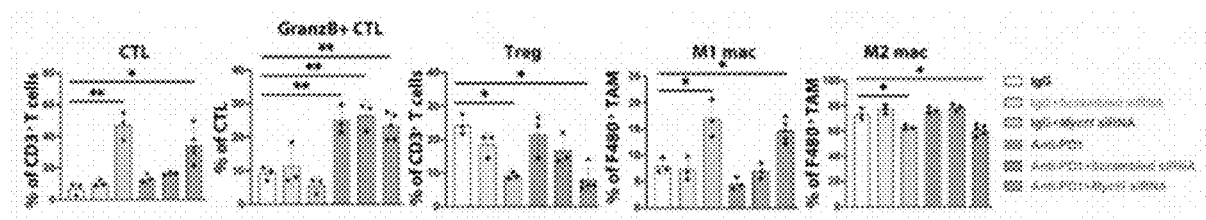
FIG. 8A-8F shows anti-Myct1 works synergistically with anti-PD1 treatment to improve outcomes in mice.
Figure 8B:
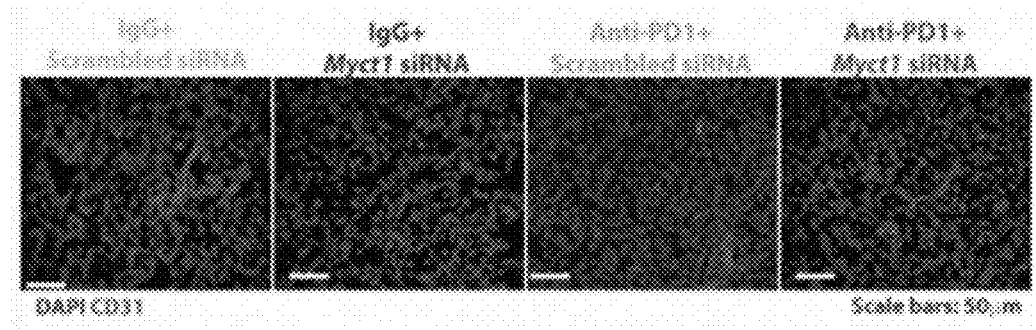
Figure 8C:
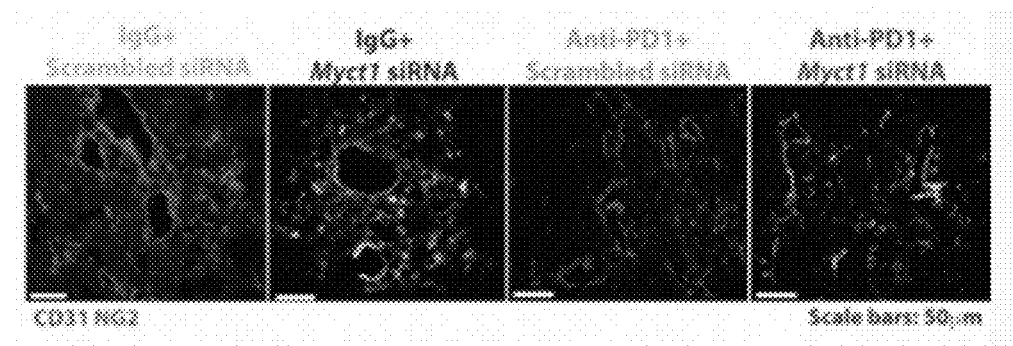
Figure 8D:
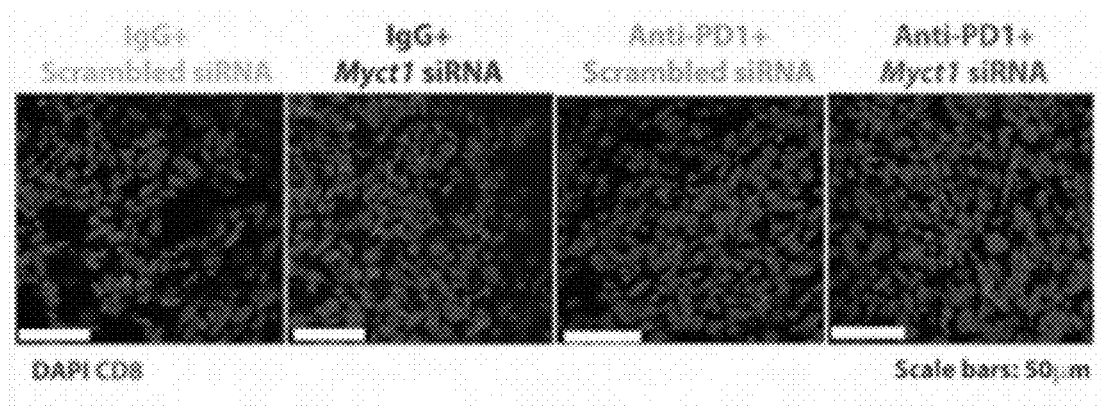
Figure 8E:
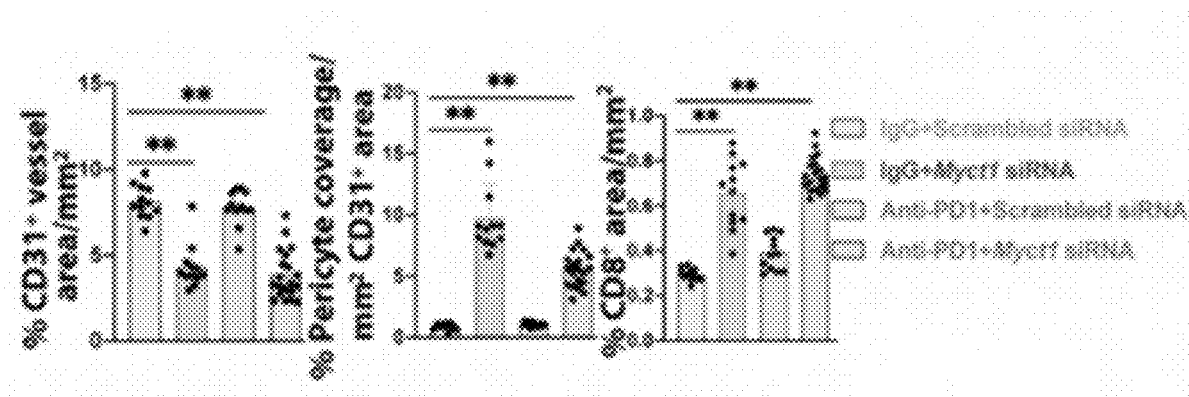
Figure 8F:
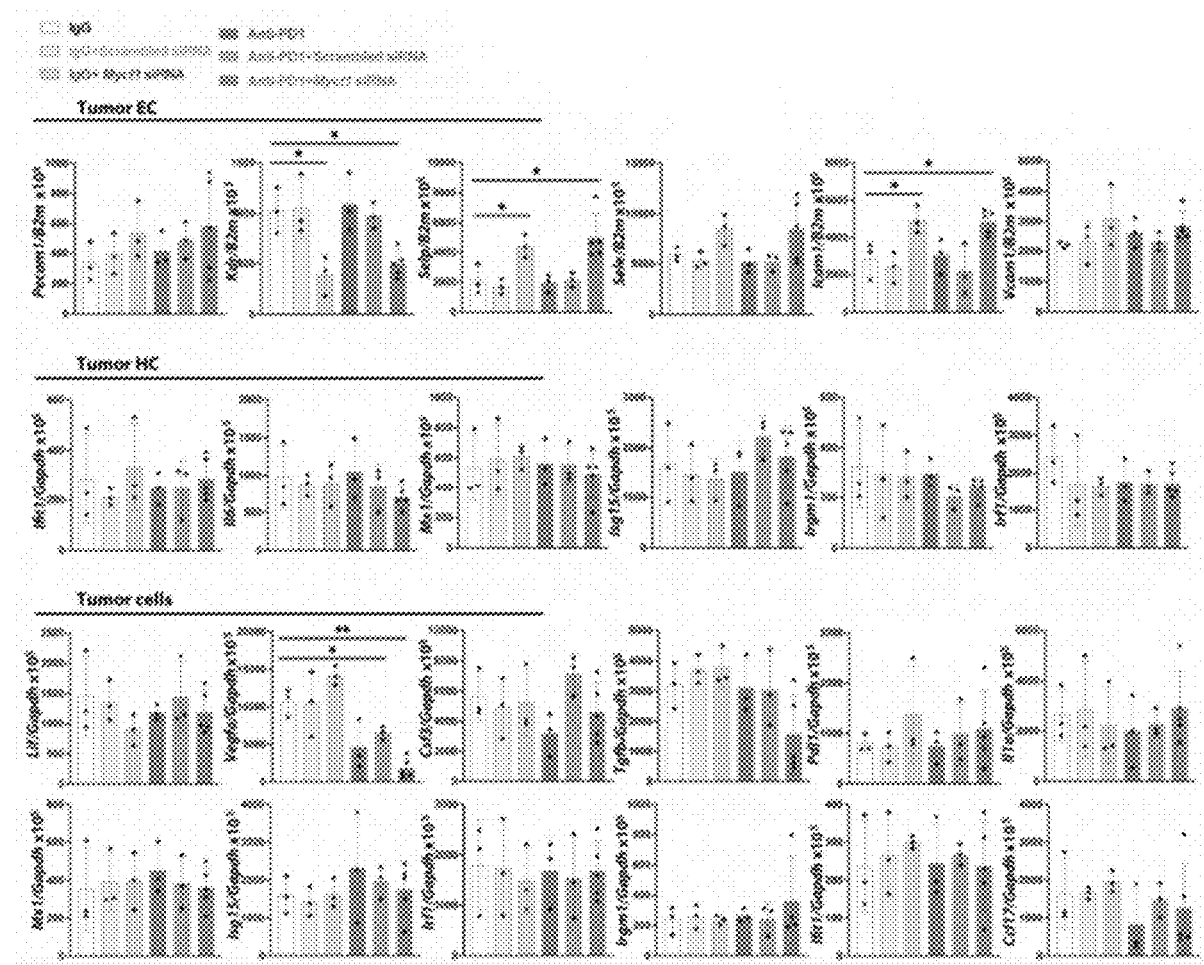

To further understand how Myct1-directed siRNA-peptide nanoparticle treatment improves the outcome of the anti-PD1 immunotherapy, tumors were harvested and analyzed seven days after treatment initiation in the anti-PD1 refractory PyMT-BO1 tumor model, at a time when the tumors just started to respond to combination treatment. Flow cytometric analysis revealed that anti-Myct1 treatment increased CTLs and M1 macrophages, while reducing the number of Treg cells and M2 macrophages. Conversely, anti-PD1 treatment increased the percentage of Granzyme $B^+$ CTLs but did not alter the immune microenvironment. Notably, anti-Myct1 and anti-PD1 combined treatment increased both the influx of CTLs and the percentage of Granzyme $B^+$ CTLs, suggesting that the combination treatment produces considerably superior tumor control due to the additive nature of the individual treatments on CTLs (FIG. 8A). Immunofluorescence observations supported the conclusion that anti-Myct1treatment reduced angiogenesis, improved vascular normalization, and increased the infiltration of $CD8^+$ T cells (FIG. 8B-8E). Intriguingly, although the siRNA-peptide nanoparticle treatment downregulated Myct1 expression in both the tumor and non-tumor endothelium, unlike in the tumor masses, there were no alterations in the immune constituents of the non-tumor tissues. a similar modification of immune constituents was observed of the tumor masses in the Myct1 KO mice with the anti-PD1 treatment, supporting the notion of the additive nature of the treatments. Downregulation of Myct1 by the nanoparticles led to the upregulation of several adhesion molecules, among which Selp and Icam1 reached statistical significance (p<0.05), only in the tumor endothelium but not in the non-tumor tissues (FIG. 8F), corroborating the observations in the Myct1 KO mice (see FIG. 6H). Importantly, Myct1-directed siRNA-peptide nanoparticle treatment largely did not induce any non-specific immune responses in either the tumor-infiltrating hematopoietic cells or tumor cells (FIG. 8F). Collectively, these observations suggest that Myct1 targeting generates tumor-EC-focused changes that allows anti-PD1 treatment to mount more effective anti-tumor responses.

DISCUSSION

Myct1 was first identified as a direct target gene of c-MYC in myeloid cells, as well as in laryngeal squamous cell carcinoma cells, in the context of c-MYC overexpression. However, analysis of published scRNA sequencing datasets from different mouse organs revealed that Myct1 expression is mostly restricted to ECs and hematopoietic stem and progenitor cells. The present Example has demonstrated that Myct1 is highly expressed in tumor ECs and is a regulator of angiogenesis. It was found that Myct1 is not required for blood and vascular development. Instead, Myct1 seems to regulate acute angiogenic demand in pathological conditions such as cancer. Notably, data from human patients with varying MYCT1 expression across multiple different cancer types also suggest that MYCT1 is positively correlated with the angiogenic status of the cancers. Particularly, it was shown that MYCT1 regulates EC motility by interacting with ZO1 and CKAP4 and modulating Rho GTPases and actin cytoskeleton.

Myct1 deficient tumor vasculature is characterized by having more HEVs, facilitating CTLs infiltration, and promoting anti-tumor macrophage polarization. Tumor vessels inhibit CTLs activation and promote apoptosis of the infiltrating immune cells in part by upregulating immunosuppressive molecules, PDL1, PDL2, Fas ligand, and TRAIL. It was found that Myct1 deficient ECs downregulate the expression of Fas ligand. It was also found a similar trend with human cancers with reduced MYCT1 expression. The present Example suggest that Myct1 deficient endothelium promotes an immunostimulatory microenvironment by enhancing CTLs infiltration and presumably by preventing CTLs apoptosis. Moreover, it has been reported that inducible-NOS (NOS2) inhibits the M1-macrophage population, whereas endothelial-NOS (NOS3) promotes the M2-macrophage polarization. Notably, the expressions of Nos2 and Nos3 were decreased in Myct1 deficient ECs, suggesting that enhanced anti-tumor macrophage polarization in Myct1 deficient tumor microenvironments may, in part, through the regulation of NO production of ECs. These findings collectively provide mechanistic insights into Myct1 deficient tumor vessels contributing to an immunostimulatory microenvironment.

Vascular normalization has been implicated to influence local tumor immune environment. However, the molecular targets like VEGF and associated pathways also impact the immune cells in an endothelial cell-independent manner, raising a possibility of synergistic and/or independent effect rather than a sole consequence of vascular normalization on the tumor immune components. Myct1 targeting in endothelial cells leading to an anti-tumor microenvironment provides more definitive evidence for endothelial regulation of tumor immunity in mice. This data is consistent with the human cancer datasets that show the increased presence of immunostimulatory components in tumors with lower MYCT1 expression. Our finding supports the emerging notion that combined vascular and immune control would provide a synergistic anti-tumor activity. Indeed, the present Example demonstrate that targeting Myct1 improves the response to anti-PD1 therapy in treatment-responsive and -refractory tumors. Importantly, it was observed that combined Myct1 and VEGF targeting with anti-PD1 treatment produced a superior tumor control, suggesting a potential synergy between Myct1 and VEGF pathways.

In summary, the present Example has identified Myct1 as a regulator of tumor angiogenesis. Myct1-deficient ECs display suboptimal angiogenesis, facilitate HEV formation, enhance robust CTL infiltration, and promote inflammatory M1 macrophage polarization. Anti-PD1 antibody treatment in the context of Myct1 inhibition augments complete tumor elimination in mouse models. Thus, the present Example provides proof-of-principle that combined Myct1-inhibition and immunotherapy might become a treatment regimen for cancer patients.

Methods

Study Design:

The goal of the study was to investigate the role of Myct1 as a regulator of tumor angiogenesis and anti-tumor immunity and to characterize the mechanism of this regulation. The Cancer Genome Atlas (TCGA) datasets for thirteen different cancer types were analyzed to identify Myct1 as an angiogenic gene downstream of Etv2. Myct1 requirement for tumor growth, angiogenesis, and antitumor immunity was assessed by using different preclinical mouse models of cancer (18, 26, 57, 71-76). Potential correlation between endothelial Myct1 expression and the immune output in the human tumor microenvironment was evaluated by analyzing cancer datasets using the CIBERSORT deconvolution algorithm. Using various in vitro assays, the role(s) of Myct1 in endothelial cells and the underlying mechanisms for regulating anti-tumor immunity were rigorously investigated. Lastly, using both the knockout mice and siRNA-peptide nanoparticle mediated approach, the efficacy of Myct1 inhibition for treating tumors in combination with anti-PD1 immunotherapy was evaluated. For animal studies, the minimum number of subjects used in any experiments was 5/group to attain a statistical significance of $p<0.05$ with a power of at least 80%, considering the mean differences between experimental groups would be >20% and the pooled standard deviation would be ~20%. For in-vitro experiments, the anticipated mean difference was even more, and hence the sample size was kept at 3 or more/ group. Age- and sex-matched mice were randomly assigned into groups in all experiments except experiments utilizing both the genetic and orthotopic breast tumor models, where only female mice were used. The investigators were not aware of the group allocation until the treatment, data collection, and data analysis were done. All experimental data were reliably reproduced in two or more individual biological replicates unless indicated otherwise. No data were excluded from analysis. Sample sizes, biological replicates, and statistical methods are provided in the corresponding figure legends.

Mice: Myct1$^{-/-}$ (Myct1 KO) and Cdh5-Cre; Myct1$^{f/f}$ mice were generated at Washington University in St. Louis and Emory University, respectively. MMTV-PyMT mice were a gift from Mikala Egeblad, Cold Spring Harbor Laboratory, and crossed with Myct1 KO mice to generate Myct1 KO in the presence of MMTV-PyMT transgene (MMTV-PyMT Myct1$^{-/-}$) at Washington University in St. Louis. C57BL/6 mice were used as wild-type mice in this study. Myct1$^{-/-}$ (Myct1 KO) mice were generated at the Genome Engineering and iPSC Center (GEIC), Washington University in St. Louis by utilizing the CRISPR/CAS9 technology. Briefly, the gRNA SM767.Myct1.g1 was selected for oocyte microinjection. The resulted F0 mosaic pups were genotyped with targeted deep sequencing to identify pups with the majority of the reads being out-of-frame. Next, the selected pup (ID #9129) was crossed with C57BL/6 wild-type mice to get the F1 heterozygous mice. Finally, sibling mating of the sequence-verified F1 heterozygous mice (Myct1$^{+/-}$) produced F2 Myct1 KO mice with a 2 bp insertion and 6 bp deletion in the first exon of the Myct1 gene, which generated an early stop codon and resulted in knocking out of the gene. Cdh5-Cre; Myct1$^{f/f}$ mice were generated at the Emory University. Briefly, to generate Myct1$^{f/f}$ mice, the loxP sequences were inserted in front of exon 2 and immediately after the termination codon of Myct1 (Cyagen, Santa Clara, CA). After confirming the germ line transmission, the Neo$^R$ selection cassette was deleted, and Myct1$^{f/+}$ mice were crossed with Myct1$^{f/+}$ mice to generate Myct1$^{f/f}$ mice. Subsequently, Myct1$^{f/f}$ mice were crossed with Cdh5-Cre mice (The Jackson Laboratory, Bar Harbor, ME) to generate Cdh5-Cre; Myct1$^{f/f}$ conditional KO mice (EC specific Myct1 KO). The resulting mice were born alive, fertile, and did not show any phenotypic defect. MMTV-PyMT mice were a gift from Mikala Egeblad, Cold Spring Harbor Laboratory, and crossed with Myct1 KO mice to generate Myct1 KO in the presence of MMTV-PyMT transgene (MMTV-PyMT Myct1$^{-/-}$). VECadherin-Cre; Etv2 CKO (VECadherin-Cre; Etv2$^{flox/flox}$) mice were generated as described previously (18). Littermate subjects were used as a control with the different knockout mice. Both male and female mice were used in an equal quantity in any given experiment except experiments utilizing both the genetic and orthotopic breast tumor models, where only female mice were used. The ages of the experimental animals were between 10 and 12 weeks.

Preparation of Myct1 esiRNA-p5RHH Peptide Nanoparticle: For esiRNA nanoparticle treatment study, MISSION® esiRNA targeting mouse Myct1 (Cat: EMU033761) was purchased. MISSION® siRNA Universal Negative Control #1 (Cat: SIC001) was used as scrambled siRNA control. 100 mM esiRNA solution was prepared by dissolving in siRNA buffer (Cat: B-002000-UB-100, Dharmacon). 10 mL of the esiRNA suspension was mixed with 5 mL of 20 mM p5RHH peptide solution and 185 mL of 1×HBSS (Gibco) to prepare the nanoparticle complex and immediately injected into the mouse through the tail vein.

pLKpuro lentiviral mouse Myct1 shRNA clones TRCN0000246636 (NM_026793.2-680521c1), TRCN0000246635 (NM_026793.2-213s21c1), TRCN0000246634 (NM_026793.2-2456s21c1), TRCN0000246633 (NM_026793.2-268521c1), and TRCN0000257743 (NM_026793.2-459521c1); mouse Zo1 shRNA clones TRCN0000091618 (NM_009386.1-5678s1c1), TRCN0000091619 (NM_009386.1-4410s1c1), TRCN0000091620 (NM_009386.1-1925s1c1), TRCN0000091621 (NM_009386.1-3986s1c1), and TRCN0000091622 (NM_009386.1-5003s1c1); mouse Rhoa shRNA clones TRCN0000068201 (NM_016802.3-733s1c1), TRCN0000311121 (NM_016802.4-524s21c1), TRCN0000304743 (NM_016802.4-682s21c1), TRCN0000302388 (NM_016802.4-733s21c1), and TRCN0000304744 (NM_016802.4-605s21c1); mouse Arhgdia shRNA clones TRCN0000106162 (NM_133796.3-579s1c1), TRCN0000106161 (NM_133796.3-858s1c1), TRCN0000106163 (NM_133796.3-651s1c1), TRCN0000316502 (NM_133796.6-680s21c1), TRCN0000316589 (NM_133796.6-401s21c1); mouse Etv2 shRNA clones TRCN0000084284 (NM_007959.1-93s1c1), TRCN0000084285 (NM_007959.1-52s1c1), TRCN0000084286 (NM_007959.1-887s1c1), and TRCN0000084287 (NM_007959.1-888s1c1); human MYCT1 shRNA clones TRCN0000137125 (NM_025107.1-323s1c1), TRCN0000136533 (NM_025107.1-305s1c1), TRCN0000135843 (NM_025107.1-262s1c1), TRCN0000423596 (NM_025107.2-60s21c1), and TRCN0000423608 (NM_025107.2-996s21c1) were purchased from Millipore Sigma. HEK293T cells were transfected with the mentioned shRNA, or pCSII-EF1-(HA-mouseMYCT1)-IRES2-Bsr, or pCSII-EF1-(mouseMYCT1-FLAG)-IRES2-Bsr, pcDNA3-EGFP-RHOA-wt, or pCB6-ZO1-myc, or pCSII-EF1-humanMYCT1-IRES2-Bsr constructs, along with pCAG-HIVgp and pCMV-VSV-G-RSV-Rev (with a ratio of 4:3:1) by using Calcium Phosphate method. Sixteen hours after transfection, media was changed, and cells were then grown for additional 48h. Subsequently, supernatant was harvested and concentrated by Lenti-X-Concentrator (Cat: 631232, Clontech®). The virus titer was determined using the Lenti-X™ p24 Rapid Titer Kit (Cat: 632200, Clontech®).

Mouse Tumor Models:

MMTV-PyMT transgenic mice were utilized to generate a spontaneous model of breast cancer, where MMTV-LTR drives the expression of mouse mammary gland-specific polyomavirus middle T-antigen. For tumor transplantation studies, LLC-GFP, B16F10 melanoma, and 1956 sarcoma tumor cells were injected subcutaneously to the back of the mice. PyMT-BO1 tumor cells were injected orthotopically to the mammary fat pad of the female mice.

Cell Lines:

Mouse cardiac endothelial cells (MCEC) and human umbilical vein endothelial cells (HUVEC) were purchased from CELLutions Biosystems Inc. (Cat: CLU510) and ATCC (Cat: ATCC CRL-1730), respectively. Overexpressing and shRNA lentiviral particles were utilized to generate different genetically modified overexpressing and knockdown stable cell lines.

Single-cell RNA sequencing: Endothelial cells sorted by flow cytometry from the tumor masses were loaded on a Chromium Single Cell Instrument (10x Genomics®) to generate single-cell GEMs. Single-cell RNA-seq libraries were prepared using version 2 Chromium Single-cell 3' Library, Gel Bead & Mutiplex Kit (10x Genomics®). Sequencing was performed on Illumina NextSeq2500 and mapped to the mouse genome (build mm10) using CellRanger software (10x Genomics®, version 2.1.1). Sequencing data is available as GSE157879 and GSE146819.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

What is claimed is:

1. A method of treating a solid-tumor cancer in a subject in need thereof, the method comprising:
administering to the subject a composition comprising an shRNA or siRNA specific for Myc target protein 1 (MYCT1) mRNA, wherein the shRNA or siRNA reduces MYCT1 protein expression in endothelial cells at a tumor of the solid-tumor cancer, which reduces tumor angiogenesis and increases cytotoxic T cell transendothelial migration at the tumor in the subject.

2. The method of claim 1, wherein the shRNA or siRNA is specifically antisense to MYCT1 mRNA that encodes full-length MYCT1 comprising the amino acid sequence set forth in SEQ ID NO: 1.

3. The method of claim 1, which reduces tumor progression in the subject.

4. A method of reducing tumor angiogenesis and increasing anti-tumor immunity in a subject in need thereof, wherein the subject has a solid-tumor cancer, the method comprising:
administering to the subject a composition comprising an shRNA or siRNA specific for Myc target protein 1 (MYCT1) mRNA, wherein the shRNA or siRNA reduces MYCT1 protein expression in endothelial cells at a tumor of the solid-tumor cancer, which increases cytotoxic T cell transendothelial migration at the tumor in the subject.

5. The method of claim 1, wherein the shRNA or siRNA is administered using a delivery vehicle.

6. The method of claim 5, wherein:
the subject is administered the shRNA and the delivery vehicle is selected from a viral vector and/or a lentiviral particle; or
the subject is administered the siRNA and the delivery vehicle is selected from a nanoparticle, liposome, phospholipid, microemulsion, micelle, or dendrimer.

7. The method of claim 1, which increases inflammatory M1 macrophage polarization and decreases M2 macrophage polarization at the tumor in the subject.

8. The method of claim 1, which increases infiltration of CD3+ T cells and CD8+ T cells at the tumor in the subject.

9. The method of claim 1, which reduces infiltration of regulatory T cells at the tumor in the subject.

10. The method of claim 1, which reduces CD31+ vascular density at the tumor in the subject.

11. The method of claim 1, which increases pericyte coverage at the tumor in the subject.

12. The method of claim 1, which does not induce a non-specific immune response in tumor-infiltrating hematopoietic cells and tumor cells.

13. The method of claim 1, which improves anti-tumor drug delivery in the subject.

14. The method of claim 1, further comprising administering to the subject an anti-PD-1 immunotherapy.

15. The method of claim 14, wherein the shRNA or siRNA and the anti-PD-1 immunotherapy act synergistically in the subject.

16. The method of claim 15, which increases infiltration of CD3+ cytotoxic T cells and CD8+ T cells at the tumor in the subject.

17. The method of claim 15, which increases infiltration of Granzyme B+ cytotoxic T cells at the tumor in the subject.

18. The method of claim 15, which reduces infiltration of regulatory T cells at the tumor in the subject.

19. The method of claim 15, which increases inflammatory M1 macrophage polarization and decreases M2 macrophage polarization at the tumor in the subject.

20. The method of claim 15, which reduces CD31+ vascular density at the tumor in the subject.

21. The method of claim 15, which increases pericyte coverage at the tumor in the subject.

22. The method of claim 15, which reduces tumor progression in the subject.

23. The method of claim 15, which increases infiltration of Granzyme B+ cytotoxic T cells at the tumor in the subject.

24. The method of claim 1, further comprising administering to the subject an anti-PD-1 immunotherapy and a VEGF-targeted therapy.

25. The method of claim 24, wherein the VEGF-targeted therapy is an anti-VEGF receptor immunotherapy.

26. The method of claim 24, wherein the shRNA or siRNA, anti-PD-1 immunotherapy, and VEGF-targeted therapy act synergistically in the subject.

27. The method of claim 26, which reduces tumor progression in the subject.

28. The method of claim 1, wherein the solid-tumor cancer is a sarcoma.

29. The method of claim 28, wherein the sarcoma is selected from uterine sarcoma, a soft tissue sarcoma, Ewing sarcoma, Kaposi sarcoma, osteosarcoma, or rhabdomyosarcoma.

30. The method of claim 29, wherein the sarcoma is a uterine sarcoma.

31. The method of claim 1, wherein the solid-tumor cancer is breast cancer.

* * * * *